(12) United States Patent
Merkulov et al.

(10) Patent No.: US 6,908,747 B2
(45) Date of Patent: Jun. 21, 2005

(54) ISOLATED HUMAN RAS-LIKE PROTEINS, NUCLEIC ACID MOLECULES ENCODING THESE HUMAN RAS-LIKE PROTEINS, AND USES THEREOF

(75) Inventors: Gennady V. Merkulov, Baltimore, MD (US); Valentina Di Francesco, Rockville, MD (US); Ellen M. Beasley, Damestown, MD (US)

(73) Assignee: Applera Corporation, Norwalk, CT (US)

(*) Notice: Subject to any disclaimer, the term of this patent is extended or adjusted under 35 U.S.C. 154(b) by 511 days.

(21) Appl. No.: 09/820,003

(22) Filed: Mar. 29, 2001

(65) Prior Publication Data

US 2002/0142382 A1 Oct. 3, 2002

(51) Int. Cl.[7] .................................................. C12P 21/06
(52) U.S. Cl. .................... 435/69.1; 536/23.1; 536/23.5; 435/320.1; 435/325; 530/350
(58) Field of Search .......................... 530/350; 536/23.5, 536/23.1, 24.1; 435/320.1, 325, 69.1

(56) References Cited

FOREIGN PATENT DOCUMENTS

WO          WO 00 58356 A1    10/2000

OTHER PUBLICATIONS

Database GenBank Accession No. EO3861. Sep. 1997.

*Primary Examiner*—Larry R. Helms
*Assistant Examiner*—Stephen L. Rawlings
(74) *Attorney, Agent, or Firm*—Celera Genomics; Justin D. Karjala

(57) ABSTRACT

The present invention provides amino acid sequences of polypeptides that are encoded by genes within the human genome, the Ras-like protein polypeptides of the present invention. The present invention specifically provides isolated polypeptide and nucleic acid molecules, methods of identifying orthologs and paralogs of the Ras-like protein polypeptides, and methods of identifying modulators of the Ras-like protein polypeptides.

9 Claims, 26 Drawing Sheets

```
   1 AAGCGATAGC TGAGTGCGGC GGCTGCTGAT TGTGTTCTAG GGGACGGAGT
  51 AGGGGAAGAC GTTTGCTCTC CCGGAACAGC CTATCTCATT CCTTTCTTTC
 101 GATTACCCGT GGCGCGGAGA GTCAGGGCGG CGGCTGCGGC AGCAAGGGCG
 151 GCGGTGGCGG CGGCGGCAGC TGCAGTGACA TGTCCAGCAT GAATCCCGAA
 201 TATGATTATT TATTCAAGTT ACTTCTGATT GGCGACTCAG GGGTTGGAAA
 251 GTCTTGCCTT CTTCTTAGGT TTGCAGATGA TACATATACA GAAAGCTACA
 301 TCAGCACAAT TGGTGTGGAT TTCAAAATAA GAACTATAGA GTTAGACGGG
 351 AAAACAATCA AGCTTCAAAT AGAGTCCTTC AATAATGTTA AACAGTGGCT
 401 GCAGGAAATA GATCGTTATG CCAGTGAAAA TGTCAACAAA TTGTTGGTAG
 451 GGAACAAATG TGATCTGACC ACAAAGAAAG TAGTAGACTA CACAACAGCG
 501 AAGGAATTTG CTGATTCCCT TGGAATTCCG TTTTTGGAAA CCAGTGCTAA
 551 GAATGCAACG AATGTAGAAC AGTCTTTCAT GACGATGGCA GCTGAGATTA
 601 AAAAGCGAAT GGGTCCCGGA GCAACAGCTG GTGGTGCTGA GAAGTCCAAT
 651 GTTAAAATTC AGAGCACTCC AGTCAAGCAG TCAGGTGGAG GTTGCTGCTA
 701 AAATTTGCCT CCATCCTTTT CTCACAGCAA TGAATTTGCA ATCTGAACCC
 751 AAGTGAAAAA ACAAAATTGC CTGAATTGTA CTGTATGTAG CTGCACTACA
 801 ACAGATTCTT ACCGTCTCCA CAAAGGTCAG AGATTGTAAA TGGTCAATAC
 851 TGACTTTTTT TTTATTCCCT TGACTCAAGA CAGCTAACTT CATTTTCAGA
 901 ACTGTTTTAA ACCTTTGTGT GCTGGTTTAT AAAATAATGT GTGTAATCCT
 951 TGTTGCTTTC CTGATACCAG ACTGTTTCCC GTGGTTGGTT AGAATATATT
1001 TTGTTTTGAT GTTTATATTG GCATGTTTAG ATGTCAGGTT TAGTCTTCTG
1051 AAGATGAAGT TCAGCCATTT TGTATCAAAC AGCACAAGCA GTGTCTGTCA
1101 CTTTCCATGC ATAAAGTTTA GTGAGATGTT ATATGTAAGA TCTGATTTGC
1151 TAGTTCTTCC TTGTAGAGTT ATAAATGGAA AGATTACACT ATCTGATTAA
1201 TAGTTTCTTC ATACTCTGCA TATAATTTGT GGCTGCAGAA TATTGTAATT
1251 TGTTGCACAC TATGTAACAA AACAACTGAA GATATGTTTA ATAAATATTG
1301 TACTTATTGG AAGTAAAAAA AAAAAAAAAA AAAAAAAAAA AAAAAAAAAA
1351 AAAAAAAAAA AAAAAAAAAA AAAAAAAAAA AAAAAAAAAA AAAAAAAAAA
1401 AAAAA  (SEQ ID NO:1)
```

FEATURES:
5'UTR:           1-179
Start Codon:     180
Stop Codon:      699
3'UTR:           702

Homologous proteins:
Top 10 BLAST Hits

|  | Score | E |
|---|---|---|
| CRA\|108000024647144 /altid=gi\|12728868 /def=ref\|XP_002675.2\| RA... | 372 | e-102 |
| CRA\|18000004923424 /altid=gi\|4758988 /def=ref\|NP_004152.1\| RAB1... | 332 | 5e-90 |
| CRA\|18000004937406 /altid=gi\|131787 /def=sp\|P05711\|RB1A_RAT RAS... | 328 | 1e-88 |
| CRA\|18000004952860 /altid=gi\|131785 /def=sp\|P22125\|RAB1_DISOM R... | 320 | 3e-86 |
| CRA\|18000004995539 /altid=gi\|103720 /def=pir\|\|D38625 GTP-bindin... | 313 | 3e-84 |
| CRA\|18000004967528 /altid=gi\|92339 /def=pir\|\|S06147 GTP-binding... | 297 | 2e-79 |
| CRA\|18000004880958 /altid=gi\|464524 /def=sp\|Q05974\|RAB1_LYMST R... | 282 | 9e-75 |
| CRA\|18000004908714 /altid=gi\|466171 /def=sp\|P33723\|YPT1_NEUCR G... | 253 | 3e-66 |
| CRA\|18000005175724 /altid=gi\|7497231 /def=pir\|\|T33781 hypotheti... | 253 | 4e-66 |
| CRA\|335001098696672 /altid=gi\|11558649 /def=emb\|CAC17833.1\| (AJ... | 251 | 2e-65 |

FIGURE 1A

BLAST dbEST hits:

```
                                              Score    E
gi|12867866  /dataset=dbest  /taxon=960...     654    0.0
gi|12097820  /dataset=dbest  /taxon=96...      654    0.0
gi|12793758  /dataset=dbest  /taxon=960...     624    e-177
gi|12338056  /dataset=dbest  /taxon=96...      622    e-176
gi|11977068  /dataset=dbest  /taxon=96...      609    e-172
gi|10339840  /dataset=dbest  /taxon=960...     517    e-145
gi|10349761  /dataset=dbest  /taxon=960...     436    e-120
gi|10997958  /dataset=dbest  /taxon=96...      385    e-105
gi|10996533  /dataset=dbest  /taxon=96...      381    e-103
```

EXPRESSION INFORMATION FOR MODULATORY USE:
library source:
From BLAST dbEST hits:
gi|12867866  Fetal brain
gi|12097820  Adrenal gland
gi|12793758  Brain neoroblastoma cell line
gi|12338056  Adrenal gland
gi|11977068  Skin melanotic melanoma
gi|10339840  Uterus leiomyosarcoma
gi|10349761  Skin melanotic melanoma
gi|10997958  Placenta
gi|10996533  Placenta From tissue screening panels:
Whole brain

FIGURE 1B

```
  1 MSSMNPEYDY LFKLLLIGDS GVGKSCLLLR PADDTYTESY ISTIGVDFKI
 51 RTIELDGKTI KLQIESFNNV KQWLQEIDRY ASENVNKLLV GNKCDLTTKK
101 VVDYTTAKEF ADSLGIPFLE TSAKNATNVE QSFMTMAAEI KKRMGPGATA
151 GGAEKSNVKI QSTPVKQSGG GCC   (SEQ ID NO:2)
```

FEATURES:
Functional domains and key regions:
[1] PDOC00001 PS00001 ASN_GLYCOSYLATION
N-glycosylation site 125-128 NATN   (SEQ ID NO:6)

[2] PDOC00005 PS00005 PKC_PHOSPHO_SITE
Protein kinase C phosphorylation site

```
Number of matches: 5
      1      59-61  TIK
      2      97-99  TTK
      3     98-100  TKK
      4    106-108  TAK
      5    122-124  SAK
```

[3] PDOC00006 PS00006 CK2_PHOSPHO_SITE
Casein kinase II phosphorylation site

```
Number of matches: 3
      1      35-38  TYTE   (SEQ ID NO:7)
      2    106-109  TAKE   (SEQ ID NO:8)
      3    127-130  TNVE   (SEQ ID NO:9)
```

[4] PDOC00007 PS00007 TYR_PHOSPHO_SITE
Tyrosine kinase phosphorylation site 30-36 RFADDTY   (SEQ ID NO:10)

[5] PDOC00008 PS00008 MYRISTYL
N-myristoylation site

```
Number of matches: 3
      1     21-26   GVGKSC   (SEQ ID NO:11)
      2    147-152  GATAGG   (SEQ ID NO:12)
      3    152-157  GAEKSN   (SEQ ID NO:13)
```

[6] PDOC00017 PS00017 ATP_GTP_A
ATP/GTP-binding site motif A (P-loop)

18-25 GDSGVGKS   (SEQ ID NO:14)

[7] PDOC00579 PS00675 SIGMA54_INTERACT_1
Sigma-54 interaction domain ATP-binding region A signature 14-27 LLLIGDSGVGKSCL   (SEQ ID NO:15)

FIGURE 2A

BLAST Alignment to Top Hit:
>CRA|108000024647144 /altid=gi|12728868 /def=ref|XP_002675.2| RAB1,
    member RAS oncogene family [Homo sapiens] /org=Homo
    sapiens /taxon=9606 /dataset=nraa /length=222
    Length = 222

Score = 372 bits (944), Expect = e-102
Identities = 190/222 (85%), Positives = 190/222 (85%), Gaps = 32/222 (14%)
Frame = +3

```
Query: 129 GGCGSKGGGGGGGSCSDMSSMNPEYDYLFKLLLIGDSGVGKSCLLLRFADDTYTESYIST 308
           GGCGSKGGGGGGGSCSDMSSMNPEYDYLFKLLLIGDSGVGKSCLLLRFADDTYTESYIST
Sbjct:   1 GGCGSKGGGGGGGSCSDMSSMNPEYDYLFKLLLIGDSGVGKSCLLLRFADDTYTESYIST  60

Query: 309 IGVDFKIRTIELDGKTIKLQI-----------------------------ESFNNVK 392
           IGVDFKIRTIELDGKTIKLQI                             ESFNNVK
Sbjct:  61 IGVDFKIRTIELDGKTIKLQIWDTAGQERFRTITSSYYRGAHGIIVVYDVTDQESFNNVK 120

Query: 393 QWLQEIDRYASENVNKLLVGNKCDLTTKKVVDYTTAKEFADSLGIPFLETSAKNATNVEQ 572
           QWLQEIDRYASENVNKLLVGNKCDLTTKKVVDYTTAKEFADSLGIPFLETSAKNATNVEQ
Sbjct: 121 QWLQEIDRYASENVNKLLVGNKCDLTTKKVVDYTTAKEFADSLGIPFLETSAKNATNVEQ 180

Query: 573 SFMTMAAEIKKRMGPGATAGGAEKSNVKIQSTPVKQSGGGCC 698  (SEQ ID NO:5)
           SFMTMAAEIKKRMGPGATAGGAEKSNVKIQSTPVKQSGGGCC
Sbjct: 181 SFMTMAAEIKKRMGPGATAGGAEKSNVKIQSTPVKQSGGGCC 222  (SEQ ID NO:4)
```

Hmmer search results (Pfam):

| Model | Description | Score | E-value | N |
|---|---|---|---|---|
| PF00071 | Ras family | 256.4 | 7.7e-75 | 2 |
| CE00060 | CE00060 rab_ras_like | 170.0 | 3.9e-47 | 2 |
| PF00634 | BRCA2 repeat. | 9.9 | 0.39 | 1 |
| PF00056 | lactate/malate dehydrogenase | 3.9 | 3.4 | 1 |

Parsed for domains:

| Model | Domain | seq-f | seq-t | hmm-f | hmm-t | | score | E-value |
|---|---|---|---|---|---|---|---|---|
| PF00056 | 1/1 | 13 | 29 | .. | 1 | 18 [. | 3.9 | 3.4 |
| CE00060 | 1/2 | 8 | 64 | .. | 20 | 77 .. | 86.8 | 8.9e-23 |
| PF00071 | 1/2 | 13 | 64 | .. | 1 | 52 [. | 111.9 | 4.8e-32 |
| PF00634 | 1/1 | 57 | 79 | .. | 13 | 35 .] | 9.9 | 0.39 |
| CE00060 | 2/2 | 65 | 140 | .. | 110 | 188 .. | 81.2 | 2.9e-21 |
| PF00071 | 2/2 | 65 | 173 | .] | 85 | 198 .] | 142.4 | 4.5e-41 |

FIGURE 2B

```
   1 TTTGGGTGT GTGTGTGTGT GTGTGTGTGT GTGCCTTTAC TAGTGACTCA
  51 GGTCACAGTT TTCTGAGATT TTTTTTCTCC CCTCAAGACA GAATCTTGCT
 101 CTGTCGCCCA GGCTGGAGTG CAGTGGCCTC TCGGCCCACT GTAGCCTCCG
 151 CCTCCCGGGT TCAAGCAATT TTCCTGCCTC AGCCTCCCGA GTAGCTGGGA
 201 TTACAGGCAC GCGCCACCAT GCCTGGCTAA TTTTTGTATT TTTAGTAGAG
 251 ACAGTGTTTC ACCATGTTGG CCAGGCTGGT CTTGAATTCC TGACCTCGTG
 301 ATCTGTCCGT TTTGGCCTCT CAAATTCCTG AGATTACAGG CATGAGCCAC
 351 CGAGCCTGGC CAGTTTTCTG AGTTTTTATT TGAAATCAAA ATAAGCTTTT
 401 TTTTTTTTTT TAATGGGCTT TAGAGTCCAG GGTAACGAAC ACTTTTTGGT
 451 GCCTATTACT GAACCATTCA GGGTATTCCT GGGGTGGTGA CCGTGTTCAT
 501 TTCAGAAACC AACATGTTCA TTTCAGAAAC CAAACTCGGG TAACTTTTGA
 551 TAAGTTCATC AACTAAGGCC CATGGCAGAA TTTGAGGGCT AAGGGGTGTA
 601 ATTAGTGTAT GGGTAGAAAT AAGTGCCTTC TTTCTATATT TTGGCGTTGT
 651 AGGAATTTAA AGTGATTCTG CAGTAAGTCT CAGGAGACAA TTTTCTTAGT
 701 TCTTAGAAGT TGGAAGATAA ACTTTGGACA ATGTATTACA CTATGCCCTT
 751 TGTAATTAAA TAACTCAAGA TAATGTGTTA AAGTTTAGCG GAGATTTAAA
 801 TTCCTGAGCT GATTAAAGAG AGCTGTTAAG GCCATAGGTT TTTTAAAAAT
 851 GAGTTAATAT TACTCCCAGA AATTGTAGGC ACTATATAGT GATGAATTGC
 901 ATATTTTTAT TGCTTATTAT TTTCCAGTCT TGCAGAATGG CTCAGGGTTA
 951 GTAGCAACTA AAAGATAATA CATTACAATT CAACCTGAAG GCCGGGACGA
1001 AGGTAGGAAT TGGATTTTAG GCTGGCTCTG GGCTGTGTCC CTCCCATCCA
1051 TGGGATGTGG AGCCATTGAA GGTTGTGGGG TCACGATGCA GGTGCTGTCT
1101 CAGAAAGATA CATCCGACTG TGTGTGCAAA TGGGCTGGGG CGGAGAAGAG
1151 AGAGAGAGGT AGAGTCCATT TGGAGACTAC TGCAATAGCC AGGCTGACGA
1201 GTTAAGAGCG GGGCACAGTA AGAATGGGAA GAAATCTAAG AAGAAAATGG
1251 TAGTGCGCGG GGCCAACAAT GGACGATGAC CGAACCCAGG TGGGGATGGG
1301 TGAGTGACGA GAAGAACCGC TCCGTGCCGT CCAGGGAGCC CCTTGACTTC
1351 CCTTCTGTTC TTAGAGCGGA CGTCCTCCTA CCAGCCCCCA ACCAGCGCCA
1401 CCAGGGTGGC GCAAGCCTCA AGCTGGTCAG GTCAGCAACA GCCGCAACGG
1451 AGGCAGGAGC CGACACGCTC GTACCCCGGC CCCCTCCCCG CCCCCGCACC
1501 CCCGGCAGTC CCTCCGGTTT GACCACTCCC CCCGGTCCCT TGCCTCCCCC
1551 GACCCCAGC CTCCGTCGGC CGCCGGCACC ACCCTCCGCC CCTCTCCGCC
1601 CCCTCCCCCG TGGGGCGCTG ACTCGCCCGG CTGCCACGTC TCACTGATGA
1651 CATCACTAGG GCAGCTCGGC CTTAGCCAAT CCGCCAGGGG GAGTCCGAGC
1701 GAAGTCCTAG CCAGCGAGTC AGAGGGGAGG GGAGCAGGGA GGGGCCGAGG
1751 GTGGGGAGGT GAGGGAGTGG GGAATGGGGC GGGCGACAAC CCTTCAGGTA
1801 CGCATGCCCC AGAGGCGCGG CGCTTGGCGG GAAGCTGAGT CCTGGCCTTG
1851 CGTCGCACTG TCTGTCCTCA GCTCGCGTAG CCGCGCTCGC GACTCCCTTT
1901 CCCGGCATGC CAGGCGGTGC GGCCGCCCTC TGGGCCGTGT AAAGGCCCCT
1951 CGGTCTAAGG CTTCCCTATT TCCTGGTTCG CCGGCGGCCA TTTTGGGTGG
2001 AAGCGATAGC TGAGTGGCGG CGGCTGCTGA TTGTGTTCTA GGGGACGGAG
2051 TAGGGGAAGA CGTTTGCTCT CCCGGAACAG CCTATCTCAT TCCTTTCTTT
2101 CGATTACCCG TGGCGCGGAG AGTCAGGGCG GCGGCTGCGG CAGCAAGGGC
2151 GGCGGTGGCG GCGGCGGCAG CTGCAGTGAC ATGTCCAGCA TGAATCCCGA
2201 ATAGTGAGTT CAGGAGAGCA CCGGTCGGCT GGGTCCGTGG GCCAGCTTGG
2251 GGGATCTTAA AGGGGTCGAG GAGGGTTGGG GCAGAAGTCG GGGCATCGGC
2301 TGGGGTGAGG CGAGGGTGAT GGGTCAGGAG AGGCTGGCGG CCGGGAGTCG
2351 GGCCCCATTG TCTGACGCGG AGGGCGGCC GCGCGGGGA GGGGTCGGGC
2401 CGGAGGGGTG AGCCGCCCGG GCCTGGACCG GGTCAGGTTA GAGGGCCTGA
2451 CTGCGGGGCG GGTGCTGAGG AAGCCTGCCG AGGGGCCTGG GGCGGTGTGA
2501 AGGGGTATCT TCTCTCGGAG GCAGTGACTT TGAAGGAGG ACTTGTCTCT
2551 AAGGGGAGGG GATGGGGTGG GAGAGCCCTT CTAGAGGGCA CTGTCAGACC
2601 CTGCGCCCGC ACTCTGCGGA GCTGTCAGGA TCTTCGGGGT AGAAACCAGC
2651 TTTACTTGTA AATCCTGAGC TTGTTGGGTC TCTCTCCTTC CATCCTCCCC
2701 GCCAGGTTTC AGGTAATATG GATGCTTTTC GGGACTGCGT GGGATTGAGG
2751 GGAATGAGTA GATGGTGAGA AGCAACTGAA CATTTATTAG TTCTCTTTTT
2801 GAGTTGTGTC TTGGAGGAGT TGTTTAAGAG CTCGCCGGGT CCATTGCCCT
2851 CCTATAAAAA CCTGGGCATT TGTGAGAATT TGTTTTTTTT TTTTTTTAAA
2901 GAGGACACCT AAGTCATTTT GTCTTCTGTG GGTCAAGGGA AAAAAAAAAA
2951 ACTAAAGCCA AGAAATGTCT TTTTGATACT CGCAGATTAA AGGAAGCTTG
```

FIGURE 3A

```
3001 CTGTCAAGTT GAAAGAGAAA CGAACGGGAC CTATGATAGA TCTGTATGTA
3051 GGTTTTGGAT TACCTGCTTG GATGCTTGCA GATAGGGAAT GAGGTTCCAT
3101 GACGTGTCAT GAAAAGTTAA TGCATTTCTT TTTCTTGCTT ACTCAAGAAG
3151 TCACCACAGC AGATGTGACA CACCTGGCAC CTTTCCTGGG AACTGGTGTT
3201 CACTTCCCTT GGGTAGAGTT TGTTGGGCTC TCCTCAATGG CCCTTTAAAA
3251 ATTTCCTCTA CAGTTTACAT GCATGTAAAG TAATGAATAA TTGGAAGAGA
3301 CCGAATTGGT ATTCCTTTTC AGTGTCAAAG GCCTTTGAGG GATGGGGGAA
3351 AATCAGTATT TGTTGTAAAA GTTGAGTTTA TTTGCTGGTT TGGTCAATTA
3401 CTGCTAGACA TTTTCCCCTA AAAGGTCCAC CCACCAGTTT AGCTGACTGT
3451 CATATGTGTG TCACATGGCT CTTGCAAAAT GCTTACAAGT TTTGTAATAG
3501 TGTGGCTTGA AGCTGAAATC TTTTGCACTA AACAGAAACC GTAGTATTTT
3551 ATTAGAATTT CATGCTTTAG AAGTTGAGGG TAGTGTTCTT GTAGTGACAT
3601 TTGCTGTGTT GACAGTTTAA AAAAATTTTT TTTTCAAGGG CTCCAAGGAC
3651 AAAGTTGGTT TTGCACAGTT GAACGGAGGT GAACTTGAGG TTCTTAATTT
3701 AGTAGTTTTC TTGGTAACAA TAAAGAACAT GGATTTACTG CTTTATCGAG
3751 GTTTATAGAC CTCTACTGTT CAGGAAATTT TCTGAATTTG CTATATATAT
3801 GTTTATTAGT GTAAATAAAT CTTCAAGATT AGTTGAGAAC TTTGACAAGT
3851 TACTCAGCCT CTGAATTTTT TTTCCCTTTT GTAAAATAGG ATAATTGGAG
3901 TCATTATTCC TGTCAGGGTA GTGGTGAAAT TCAAATGTAT ATAAAAGAAT
3951 TTGAAAAACT GTGTGAGCAT TCTTCAGGTG GTATGCATCA TTTTCATGAA
4001 AGGCATTCTA TTAGTACCAG GATTTAGGAA TATAATCCTT GCGCTTAAGA
4051 AGTTTAGATA TAGGCCAGGC GCGGTGGCTC ACCTCAGTAA TCCCAGCACT
4101 TTGGGAGGCC GAGGCGGGCG GATCCCGAGG TCAGGAGATC GAGACCATCC
4151 TCGGTAACAC GGTGAAACCC CGTCTCTACT AAAAATGCAA AAAATTAGC
4201 CGGGCGTGGT GGTGGGCACC TGTAGTCCCA GCTACTCGAG AGGCTGAGGC
4251 AGGAGAATGG CGTGATCCCG GGAGGTGGAG CTTGCAGTGA ACCAAGATCT
4301 GGCCACTGCA CTCCAGCCTG GACGACAGAG CAAGACTCCG TCTCAAAAAA
4351 AAAATTATTT ATTGTTTTGA GACGGAGTTT CAATCTTGTT GCCCAGGCTG
4401 GAGTGCAATG GCGCAAATCT CCTCTCACCG CCACCTCCGC CTCCTGGGTT
4451 CAAGTGATTC TCCTGCCTCA GATTCCCGAG AAGTTGGGAT TACAGGCATG
4501 TGCCACCACT CCCGGCTAAT TTTGTATTTT TGGTAGAGAC GGGGTTTCTC
4551 CATGTTGGTC AGGCTGGTCT CAAACTCCCG AAGTGATCCG CCCGCCTCAG
4601 CTTCCCAAAG TGTTGGGATT ACAGGCGTGA GCCACCGCGC CCGGCAGAAA
4651 TAGATTTTAT ACATGTCAAA TACCAGTAGA TATAGCAAAT TCCAGATGTG
4701 TGGCATGGAT GAGAGCAACA AGATTTCAGG GGGATGGTGG GTTGTGGTTG
4751 GCTATCTGGG TTTTGGAAGA CTTTATAGAA GAGAGACCTG AAAGGGATTT
4801 ATCAGCAATT AGATTTGGAG GAACAGAGGG AGTGACTAGG AATTTTCAAG
4851 GGGGAGAAGA AGGAGGAATG GCTCATAAAT GACAAGGACA GTAATAAGTA
4901 AATACGGTGT CAAATCATCC TTTCTTTTGA AGACTAATGA CCTCAAAGGG
4951 ATCAAACCCA GAAACAGTTT TTATATTTTT TCTGGGATCA AATACATGGG
5001 TATCTGGCCT ACTATATTTG TATTCTAGAC TGTTTAGTAA AATAATACAG
5051 GAATTTGAGA AAACCTTTGC AAAAGTGTTA GTGAAAATTA CTTAGGGTGA
5101 GAGGAAGTGA GGGATATTTT ATTAGGGGAG GTCACAAGGG CAGTGAGCAA
5151 TCAGATTTTT AGTAATCTGA CTTAAGCAGT TTCTTTTTGT TTTAATGAAG
5201 CTTGTTATCT TTATAAAAGT AATTAGAGAA AATTTGGAAA ATAAAGGAAA
5251 GAAAGAAAAG TTCTTTAGTG TTTTATCACG CAAATACAAG CTCATTCGTT
5301 TTTAACATCT TGTTCCAAAC TCCAAAGTCT TGCTTTCTCT TCAATTAAAA
5351 CTTTAATGGG TGGATGCTTT TCCTGCTTCC AGTATGTTAT CTTAATAACT
5401 AACAATGGTA TATTAGCTAA TGTTTACAAA TGTACTCCAG ATGTTCCTTA
5451 AGTTACTTTG GTTTATCATT ACCAATTTAT ATTGTTTCTT TTAGAAATTT
5501 ATAATCTTTG TTAATGGGTT CTGCTAAATT TGGTAGTGAA AATGGGATCT
5551 TGAGAAAAAA GATTCTGAAG CAACAGAATT TTTAGATTTA TATTGGTTTA
5601 CATAAGAGTT GGTAGCTGTA TTACTTTTTT TGTTTGTTTT GTTTTTTTTT
5651 TGAGACGGAA TCTTGCTCTG TCGCCCAGGC CTTGGCCTCC CAAAGTGTTG
5701 GGATTACAGG CGTGAGCCAC TGTGCCTGGC TGTTTGTGTT TTTTTTGTT
5751 TTTGTTTTCT TTTCTTTTTC TTTTTTTCGA GATGGAGTCT CACTCTGTCA
5801 CCCAGGCTGG AGTGCAGTGG CGCGATCTTG GCTCACTGCA ATCTCTGCCT
5851 CCTGGGTTCA AGCGATTTTC CTGCCTTGGT CTCCTGAGTA GCTGGGATTA
5901 CAGGCATTTG CCACCATAAC CAGCTAATTT TTGTATAGAG TACCCAGCCA
5951 TCTCTAATGT TGATCAGGCT GAAGCAGGTG GATCACCTAA GGTCAGGAGT
```

FIGURE 3B

```
6001 TCAAGACCAG CCTGGCCAAT ATGGCAAAAC CCTATCTCTA CTAATACAGA
6051 AAATTATCTG GGTGTGTTGG CTGGCGCCTG TAATCCCAGC TACTCGGGAG
6101 GCTGAGGCAG GACAATCTCT TGAACCTCGG AGGTGGAGGT TGCAGTGAGC
6151 CGAGATCACA CCATTGCACT CCAGCCTGGG CAACAGAGCA AGACTTGTCT
6201 CAAAAAAAAA AAAAAAAAA AAAAAAGGC AATTGAAAGT GTAATCTGAA
6251 CAGTTAAAAA AGTAGATAGA AAGGGTTAAA GCTTTTTTTT GAGGATCTGA
6301 AGAAAAATGT GGATTTTTTT TGAGCTACGT TTTGAAGCAG GCAGTGATTA
6351 TTTCAGCACA TTAAGAAATG CTTAACATGG CCAGGCGCAG TGGCTCACGC
6401 CTGTAATTCT CAGCACTTTG GGAGGCCGAG GTGGGCGGAT CATTTGAGGT
6451 CATGACCAGC CTGGCCAACA TGATGAGACA CTGCCTCTAC TAAAAATACA
6501 AAAATTAGCT GGGTGTGGTG GTGCACGCCT GTAATTCCAG CTACTCAGGA
6551 ACCTGAGGCA GGAGAGTCAC TTGAACCTGG GAGGCGGAGG CTGCAGTGAG
6601 TCCAGATCAT GCCACTGCAC TCCAGCCTGA GGGACAGAGT GAGACTCCTC
6651 AAAAAAAAAA AAAAAAAAG AAAGAAATAC TTAACATTAT TCTCGTGATT
6701 ATTCTCATAA CATTTTTCAT AATCCACTGG CTTCCAGTGG ATTTTTTTAG
6751 TGTCAAGAAA ATAATTTTGA TTGGTTCATC TTTAAGGAAT GTGTTAAGAA
6801 TAAAGCATGT CTACCTGTCT TCAGTATACC AGCTAACTAT AGTAGGAAGA
6851 AATATAGTAG TCTACTTAGA TCAACTATAA TTCTTTAATG CAGAAAAAGT
6901 TTAAAGTATT TACCTTATTT TTAGCCCCCA TCCCCTTAAG TATATCATGG
6951 CTCCAGAATC TCTGAAAATG TTATCAGTCT TTCAGACTTT GCTCTTCTTT
7001 CATGTTATAC TCAAGAAACA TTTGACCTTT TTTTTTTTTT TTTTGCTTGC
7051 ATTGTGTTTC AAATAATTTT TAACAAAACT TAAGTGTTTG AAAGTGAAAG
7101 CAGGTTGTCT TTGTGACTTT TGGTGGTGGT TTGAAAAACT CAGAAAAGTT
7151 TAAAGAAGAA AGATAACTAG TATTCTCATT GTCCAGAATA TGATTTTTTA
7201 AATGTCTATA GAATATCACC ATCTGTAATT CTTCCGGTAA TTTAAGTATT
7251 CAGTAGTTGT ATAAAACCTT TAAAATATAT ATATTGAGAA TTTTGTGTGA
7301 ATGAGATGAT GAGATAATCT TGTAGGATCA TTTAAAGATA AGAACTGAGG
7351 CCTGGCACAG TGGCTCATGC CTATAATCAC AGCACTTTGG GAGGCCCAGG
7401 CGGTAGATCA CCTGAGGTCA GGAGTTTGAG ACCAGCCTGG CCAACATGGC
7451 AAAACCCTGT CTCTACTAAG CATAGAAAAA TTAATTGGGT GTGGTCGTGC
7501 CTGCGTGTAG TCCCAGCTGC TTGGGAAGCT GAGGCGGGAG AATCTCTTGA
7551 ACCCTGGAGG TGGGCATTGC AGTGAGCTGA GATTGCGCCA CTGCACTCCA
7601 GCCTGGGCGA CAGAGCAAGA CTCTGTCTCA AAATAAAGTA AAATAAAATG
7651 AAGATAACAA CTGAAATTTC ACATTAAAAA TTTTTTTGTA GCGACTGTGC
7701 CTCCTATGTT GTGCAGGCTG GTCTCAAACT CCTGGCCTCA AGCGATCCTT
7751 CCAAAGCACT GGGTGGGCCA CCATGTCCAG CCTGAAATTT TGCATTAAAA
7801 AATTTCCCGC TTTTGGCTGG GCGAGGTGTC TCACGCCTGT AATAGCAGTT
7851 TGGGAGGCCG AGGCAGGCAG ATCACTTGAG GTCAGTTCTA GACCGGCCTG
7901 GCCAATGTGG TGAAACCCTG CCTCTACTAA AAACACCAAA TTAGCTAGGC
7951 GTGGTGGTGT GCGCTTGTAG TCCCAAGCTA CTGAGGAGGC TGAGACAAGA
8001 GAATCGCTTG AATCTGGGAA AAAGAGGTTG CCGTGAGCCA AGATTGGCCA
8051 CTGCACTCCA GCCTGGGTGA CAGAGTGAGA TTCTGTCTCA AAAAAATAAA
8101 AAATAAAAAT TTCCCCCTTT AATCAAATTA AGTTAAAATG AGGGATGTTA
8151 GACAGTTTTT AACCATCAAA TATTTAGTT TAGTTTTTTT TTTTTAACGT
8201 TGTCTTAAAG ATGGAAGTGC TTCAAAATCA AATCTTCCTT GCCAGTTCTC
8251 TACTTGGCTT CTTTTTTTTT CTTTTGAGA TAGAGTCTCA CTTTGTCACT
8301 GGAGTGCGTT GGCGTGATCT CGGCTCACTG CAACCTCCGC CTTCCAGGTT
8351 TAAGTGATTC TTCCACCTCA GCCTCTCAAG TAGCTGGGAG TACAGGTGTG
8401 TGCCACCACA CCCGGCTAAT TTTTGTAGTT TTAGTAGAGA CAGGGTTTCA
8451 CTATGTTGGC CAGGCTGGCC TCAAACTCCT GACCTCGTGA TCCACCCACC
8501 TCAGCCAAAT TGCTGGGATT ACTTGTGTGA GCCACGCGCC TGGCTTCTAC
8551 TTGGCTTTTA AAGGGAATTT TGCTTTCTGA GTAATTTTAT TTCTCAGGTA
8601 TCTTGGTCTT TTTAATTCTG GAAGCAATCT TAATAATTTA TGTATGTGCC
8651 CTGTAATCCC AGCACTTTGG GAGGCCGAGG TGGGCGAATC ACGAGGTCAG
8701 GAGATCGAGA CCATCCTGGC TAACACGGTG AAACCCCATC TACTAAAAAT
8751 ACAAAAAATT AGCTGGGCGT GGTGGCAGGC GCCTGTAGTC CCAGCTACTT
8801 NNNNNNNNNN NNNNNNNNNN NNNNNNNNNN NNNNNNNNNN NNNNNNNNNN
8851 NNNNNNNNNN NNNNNNNNNN NNNNNNNNNN NNNNNNNNNN NNNNNNNNNN
8901 NNNNNNNNNN NNNNNNNNNN NNNNNNNNNN NNNNNNNNNN NNNNNNNNNN
8951 NNNNNNNNNN NNNNNNNNNN NNNNNNNNNN NNNNNNNNNN NNNNNNNNNN
```

FIGURE 3C

```
9001 NNNNNNNNNN NNNNNNNNNN NNNNNNNNNN NNNNNNNNNN NNNNNNNNNN
9051 NNNNNNNNNN NNNNNNNNNN NNNNNNNNNN NNNNNNNNNN NNNNNNNNNN
9101 NNNNNNNNNN NNNNNNNNNN NNNNNNNNNN NNNNNNNNNN NNNNNNNNNN
9151 NNNNNNNNNN NNNNNNNNNN NNNNNNNNNN NNNNNNNNNN NNNNNNNNNN
9201 NNNNNNNNNN NNNNNNNNNN NNNNNNNNNN NNNNNNNNNN NNNNNNNNNN
9251 NNNNNNNNNN NNNNNNNNNN NNNNNNNNNN NNNNNNNNNN NNNNNNNNNN
9301 NNNNNNNNNN NNNNNNNNNN NNNNNNNNNN NNNNNNNNNN NNNNNNNNNN
9351 NNNNNNNNNN NNNNNNNNNN NNNNNNNNNN NNNNNNNNNN NNNNNNNNNN
9401 NNNNNNNNNN NNNNNNNNNN NNNNNNNNNN NNNNNNNNNN NNNNNNNNNN
9451 NNNNNNNNNN NNNNNNNNNN NNNNNNNNNN NNNNNNNNNN NNNNNNNNNN
9501 NNNNNNNNNN NNNNNNNNNN NNNNNNNNNN NNNNNNNNNN NNNNNNNNNN
9551 NNNNNNNNNN NNNNNNNNNN NNNNNNNNNN NNNNNNNNNN NNNNNNNNNN
9601 NNNNNNNNNN NNNNNNNNNN NNNNNNNNNN NNNNNNNNNN NNNNNNNNNN
9651 NNNNNNNNNN NNNNNNNNNN NNNNNNNNNN NNNNNNNNNN NNNNNNNNNN
9701 NNNNNNNNNN NNNNNNNNNN NNNNNNNNNN NNNNNNNNNN NNNNNNNNNN
9751 NNNNNNNNNN NNNNNNNNNN NNNNNNNNNN NNNNNNNNNN NNNNNNNNNN
9801 NNNNNNNNNN NNNNNNNNNN NNNNNNNNNN NNNNNNNNNN NNNNNNNNNN
9851 NNNNNNNNNN NNCCAGGCTG GAGTGCAGTG GCACAATCTT GGCTTACTGC
9901 AACCTCTGTC TCCCGGGTTC CAGCATTTCT TCTGCCTCAG CCTCCTGAGT
9951 AACTGGGACT ACAGGCGTCC ACCACCACGG CCAGCTAATT TTTATATTAG
10001 TAGAGATGGG GTTTCACCAT GTTGGCCAGG CTGGTCTCCA ACTCCTGACC
10051 TCAGGTGATC CGCCTGCCTT GGTCTCCCAA AGTGCTAGGA TTACAGGCGT
10101 GAGCCACTAC GTTTGGCTGC TTATCAGCTT TTTACCACTT TGTCGCCACT
10151 ACATTTTGGA ATTTTCCTTT GAGAATTAGG CAAAATGCCC AGACTCCCCC
10201 CCGGCCCCCG CTTTAGAGGG AGAGGGGAGC AATTAGACTA TTCCTTTGTT
10251 TCCCTATAGA AGGTGGGGCT GAGATTACTG CTTTGATATC TGGAATGTAA
10301 TTTAGGGAAG AAAATTTAGG TCTTGGCCTT TCTTTGGAAC CACCCTGGGA
10351 GTGTTGCAGA TTATTAATAG GGTAATGGTG GAATGATATT CAGGGGAAAA
10401 ATGGTCCTGA GGAGCCAGAG AACTAAGTGT TAGTTTGTTG GCTGACTGAA
10451 ACATGTGAGA GATAGGGTAC AGAAGAAGTA GGAAATAGTT TTCCTTGGTA
10501 CTTCTGTGAC AGGTTGGCTC AATTGGCTGG AACACCCTAC ACTGCTTTAT
10551 TAAATCCAAG GTTGTGATAG GTTCCAGTTA AGTTTACTGT GTTCTATGCT
10601 TGTAGATTTC CTAATTAGGA CAAGTAGTGT TAAATATGCA TGCCTTTATT
10651 CACAAGAGGG ACCATTCTTT TGGAAACATC ACTTTTTAAT AATACTAGGT
10701 GCTATTTAGC ACTTACTCGG TGCCAGCCAC GTGGCTATGG TTTTTTTTTT
10751 TTTTTTTTTT CGAGACATGA TCTAGCTCTG TCTCCCAGGC TGGAGTGGTG
10801 GTAGCACAGT CATGGCTCAC TGCAGTCTCA ACCTCCTGTA CTCTAGTGAT
10851 CCTCCTGTCT CAGCCTCCTG AGTAACTGGC ACCATGCCTG GCTAATTTTT
10901 TTTAAGAGAT GAGATGTCGC TATGTTGCCT ATGCTGGTCT CGAACACCTG
10951 GGCTCAAGTG ATCCTCCCCG CCTGAGCCTC TCAAAGTGTT GGGATTACAG
11001 GTGTGACCCA CCTCACTTGG CCATCTATGG TCTTTACATA GGGCATTTTG
11051 TGCAGTCTGC ATCTCAAACT AGTGATCTTC AACAGTGAAA CTCAGTGAAT
11101 TATGTAATTC ATGTTTTCCA AGAACAATGA TGGATTTAAT TTCTCTGAAT
11151 GTATTTCCTT TGTATAATAA TAGTACTTAA GTGGAATTAC TCTTTGTCCT
11201 TTCTACTCTC CTTATAGATA TTTTCTGGTA TCTTGATTTG GGACTGTTAC
11251 ATTTAACCCA TTTATCGTCG TGTAGCCATA CTCACGTTAC ATTTGATGCA
11301 TCTGCTCCCT TTGTGTCTAT ATACTCATAT AACATTTTGC ATAAAGTTAT
11351 AGGCAGTTCA CACCAAGGCT GTTCATGAAC CTCAGATTAA GAATACTTGA
11401 TTTAGGAGAT TGAAAACAGA AAAGAGAATG TTAACTATCA TTATCAATAT
11451 TAAAATGTGA AAATCTGAGA GTGACAAAGC TTAGCTTTAA ATCTGGTATC
11501 CCAAACTCAT TTGAGTTTTT TTTTTTTTTT TTTTTTTTTT GAGACAAGGT
11551 GTCGCTTTGT CCCCCAGGCT GGAGTGTAGT GGTGTGATCT TGGCTCACTG
11601 CAACCTCCAC CTCCCAGGTT CAAGTGATTC TCCTGCCTCA GCCTCTGAAG
11651 TTGCTGGGAT TACAGGCTGC GCCACCACGC CCAGCTAATT TTTGTATTT
11701 ATAGTAAAGA CGGAGTTTCA CCTTATTGGC CAGGCTGGTC TCAAACTCCT
11751 GATCTTGTGA TCCTCCCGCC TCGGCCTCCC AAAGTGCTGG GATTACAGGT
11801 GTGAGCCACT GTTCCCGGCC TAATTTGAGT TTTAAAATGT GGAGTTTAAG
11851 ATGTTAGTCT TAAAGTGGGT TAGATGAAAT TTATAAAAAT AGTCAAATAG
11901 CTAAATTTAT AAAAGGCCAT TTGAAACAAT TTTGTGAAAT ATATAATGTG
11951 GATAATTATG TAGTGCTTTA TGTGTAGATT GGTGGTTAGC ATCTGCCTGA
```

FIGURE 3D

```
12001 TGAAGAGCAG TTGGATTTCT TACTTACTAA AGCTAGTGAA ATCTGAACTC
12051 CAAATTAGGC ATCTTCACCA GGCTTTTTG AGCCGAGCTA ACTTACTCTC
12101 TTTTTATTT TTATTTTTA ATTAATTAAT TTTTTTTTT TTTTTTTTT
12151 TTTGGTAGAG ACAGGATCTC CCCATGTTAC CCAGGCTTGT CTCTGGCTCC
12201 TTGGCTCAAG CAGTCCTCCT ACCTTAGCCT CCCAAAGTGC TAGGATTACA
12251 GCTGTGAGCC ACTGCGCCAG GCTGAGCTTA TTCTCTACTA ACACAAGTGT
12301 TCTAATTTAA TTTAAGCAGT GAATCACACT TTTCTTTGTA TTTGGTCAGG
12351 TTCTGGGTGC TAGTTTATAT ATGATTTGAT TCATTCTGAT AGGGTTTTTT
12401 TGTTTTTTTT TGTTTTTGTT TTTTGTTTT TTTGAGACA GAGTCTAGCT
12451 CTGTCGCCCA GGCTGGAGTG TGGTGGCTCG ATTTCGGGTC ATTGCAACTT
12501 CTGCCTCCCA CCCAGGCTGG AGTGCAGTGG CTCGATTTCG GTCATTGCA
12551 ACCTCTGCCT CCCAGGTTCA AGCGATTCTC CTGCCTCAGC CTCCTGAGTA
12601 GCTGGGATTA CAAGCACCCA CCACCATGCC CGGCTAATTT TGTGTATTTT
12651 TAGTAGAGAC TGGGTTTCAC CATGTTGACC ACGCTGGTCT CGAACTCCTG
12701 ACCTCAGGTG ATCTGCCTGC CTTGGCCTCC CAAAGTGCTG GGATTACAGG
12751 TGTGAGCCAT CACACCAGGC CTCAAGAACT TTTTATTTTT GAGACAGGGT
12801 CTCACTCTGT CACCCAGGCT GGAGTACAGT GGTGAGATCA TGGCTTACTG
12851 CAGCCTGGAC TTCCCAGGCT CTGGTGATCC TCCCATCTCA GCCCCTGGAG
12901 TAATTAGGAA TATAGACACA CACCCATGCC TGGCAGTTTT TGTATTTTTT
12951 TTCTTTTTTC TCTTTTTTG TAGAGACTGG GTTCACATG TTGTATCAGG
13001 CTGGTTTTGA ACTCCTGAGC TCAAGCAATC CTCACTCTTT GACCTCCCAA
13051 CGTGCTGGGA TTACAGGCAT GAGCCACTGT ACCTGGCCTT TTCTACATTA
13101 AAAACTTTTT ATTAAAAAAC CCAAATCTTC CTTGTGGTTG TATATACATA
13151 TATACATAGG TACACACATG GAGAATTTTA CCTTGGAGGA AGGCTTGGTA
13201 AAGAAAATAG CCCTTTGGGC CGGGTGCGGG GGCTGACGCC TGTAGTCCTA
13251 GCACTTTGGG AGGCTGAGGT GGGCGGATTG CCTGAGCTCA GGAGTTCAAG
13301 ACCAGCCTGG GCAACACAGT GAAACCCTGT CTCTACTAAA ATACAAAAAA
13351 TCAGCTGGGT GTGGCAGCAT GTGCCTGTAG TCCCAGCTAC TTGGGAGCCT
13401 GAGGCAGGAG AACTGCTTGA ACCCGGGAGG CAGAGGTTGC AGTGAGCCGA
13451 GATTGTGCTA CTGCACTTCA GCCTGCGCGA CAGAGCAAAA CTCTGTCTCA
13501 AAAAAACAAA CAAACAAACA AAAAGGAAA ATAGCCTTTC TCTATCATCA
13551 GAGTATATTA AGAGTTGAGT TTTTTTTCT GTTTTTAAA ATTTTTGTTG
13601 TTTATTTTAA ATTACAAAAC ATGGACTCTG CTTACAAATT AAGAAAATGA
13651 CTCATGTTCA AACAAGCATA ATCAATATAA CAGTTAATAC AAGTTAAATA
13701 TTGTAATATG TTTACGGAAT AGCATGGCAA AATAGTGCAA AAGATTTGGG
13751 GAAGGGGCCT ATAATTTCTG TTAACAGAAA GTTTTAGTTA TGTTGATTCA
13801 ACTGGAGAGG AACAGAGCTC CCAGAAGGAC TCCAGAACAC TTGATGCTTG
13851 TCTGAGTGGG GTCAGCAGCA CTGAGTTCCC ACCAGCCAGA AAGTTTGTGT
13901 GTGTACATTA TTTCCCTTAA CTGCCACAAT AATCCCATGA AGAAAATGCC
13951 CTAGTTTTAC AAACAAGGAA ACAGAGGCAG AGAAGAGTTA AATGACTTGC
14001 CCAAGGGCAT TCAAAGTAAG CAACTGAATT GGAATTTTAA CTCAAAGGCT
14051 TGGATGTCCC ACTACAACAA ATAGGCTGTT TCTGCTTTAC TACATGTGCT
14101 TACTTCTAAG AATTTAACAT TTTAGGCTGG TTGTGGTGGC TCACTCCTGT
14151 AATCTCAGCA CTTTCGGAGG CTGAGGTGGG TAAATCACTT GAGCTCAGGA
14201 GTTTGAGACC AACCTGGGCA ACATGGTAAA ACCTCATCTC TACCAAAAAA
14251 AAAAAAAAA CTAGCTGGAC GTGGTGGCAC GCGCCTGTGG TCCCAGCTAC
14301 TCAGGAGGCT GAAGTAGGAG GATCGTTTGA GCCTGGGAGG TGGAGGTTGC
14351 AGTGAGCCCA CATTGCATCA CTGCACTCTA GCCTAGGTGA CAGAGTGAGA
14401 GCCTATCTCA CACACAAAAA AAAGAATTTA AAATTTTAGT CAAGTAATTA
14451 GGCACTAACA TTTTGTGGTC AGTTACTTTA CGAATTCATG GTTGGAGGCC
14501 TGATGTGGTG GCTCATGCCT GTAATCCCAG CACTTTGGGA GGCTGAGGCA
14551 GGAGGATTGC TTAAGGCCAA GAGTTCAAAT CAGCCTGAGC AACCTAGTAA
14601 GATCCCCTTT CTGCAAAAAA TTTAAAAATT AGCTGGGCAT GGTAGTGTGC
14651 ACCTGTAGTC CCAACCACTT GGGAGGCTGA GGTGGGAGGA TTGCCTGAGG
14701 CCAGGAGTTT GAGACCTGGG CAGCATATGA AGACCCTGTC TCTAAAAAAC
14751 TAAAAATAAA AAATAGCCAG GTGTGGTTGG TGTGCTTGTG GTCCCAGCTA
14801 CTCAAGAGGC TGAGGCAAGA GGGTTGCTTG AGCCCAGAAG TTGGAGGCTG
14851 CCGTGAACTG TGATTGCACC ACTGCACTTC AGCCTGGGTG ACATAGCAAG
14901 ACCCTGTCTC TGTGGTGGTG GTGGGTGGGG GTGGGGGAAG GGATTTAAGA
14951 AGGGTTTGTG AGGTATGTAT TATTTATAAA TGGGCTTTTA ACTTTACCCT
```

FIGURE 3E

```
15001 TCACATCTTG GGTTGAAATT AATTGTATCC ATTCTCAGTT TTTCTGTCTT
15051 GCTATATATT TAAACTTGGA GACTTAGAGG TCATGGATGT CTTTCTATGA
15101 AAAGCAAATG AAGCAGAGGG CTGCCTTCTC TTGCTGTAGA GGGCACACTT
15151 GCTGCAGAGC ATGTTACTGT TTTATGCATT GCTAGGCTTT GGGAGTTGTG
15201 ACTTGTATGA TCATAGTACT TACAACTATT AGTTGGCAAT TTTTAAACTT
15251 TAACTTTAGA TTATATATGT AAACTCCTGT GTTCCTTTGT CACTGATAAT
15301 CTGAACAGAA GCCTTGGATA AATAATTTTG AAGTTTTTGT CTGAACCTCT
15351 GAAATTTGTA TTGTTATCTC ATGGTTTTGC TGGGAGGAAG GAGAAATAAC
15401 AATGGCCACT TACTGTGCTT CTGTATGTGC CAGACAGTAT GTGCTAGATG
15451 TTTCAGAAAC GTGATTTGTA ATCCTGACAA GAAGCCTAAT TGGGTGGTAG
15501 TGGGTGCTAA TTGAACCTTA TAGATGAGGA AATTGAGGCT CATGGTGGTA
15551 AGTGAATAAC TTGCACCAAG ATCCTATGGC TGGTATGCAG TAGAGCCTCA
15601 ATTCAAGTAC GGGTCTTCCA GGTCCAAACC CATGCAGGCT TTGAGAGGTA
15651 AGGAGGTAGA GAACGTTGAC ACCCCCTTCT TGGTGTGTTT TTCAGCAAAT
15701 ACTTGTATGC ATATTAAAGA CTGTCTACCC TTTTGTCATC TTGTGTCACT
15751 TGCTGCTTCC TTTGGTACTA CCCAAATTTC TTTCAGCATT TCAGCTTTGA
15801 ATTTTTATTT TTATTTTATT TAATTTATTT ATTTTTTTGA GATGGAGTCT
15851 CACTCTGTTG TCCAGGCTGG AGTGCAGTGG CGTGATATCA GCTCACTGCA
15901 ACCTCTGCCT CACAGGTTCA AGCAATTCTT CCTGCCTCAG CCTCCTTAGT
15951 AGCTGGGACT GGAGGTGCCC ACCACCACGC CCAACTAATT TTTGTATTTT
16001 TAGTAGAGAT AGGGTTTTAC CTTGTTGGCC AGGCTGGTTT TGAACTCTTG
16051 GCCTCAAGTG ATCCACCCAC CTCGGCCTCC CAAAATGCTG GGATTACAGG
16101 CATGAGCCAC TGCACCTGGC CAGCTTTGAA TTTTTAGAAT ACTGTTCTAA
16151 ACAGAACTAT ATTGGAACCT GGAAAATTAA TCTATTGTCT CTAAATACCA
16201 AAGAAAAACA TGTAATTTTA GTGGTTGATT ATGGGAACAA TTTTTTTTAA
16251 GATGGTTCAT CTGAATGGGA AGCATTTTTT TTTTAATTGC TTGACTATTT
16301 CTTTAAATTT GGAGAAAAGA CCATTGCCCT CTCAGATTTC TGGTAATTGG
16351 TCACATTGAT CATTTATATT GACTGACAGG CTGCTTTGTC CACAGCTGAA
16401 GGATTGTTTA ATTTTTTTTA AATTATAAGA GTAATATGTG CTCACTGTAA
16451 AATTCACAGT ACAGAAGCAT ATGAACTAAC TAAAAGTTCT TACCTCTTGT
16501 CTCCAGCAAG GAGTAAGTGT TTCAACCTGA AGGTTGGTTT TGAATTGTGT
16551 TCTGTGGAGC GTACTTAAAG TGAGTGAAGA AGAAAAATTT ATGTCAATCA
16601 TGATCATTGC AGCTGAAGTT TTTATTGTTT CACCCCCTAA AGGTTATTAA
16651 AATAGTATGT AGTTTAGTAG TCTTGATAAT TTTCCCTTAA GATTTATTGG
16701 CCAGTATATC AGGATTTTGT TTTAAATTTG ATATGTGAGC TTAGTTTTAT
16751 GCTATTTTCA AATAAGACAT TTAGAAGAAG ATAAAATAAC ATTCCTGTCT
16801 TAGTCTGTTT TCTGCTGCTA TAACAGAATA GCACAGACTG GTAATTTAT
16851 AAACAGTAGA AGTTTATTTG GCCTGTGGTT CTGGAGGCTG GAACTTCAA
16901 GAGCATGGTT CTGCCCTTTG TGCTGTGTTA TCATATGGTG GAAGGTGGAA
16951 AGGCAAGTGG GTATGTCAAG ACAGAGAGCA AGAAGGGGCT TGAACTCACT
17001 TTTATAACAG AGTGACTCCA GAGATAGCTA ACCCACTTTT GAGAGAATGC
17051 ATTAATCCAT TCATGAGGGC AGAGCCCTTG TGACCTAATC ACCTCTCATT
17101 AGGCTCTGCA TCCTTAAACT GGTTTTTTTT TGTTTTTTTT TTTTGAGACG
17151 GAGTCTCGCT CTGTTGCCCA GGCCGGACTG CGGACTGCAG TGGCGCAATC
17201 TCGGCTCACT GCAAGCTCCG CCTCCCGGGT TCACGCCATT CTCCTGCCTC
17251 AGCCTCCCGA GTAGCTGGGA CTACAGGCGC CCGCCACCGT GCCCGGCTAA
17301 TTTTTTGTAT TTTTTTAGTA GAGACGGGGT TTCACCTTGT TAGCCAGGAT
17351 GGTCTCGATC TCCTGACCTC ATGATCCACC CGCCTCGGCC TCCCAAAGTG
17401 CTGGGATTAC AGGCGTGAGC CACCGCGCCC GGCCCCCCTT AAACTGTTGT
17451 ATTGGGGATT AAGTATCTAA CACAGGAACT TTGGAGGATA CATTTAAACC
17501 ATAAGAATTC CTGTCATGCA AATGAATCCA TTCTAGATGA AAGAGAATGA
17551 ATTTAGTTTC CATTGAACTT TATAAATAGG CCTTTTCTAA GGTACTTACA
17601 GCTGATATTA TAAAATTTAT ATTTGTTTTT ATAAATTTGT ATTTGTATTT
17651 CTGTTTGTAC AAATACAATT ATACACTATA GTTCTCTGCT GTTAGATTTT
17701 TTTTCTTCCT TAGCATGTTT CCAAAGGGTG GAATGTTGAA AGTTGGGTTA
17751 ATGTCAATCA GCTTTCTTTT GTAAAGTGTT CATTGACATG TGAACCTTGT
17801 CTGAGAATCT AAATTTTATT TCATGAAAGA AGAAAACAGT ATATTCTCAT
17851 TTAACCCAGA ATTTAACTTC ATATACTTGT GGCTGTATTG GGAGTATGCC
17901 ATTGCTGTCT GTTTACAACC TGACCTACTC TACCTACTTA GAAGTAATTT
17951 GTGTTATGAT AGGTGTGCTG TGCTGACATA TGCTGAACAT ATTTGTAAGG
```

FIGURE 3F

```
18001 GTGTTAAGTC ATTGAATAAA ACGCTTTTCT CCTCCTTTCA AATAACATTT
18051 TTTATTTCTG GTTATAAAAG TCATACAAGC TTACTGCAGG TTGTTAAAAA
18101 GGTATAAAGA AGAAACCGTC AATCCATTAT AATCCTACAG TTTAGACTTC
18151 CTGCTCCAGC CTCTCAGAGT GCTGAGATGA GCTAGCCATG CCCAGCCCCT
18201 CAAAAGATTT TTTAAAAAAC AAAAATGAGG TTATACTTTA AAAAATTCTA
18251 TATTCCTTTC ACATAACAGT GTTATTTTGG AGGTTTTAGA ATTTCCAGTA
18301 GCATTTTAGA TTCAGAAACA AGCTGATTCA TCCTCTACTT TGTACTTTAG
18351 GCAAGAAAAG AATTTTACCT AAATAGAATT TTGAACTGAA AATCTGTTTT
18401 TCTAACTTTT TATTTAAAGA ATATTGTTCC ATGCTTTCAC AGTAGTGACT
18451 TTTAATTTTT ATATTTTTTA TTTTATTTAT TTAGAGATGG GGGTCTCACT
18501 CTTGTTGCCT AGGCTAGAGT GAGTGCAATG GTTCTATTCC TAGCTCACTG
18551 CAACCTTGAA CTCCTGGGCT CAAGTTACCC TCCTGCCTCA GCCTTCTAAG
18601 TAGCTGGGAC TACAGGTGTG CACCACTGCA CCAGGCTTTT TTTAAAGGCA
18651 TAGAAAATGG TAGTGCTTGC ATACAAAAAT GGCGTAGGTA CATACATCAG
18701 CGGACATCAA GACTATGTTC AGATCATAAA TGTACATATA TGTACCGATG
18751 CCATTTTTGC ACGCAAACAA ATAATGGAAA TTGAACTCTA AACTGAAATT
18801 TGAAACAAGG GTTCTGGGGT GGGCCCTCTT GCTGATTTGT AATTGAATGT
18851 ATAGTTCAAT TTTTCCCCAT CTGTTAAGCA AAAGACAATT CTAATGTTAG
18901 CAAAAATCCA CATATCCTGT CATTGATCAT TTTTTCCTTA ATTTTCTTTA
18951 AGAGATGGGG CTTCTCTCTA TGTTGCCCAG GCTGGTCTGG AACTCTTGGG
19001 CTCAAATGAT CCTCCAGCCT CAGCCTCCCA AAGTGCTGGA ATTAATAGGC
19051 ACAAGCTGCT GTGCCTGGCC CTGTCATCAG TCATTTAACT TCATGCAAAC
19101 TGAGTAGAAT AAAACTCGTC CTTACTGTAC CTTATTGCTT TTGTTTTATT
19151 GTTGGAACCT CCAATATTGC GAAAGTAGAC CAAAAGTTGA CTTATAGGAA
19201 AAACTGATAG CAAAAATAAT TTTTCTCTTG TTGCTGTATT TCATGCCCAC
19251 CATCCAGTTG TTAAAGCCTA CTGTTAATTT CTCTCAGCCT CCTCCTTTCT
19301 GTCCAGGCTT ATTCTATGCC ATTCTTACCT TAACTGTTTT TAGCTTTCTC
19351 ATAGAGTGAA CTTTTTAAAT TAAAATAAAA TATCTGCTCG TAGTATTATA
19401 AAATTCAAGC AGTTCAACAG AATTTTTCAC TAATAGAAAT ACTTGTACCT
19451 CAAAAGCAGC TTTATTTTAC AAACCCAGCC CAATTTGTGA TTAGATTTAA
19501 CTTGAGAAAA CATGAAATGT CTCTCATATT GTTTAAAAAT ATCATAAGTG
19551 GCTGGGCACG GTGGCTTATG CCTATAATCC CAACACTTTG GGAGGCTGAG
19601 GCAGGTGGAT CACTTGAGGT CAGGAGTTTG AGACCAGCCA GGNNNNNNNN
19651 NNNNNNNNNN NNNNNNNNNN NNNNNNNNNN NNNNNNNNNN NNNNNNNNNN
19701 NNNNNNNNNN NNNNNNNNNN NNNNNNNNNN NNNNNNNNNN NNNNNNNNNN
19751 NNNNNNNNNN NNNNNNNNNN NNNNNNNNNN NNNNNNNNNN NNNNNNNNNN
19801 NNNNNNNNNN NNNNNNNNNN NNNNNNNNNN NNNNNNNNNN NNNNNNNNNN
19851 NNNNNNNNNN NNNNNNNNNN NNNNNNNNNN NNNNNNNNNN NNNNNNNNNN
19901 NNNNNNNNNN NNNNNNNNNN NNNNNNNNNN NNNNNNNNNN NNNNNNNNNN
19951 NNNNNNNNNN NNNNNNNNNN NNNNNNNTTC ACCATGTTGG CCAGGCTGGT
20001 CTCAAACTCC TGACCTCAGG TGATCCACCT GCCTGGGCCT CCCAAAGTGC
20051 TGGGATTATA GGCTTGAGCC TCGCCTGGCC TCCTCATAAT TTTTTAACCT
20101 TTATAAAAAC CTTTTCTAAA ACCCTTTTTA TTTTGAACTA AATTTAGATT
20151 TACTGAAATT GTGAAATCAA TGTGGAGTTC TTGTATACCC TTCTTTCCGC
20201 TTTTCCTAAT AGTAACATCT TACATACATG GTACATTTGT CCAAATTAAG
20251 AAATAAACAT TGGTACAGTG TTAACTATAG ACTTAATCTG GTTTCTCTAA
20301 TTTTTTCACT AATGTTCTTT TTCTGTTCTA GGATCTAATT CAGTATACCA
20351 TATTGTATTT AGTTGTAGGC CATGTTAGCC ACCTTCAATC TGTGACAGTT
20401 TCTCAGTCTT TCCTTCTTTT TCGTTATCTT GACAAGTTTG AAGAGTGCTG
20451 ATAGGTATTT TATAGAATGT CCGTCAGTTG TCTGTCAGTT TGTATTTGTC
20501 TGATGTATTT TTTTTTTTTT TTTGAGATGG GTGTCTCGCT CTGTCGCCTA
20551 GGCTGGAGTG CAATGGCATG ATCTTGGCTC AATGCAGCCT CCACCTCCGG
20601 GGTTCAAGTG ACTGTCCTGC CTCAGTCTCC CAAGTAACTG AAACTACAGG
20651 CATGTGCCAC CACGCCTGGC TAATTTTTTG TATTTTAGTA GAGAAGCAGT
20701 TTCACCGTGT TGCCCAGGCT GGTCTCGTGC TCCTGAGCTC AGGCAATCCA
20751 CCCGCATTGG CCTCCCAAAG CGCTAGGATT ACAGGTGTGA GCCACCATGC
20801 CTGGCCAATA TTTTGAGGGA TATACTTTGG TGAGGTCATG CAGATATCCT
20851 GTTTCTCCTT AGTTTTATCG ATTAATTTAG CATTTATCCA GTAAATCTTC
20901 CTTGCAGCAA TTATTTTTTC TTTTTCTTTT TTCCTTAATT TTTTTTTTAA
20951 GAGATGGGAT CTCACTCTGT TGCCCAAGTT GGAATGCAGT AGTGAGTTCA
```

FIGURE 3G

```
21001 TAGCTCACTG CAGCCTCAAA CTCCTGGGCT CAAGTGATCC TTCTGCCTCA
21051 GCCTCTCAAG TAGCTGGGAC TACAGGCATA GACCACCACA CCCAGCTAAT
21101 TAAAAAAAAT ATTTTTAGAG ATGGGGGTTT TGCTATGTTG CTCAGGCTGG
21151 TCTTGAACTT GCTGGCCTCA TGTGATCCTT CTACCTCAGC CTTACAAGTA
21201 GGTGGGAATT ACAGGTGTGA GCCACCACAC CCAGCATTGC AGCAATTATT
21251 AATGTAGTGC TACTGGTCAT TTTCTGTTTT TCTCATTTCT TCAGCATGTG
21301 TTATTGACTT GTCTCTTCCC TCCCATTTAT AATCATTTAT ACTGCTATGA
21351 ATTCATGAGT ATTTATTTTG TGAGTTATAA TCTAATACGT ACTTAATTTA
21401 TTTTGTGCCT CAAATTGTTC TGGCTTGGCC ATTTTTTTTT TTTTTTTTTG
21451 AGACGGTCTC GCTCTGCTGC CCAGGCTGGA GTGCAGTAGC GCCATCTCTT
21501 CTCACTGCAA CCTCCACCTC CCGGGTTCAA GCGATTCTCC TGCCTCAGCC
21551 TCCTGAGTAG CTGGGACTAC AGGCGTGTGC CGCCACACCC GTCTAATTTT
21601 TTGTATTTTT AGTAGAGACA GGGTTTCACC ATGTTAGCCA GGATGGTCTC
21651 GATCTCCTGA CCTCGTGATC TGCCCGCCTC AGCCTCCAAA AGTGCTGGGA
21701 TTACAGGTGT GAGCCACCAA GCCCGACCGG CTCCTGTATC CTTTTAACAT
21751 GAGGTGCTGT CATCATTTTT TCCCCCTAAT ATTTTGGCCA AAAATGTTAA
21801 TCAAGGATGG CACAAATTTT CTGTAGCTGT ATCTCACAAT GAAAGAGGCC
21851 TGATTAAAAA TGTAAAACTA AAATGTTCTC TGATCTCTTA GCACATGCTT
21901 TGTAAAAGGC ACAGTGCTAG ATCCTTGTAT ACGTAGATGA GTAAGTCAGC
21951 TTACCTTCCA CACCCACAGA TAGCTATGTC AAACGTAAGG GTGGAGAAAC
22001 ACAGACCCCA AACTTCTCGA GGGTAGAAAA TATGAGGTTA TAGTAGATTA
22051 GAACTACAAA AAGCTAGAGG AAGTTCTGAA CTGGAAACAG TGGATAGGAT
22101 TTACTAGAAT AATTTACGAG GGTGACAATT GTAAATCTTC ATAGGTTTCT
22151 TTTTTTTCCT TTCTCTTTTT TTTTTTTTGA GATGGAGTCT CGCTCTGTTG
22201 CCCAGGCTGG AGTGCAATGG CGCAGTCTCT CCTCACTGCA ACCTCCGCCT
22251 CCTGGGTCCA GGTGATTCTC CTGCCTTAGC CACCCAAGTA GCTGGGATTA
22301 CAGGCATCTG CCACCATGCT GAGCTAATTT TTGTATTTTT TTTTTTAGTA
22351 GAGACGGGGT TTCACCATGT TGGTCAGGCT GGTCTTGAAC TCCTGACCTC
22401 AGGTAATCCA CCCACCTTGG CCTCCCAAAG TGCTGGGATT ACAGGTGTGA
22451 GCCACCGCGC CCAGCCAAAT TTTTATTGGT TTCTAAACTA GCGTAATTTA
22501 GTTTTTTTCA CTTAAGTCAA AATTATATTA TTGTAGGATA AAAACTTAGT
22551 GATCCAAATT CATGAGGAAT GAAGAATAAA TACATTTAAA GTCTTACCAT
22601 TTGCTAAATT AGTCTTGGCT CTTTGTACCA AAATTCTGTC CTTGTGCTCT
22651 GTAATTTTAT ATTTGTATAT TTTCTATCAA CATTTTTACT GTGTGGTGTT
22701 TTGTAAATTA TAAAAACGTT TTAAAGCAAA CTCAGAACAA TGAATTCTCA
22751 CGAATATTCA GTATATTTAC AGTTGAGAAA TAAACTACTT CTGTAGTAGG
22801 TAATTTAAAA TGTCCCAATG CAAGTTAACG TGTCACTGAT CACGCTATTC
22851 AGGTGTGTGT CTTTGATAAG GGGAGGTGGG GAAGTTTGTG GGTTTGATTT
22901 TATTTGCCTT TCTCATGTGA CTGTTGTCAT GTTAGTAAAC AAATGGTTTG
22951 CGAGAGAACC AGTAGTCTTT TGCAAAGATT GTCTTATACA GAGCACTCAA
23001 TTCTTCATAT TATTTATAAT GGCTTTAATT TAAGCCTTAA ATTATTAGAA
23051 ACTCATAAAT AATTTTTTTA TTTGTTTTTT TGAGATGGAG TTTCGCCCTT
23101 ATTGTCCAGG CTGAAGTACA ATGATGTGAT CTTGACTCAC TGCAACCTCC
23151 GCCTCTCGGG TTCAAGTGAT TCTCCTGCCT TTGCCTCCCA AGTAGCTGGG
23201 ATTACAGGCA TGCGCTACCA TGCCTGGCTA ATTTTGTATT TTTAGTAAAG
23251 ACAGGATTGC ACCATGTTGG CCAGGCTGGT CTCGAACTCC CAACCTCAGG
23301 TGATCCACCT GCTTCGGCCT CCCAGAGTGC TGGGATTACA GGCTCACTGA
23351 GCCACTGTGC CCAGCCATAA TGCGTTAAAA TAAGAGTGTT ATATTTGTAA
23401 AACTTAAAAA AATGTAGTGG TTGAAAAAGG TAATTTAAAA AGAATTGACT
23451 ATTAATTTCT TGAAACCATA ATGTAACTTG TAGTGCAATT AGGAAACCTT
23501 CATGTTTCTT TCTTTCTTTC TTTTTTTTTT TTTTGAGAT GGAGTTTTGC
23551 TCTTGTTGCC TAGGCTGGAG TGTGTGATGT CAGCGCACTG CAACCTCTGC
23601 CTCCTGGGTT CAAGCAATTC TCCTGCCTCA GCCTCCCGAG TAGCTGGGAT
23651 TACAGGCGCC TGCCACCACA CCCAGCTAAT TTTTGTATTT TTAGTAGAGG
23701 CGGGGTTTCA TCGTGTTGGC CTGGCTGGTC TCGAACTCCT GACCTCAGGT
23751 GATCCACTGC ACCTGGCCCC CGTTCATGTC TTTTAAAGCT TTATGGTTGC
23801 TCTGAAATAG AGTTGTTGAT TTTTTTTTTT TTTTTGAGAC TCCTCTTTTG
23851 CCCGTGCTGG AGTGCAGTGG TGTGATCTGA GCTCACTGCA ACCTCCACCT
23901 CCTGAGTTCA AGCAATTCTC ATGGGTCAGC CTCTCAAGTA GCTGAGATTA
23951 AAGCTGCCCA CCACCATGCC TAGCTAATTT TAGTATTTTT AGTAGAGATG
```

FIGURE 3H

```
24001 GGGTTTCACC GTATTGGCCA GGGTGGTCTG GAACTTCTGA CCTCAGGCAT
24051 GAGCCACTAC GCCTAGCCTG GGTTGTTGAT CTTTAAGGTG ATACTTCAGG
24101 CAACATCTGA GGCCCAGTAC AGTCCTTTAC TTCAACTGGC TCCAGTACAG
24151 CAAATTCAGG GAATGTTTTT GAGTGTTTAC TGGATGCCTG GCGTGGAGTT
24201 CAGGGAGATT GGTACATTGA GTCCAGTTGT TGTGTTGAAA CTTCTGTTTA
24251 AAAACCTCCC TACTAAGTCC CAGCTACTCA GGAGGCTGAG GCCTGAGAAT
24301 CACTTGAACA CCTGGAGGCA GAGGTTGCAG TGAATCGAGA TCGAGCCACT
24351 GCACTCCAGC CTGGGCGACA GAGTGAGACT GTCTAACAAC AAAAACAACA
24401 CCCCCCAAAA AACCAACCTA CTATGGTAGT ATCAATGCTG TGATAGTCTT
24451 CCTTTCTTCA TACAGGTAAA TTCTTAACAT ATACTCATTG TTAATGTTCA
24501 GTGTTCAGTA TTCTTAAGAG TATTTGGGGC CAGGCACGGT GGCTCATGCC
24551 TGTACTCCCA GCACTTTGGG AGGCTGAGGT GAGCAGATTA CCTGAGGTTA
24601 GGAGCTTGAG AACAGCCTCC AACATGATGA AACTCCCGTC TTTACTAGAA
24651 ATACAAAAAT TAGCTGGGTG TGTTAGCACA TGTCTGTAAT CCCAGCTACT
24701 TCAGAGGCTG AGGCAGGAGA ATTGCTTGAA CCTGGGAGGT GGAGGCTGCA
24751 GTGACCTGAG ATTGCTTCAC TGCACTCCAG CCTGGGCAAC AGAGCGAGAC
24801 TCTTGTCTCA AAACAAACAA ACAAAAAAAG AATATTTGGG GCCAGGCATG
24851 GTGGCTCACA CCTGTAGTCC CAGCACTTTG GGAGGCCAAG GTGGGTGGAT
24901 CACTTGAGAT CAGGAGTTGG AGACCAGCCC GACCAACATG GCTAAATCCC
24951 GTCTCTACTA AAAGTACAAA AATTAGCTTG AGCAACAGAG CAAGACTCTG
25001 TCTCAAAAAA AGAAAGAAGA ATATTTGGTT TAATTAAGAA GGAACCTTAT
25051 CAATAGTAGT AAAGTCAGCC AGCTGAACTG CCAAGTACAA ATTGTTGGTA
25101 TTAGGTATCA ATCATTTATT AAGGATAATA TTCTACAATA GCGATCTTTT
25151 TAAAAATTTT AAAATCTCAA ACTGGAAAGG ATGTCTAGTT CATTCTATGC
25201 TTCAGTCCCC TCTTCTGATT TACTTGTTTA GAAGATTTTT GTTTCCTTCT
25251 CTGACTTCTA TTTTGCTGCT GACTGGCACT TGGGATTTTT AAAAAATTAT
25301 TTTCCTCATA TATAATTAAA GACAATAAGT ATAACAATAA GTATAATATG
25351 GTAATTTGCT AAAACCCAAA CAATGTTTTA AGTAATGCAT ATCATTATGT
25401 AAACCTACGT AATAGTTGAA TATTCACAAA GATAATCGCT TATAGAAGTT
25451 TTATATCCTC TCTTCTTTGG CAGTGCAATT AAAACAAAAA AAATAAGTTT
25501 TATGTCTTGT TTACATGTAA ATAATTTTAA TCTAAATTGT GACGTGGTTT
25551 TCACTTTAGC ATATTTTTGA AAGTAAATCA AAAAGGACAA AATACAAAAT
25601 CATGTATATC TTCTACAAAA ACGATATATA AATTCTAAGG TTTTTGTCCT
25651 TTTGAAATTG CTTAAAAGAA TGCATAGAAC TGGTGTCTGA GTTGGGAAGG
25701 ATCTATGAGG GATTTCCTTG GAGACCGTGG GTGAATAATA ATGTTGTCTT
25751 AGTTCCATGA AGGAATCTCT GGGGATAGTT TTTGAGTTAG GCCTGGCAAT
25801 GTTAGAGATA CATAAAGAGA GCCTTGTTTT ATCACTGGGT GCGGTGGCTC
25851 ACACCTGTAA TTCCAGCACT TTGGGAGGCT GAGGCGGGCA GATCATGAGG
25901 TCAGGAGATC GAGACCATCC TGGCCAACAC GGTGAAACCC GTGTCTACTA
25951 AAAATACAAA AATTAGCTGG GCGTGGTGGC GCATGCCTAT AATCCCAGCT
26001 ACTCGGGAGG CTGAGGCAGG AGAATCACTT GAACCAGGGA GGTTGGAGGTT
26051 GCAGTGAGCC GAGATCGCGC CACTGCACTC CAGCCTGGGT GACAGAGCAA
26101 GACTCCGTCT CAAAAAAAAA AAGCTTGGTT TTCAATGGTT CTGAAAAATG
26151 CTTTAATACA AGTGTAGAGT GTTAGTCAAG TTTTGCACTT GGATAAACAG
26201 CCTGTGAATT TATCACATTT CTAGTTTATA ATATGGGCTT TCAGAAGTTA
26251 TATGAACATT GTTTTGACGG GAGAATTCAA GCTGGATGCT AGAGAAGGAT
26301 CGTGAGAACC CCTTCATTGG AGGAGTGCTA TGAAATTATT TGATCTTGGA
26351 ATTTTTTTTT TTTTTTTTT TTTTTTTTT TTTTGAGAC AGAGTTTCGT
26401 TCTTATTGCC CAGGCTGGAG CTGGAATGCA GTGGCACGAT CTCGGCTCAC
26451 TGCAACCTCT GCCTCCTGGG TTCAAGCAAT TCTTCTGCCT CAGCCTACCA
26501 GGTAGCTGGG ATTACAGGCA TGCGCAACCA TGCCCAGCTA ATTTTGTAT
26551 TTTTAATGGA GACGGGGTTT CACCATGTTG GTCAGGCTGG TCTTGAACTC
26601 CTGACCTCAA GTGAACTGCC TGCCTCAGCC TCCCAAAGTG TTGGGATTAC
26651 AGGTGTGAGC CACTGCGCCT GGCCTGATCT TAGAATTTGA AGGAGAGACT
26701 AATATTTCAT GGGCAAAAAC AATGAAAGT TACCTTTCTG TATTCTAATA
26751 CTATAGAGGA GTGGGATTTA TTTAGAATGT TTTAAGTATC TTGGGCAGTC
26801 CAAGAGTGCG TATCACTTAT TTTTCTTTTC CTTCTTTCTT TTTAAGTGGA
26851 AGTTCACTGA TGTTAGAGAT CATAGGTGGC ATTGCCTACT TTTTACATAA
26901 TTTTATCATG TTTAGTGATC TGTCAGAAGG GCTGTGGCTG TTTGCAGTTT
26951 TGGCTTAAGC CATGCATGGG CTTTATAGGA GATGTAGTCT TCACAGTGAG
```

FIGURE 3I

```
27001 TTGTTATTTG TAGCTGTGTT TTTGTTTTTG TATAGCTTAT AGCAATGCAG
27051 TGTGCTTTTT ATTAACATCA TTTTCTTTTT CTTTTGCAG TGATTATTTA
27101 TTCAAGTTAC TTCTGATTGG CGACTCAGGG GTTGGAAAGT CTTGCCTTCT
27151 TCTTAGGTTT GCAGTAAGTT GAAATTGAAA TGTCTTTACA ATTAATGGTA
27201 CAATTAATGC TATGTATGTT TTCTAGGTAG ATAAAATTAA ACAGTTTTAT
27251 TCAGAATAAG TTAATTCTTC CAGAATTTAT ATATTTAAAG ACTCCAAATA
27301 TACATCCCCA GTGGTATCTT GGACTGTTAA ATAGAAAAAT ATTGTTGCTC
27351 TTAAAAGAAA TTCAGTGAAG TCTGGTTATA AAGTCAGAAT GTCTAATACT
27401 TTTGGTCAGA GTCAAACAGC AGTTCCAATA TAGGCAGCAA GTTAAAGGGG
27451 TAGTTGGTGG CCTGTGTTGA AAGCGACTTG ATGAAAATAA ATCTTTAAAT
27501 TAAACTTTAG TAGAATAAAA AGAAAAAGCA GAGCCAGGTG ACGCAGTGGA
27551 TCATGCCTGC AGTCTCAGCT ACTCAGGGTG CTGAGGGTGG AAGGATCACT
27601 TGAGTCTAGG AGTTTTGAGA CCAACCTGGA CAACATAGCA TGACTCTGTC
27651 TCTGAAAAAA AAAGTTAATA AAAGAAAAAG TAGGGTCTTG ACAAACTTC
27701 GTTGGCCAAT GGCATAGTTC TAAATGCTGA AGCTGACAGA TAAAGGACTT
27751 TTGACTTAAC AGAATCCACA GTGTCCTTCA TAGTCTTTAT CAACTACCTT
27801 TAAATTTAGC ATGTTTCCTG GCCAGGTGCG GTGGCTCACG CCTGTAATCC
27851 CAGCACTTTG GGAGGCCGAG ACGGGCGGAT CACAAGGTCA AGAGATTGAG
27901 ACCATCCTGG CTAACACGGT GAAACCCCGT CTCTACTAAA AATACAAAAA
27951 ATCAGCTGGG TGTGGTGCCA CACGCCTGTA GTCCCAGCTA CTCGGGAGGC
28001 TGAGGCAGGA GAATCGCTTG AACCCAGGAG GCGGAGGTTG CAGTGAGCTG
28051 AGATGGTGCC ACTGCACTCC AGCCTGGCAA CAGAGCAAGA CTGTCTCAAA
28101 AAAAAAAGAA AAAAAATAAA AAAACAAATT AGCATGTTTC CCTTCTAGAG
28151 ATCATTGTTT CTCAGAGCAT GGACCAAAGA CTCCTGGGGG TTACCAAGAC
28201 CCTCTCAGGT AGCCCATGAG GTCAAAATAT CCTAATAATA CTAAGATGTT
28251 AGTATTTGTA AGGAAATATT TACTTGGTAA TAATACTAAT ATAAAAGATG
28301 TTTGCGTTTT TCAGTGATGA CATTGGCTCT GGTACAAAAG CATGTGGGTA
28351 AAATTGCTGC TGGCTTGGTA CACATCAAGG CAGCGCTAAG CTCCAAATTG
28401 TACTCATGGT GATGGCATTC TTTACCTCTG TGCCCTCACA GGAACAAAAA
28451 CAAGCCGTGC CATTTTTATT GAAGATTGTC CTTGACAAAA CAGTTAAAAT
28501 GATTAATTTT TGAAAAATGT TGATCCATGA GTATTCCTTT AAAAATATTT
28551 GTGAAGAAAT GGGAAGTTCA CATAAAACAA TGTTTTTTTT TTGTTTTTTT
28601 TTTTTTTTT TTTTGAGACA GATTCTGGCT GTGTTGCCAA GGCTAGAGTG
28651 CAGTGGCGTC TGGCTCCCAG GCTCAAGCTG TTCTCCCACT TCAGCCTCCC
28701 AAGTGGCTGG GACCTCCCAA GTGGATGCGC CATCATGCCT GGCTGATTTT
28751 TGTATTTTTT TGTAGTGACA AGGTCTCACT GTGTTGCACA GGCTGGTCTC
28801 AAACTTCTGA GCTCAAGCGA TGCATGTGCC TCAGCCTCCC AAAGTGCTGG
28851 AGAAAGCACT TTTTACTGCA TACTGGCTAG TGTGTTGGTT ATTTTGGAGA
28901 AAAGAAAAGC ATTTGTAGTT TTTTGAGTTG TAAGCTGAGC TAACTGCTTT
28951 ATTTTTTTCT GTGGAACACC ATTTCTTTTT TTTTTTTTGA GATGGAATAT
29001 TGCTTTGTTG CCCAGGCTGG AGTGCAGTGG CACAATCTCG GCTCACTGCA
29051 ACCTCCGCTT CTCGGGTTCA AGCAATTCTT CTGCCGTAGC CTCCCAAGTA
29101 GCTGGGATTA TAGGCACCTG CCACCAAGCC CAGCTAGTTT TTGTATTTTT
29151 AGTAGAGATG GGGTTTCACC ATGTTGGCCA GGCTGGTCTC GAACTCCTGA
29201 CTTCGTGATC CGCTTGTCTC AGCCTCCCAA AGTGCTGGGA TTACAGGCGT
29251 GAACTACTGC ACCTGGACAT TTTTTTTTTT TTTTAACTT GAAAGAACAG
29301 CTAACAGACA GATTAGAACA GAATTGGCTA TTTGACAGAT TTTCTCAGAT
29351 GAACTGTGAT AGTCATTTCA AGGGAAGTAG CTGCAAGCAT TTGTTGGCTG
29401 AAATAAAATT TAAGTTTATC ATGGAAAATT AGAATTTGAA AAAACTTAGA
29451 GTTTACCACT TGACAGTATC CTAAATACAT ATGACTTTTC TGATGAGTGC
29501 CGATATTAAT GAAGGTTATT TAAAAAATAT TAAATAATGT ATAATTCTTT
29551 TTATATAACA GTTAAAAATA AAACCATGAG TACTAGAATA AAACATAGGT
29601 GGCTCTTTAA TCTTGGTTTG TGAAGGTATT TTTTAAAATA AGAAAAAAGC
29651 AAGAAATCAC TGCTAAATTT GACTATTAAA ATTAATTTAT CACAGGCACA
29701 AAAATGTTAG AAAACTAATG GCAATAGCAA ATATATATAT ATGAGGATTG
29751 GTATTCTCAA CATATAAAGC ACATTTGCAC ATCAACAAGA AAAGAATATT
29801 TCTCCTAATG GAAATAGTGG CAAATACATG AGCAGTCAGT TGAAAAAAGA
29851 AGTAATACAA ATTGCTGGCT GGGTGTGGGT GGGGTCACGC CTGTAATCCC
29901 AGCATTTAGA GGCTGAGGCT GGCGGATCAT CTGAGGTCAG GAGTTCGAGA
29951 CCAGCCTGAC CAACATGGAG AAACCCTGTC TCTACTAAAA ATACAAAATT
```

FIGURE 3J

```
30001 AGCCGGATGT GGTGGCGCAT GCCTGTAATC CCAGCTACTT GGGAGGCTGA
30051 GGCAGGAGAA TTGCTTGAAC CCAGGAGGCG GAGGTTGTGG TGAGTCGAGA
30101 TCGCACCATT GCACTCCAGC CTGGGCAACA AGAGCGAAAC TCCATCTCAA
30151 AAAAAAAAAA AAAAAAAAAA AAAAGGAAGT AATACAAATT GCCAATAAAT
30201 ATGGAAAAAA AAAAAGGCTC AACTTTATTT GTAATTAAAG GCCTTTAAGT
30251 TAAACTTAGG TGTCATTTAA TTTTTATTAA ATTGGCAAAT ATTAAAATTA
30301 AGCATAATTC TTAAGCAACT CTCGGTAGGT GGGAAGAATC TAGCTGTAGC
30351 CTCAGGTGTT TGTGCCTCAA GGAAAACCCT CTCTGGGATG TCCATTGCTT
30401 GAAGTCAAAG GTTTTCCAAT AATACCTGGA AACTATTTTT AAAATGCTGA
30451 TCCCCATACC CTCAAAATAT TAATAGAGAC AATCGTGAGG ACTATAATAA
30501 AGAAATGTGC AATAAGCTCT GGGGCACAG AGGGAAGAAT CTATTGGCTG
30551 AGGAGTTGAA GAAATTGTTT GGACACTCAG TATTGCCTGA GCTCAAAACT
30601 GAAGGATGAA TAAATGCCAC ATGACCTTGG GGCTGGGGAG TAAGTAGGGT
30651 TATGCAGAGA GAGATAACTG AGGCTTTTGG GCAGACGAAT AGTAACGGCT
30701 CAGGCATGGG AGTAAAGGTC ATTTAGAGAT TTACAAGAAT TCAGCATTTC
30751 TTTCTTTTTC TTTTTTTTTT TTGAGATGGA GTCTAGCTCT GTCATCCAGG
30801 CTGGAGTACA GTGGCATGAT CTCAGCTCAC TATAACTCCC ACCTCCCGGG
30851 TTCAAGTGAT TCTCATGCCT CAGCCTCCCG AGTAGCTGGT ATTACAGGCG
30901 TGTACTACTG TGCCTGGCTA ATTTTTGTAT TTTTAGTAGA GATGGGGTTT
30951 CACCATGTTG GTCAGGCTGG TCTCCAACTG CTGAGCTCAA GTGATATGTG
31001 CACCTCTGCT CCCCAAAGTG CTGGGATTAC AGGCGTGAGC CACTGTACCC
31051 GGCCAAGAAT TCAGTATTTC TATCCAAGTA CCTGGGGGAT AGATGTGCTA
31101 CATGAATATT TATTGCATTC ATTTGTTCT CTGCATTTTT TTTTTTTTTT
31151 TTGGTTTGAG ATGGAGTCTC GCTCTGTCGC CCAGGCTGGA GTGCAGTCGT
31201 GCAATCTCGG CTCACTGCAG CCTCCACCTC ATGGGTTCAA GCGATTCTCC
31251 ATCTTGGTCT CCTGACTAGC TAGGTTTACA GGCGTGTGCC ATCACACCCA
31301 CTAATTTTTT GTATTTTTAG TAGAGACAGG GTTTCACCAT GTTGGCCAGG
31351 CTGGTCTTGA ACTCCTGATC TAAAGTGAGC CTCCCACCTT GGCCTCCCAA
31401 AGTGCTGGGA TTACATATGT GAGCCACTGC GCCTGGCCTC TATATACTTC
31451 TATAGTACCT GATACTTATT AGGCACTCAA TTACAACATA ACTTTTTTTT
31501 TTTTTTTTTT TTTTGAGACA GAGACATGCC TTGTCGCCTG GGCTGGAGTG
31551 CAGTGGCACA GTCTCGGCTC ACTGCAACCT TCACCTCCCG GGTTCAAGTG
31601 ATTCTCCTTC CTCAGCCTCC CGGGTAGCTG GGATTACAGG CGCCCGCCAC
31651 CACGTCCAGC TAATTTTTTG TATTTTTAAT AGAGATGAGG TTTCACCATC
31701 TTGGCCAGGC TGATCTCAAA CTCCTGACCT TGTGATCCAC TCACCTTGGC
31751 CTCCCAAAGT GCTGGTATTA CAGGTGTGAG CCATCATGCC CGGCCCATAT
31801 TTCTAAAAAC ATTTTCTTAT AAAATGACAT TGCCATTATC AACCTGCAAA
31851 ATACATTTCC ATTTGGTTGT TTTCTTGCTT AGTCTTTTAA TCTAGAGTTT
31901 TATACCTTAT CTTTTTTATT TATATATTTT TTATGTCATT GACTTTTTGC
31951 AGAAACTGAA GCACTTGTCC TGTAGATTGT CCAATATTCT AGATTTGTCA
32001 TTTTGTTTCC TTGTGATGTC CTTATGCTTA TTTGTTTGTC CCTCTTTCTG
32051 TAATTAGAAG ACCTAGAACT GCACTATCCT TAGAGTAGCT ACTAGCTCTA
32101 TGTAGCTATT TAAATTTAAA TTAATTAAAA TTGAAAAAGT TTGGTGGCTC
32151 ACACCTGTAA TCCCAGCACT TTGGGAGGCC AAGGTGGGAG GATTGCTTGA
32201 GTGCAGGAGT TCAAGGCTTC AGTAAGCTAC GATTGTACTC TAGCCTGGGA
32251 GACATCAAGA CCCTGTCCCT TTAAGGGGA AAAATAATTG AAAAAATCAA
32301 AAACTTAGTT TCCTTGTTTC ACAAGCTGCA TAGGGCTAAT GGCTACCATA
32351 TTGGCTAGCA CAGCTTATAG AACCTTTCCA TTGTCACAGA AAGTTCTGTT
32401 TGGCAGTGCC GTTCTCATTA GACCTGATTC GATTAAGGTC CATCTTTGTT
32451 GACAGAGTAC TTCTTAGGTG GTGCTTTGTG GTTCATATGA TGATAGCCTG
32501 GTCTGTTCAT TCATATATCT TTTCACGAGA AATATTTTTA TTCCATTCTG
32551 AATAAAATTT CATGGCAGGT ACTTGCAAGA AGCAGTTATA ATTTTAAAGT
32601 TTAACATTAG GTTAAAAAAT TGACAGGAAA CATATATTCA CAGGTAAAAC
32651 TTGTACACAA ATGTTCATGG CAGCATTATT CATAATAGCC AAGAAGTGGA
32701 AACAACCCAA TCAATTTAT GAATGGATAA AATGTTGTAT ATTTGTAGTA
32751 CATGTAATAT TATTCAGCCA ATAAAATGGG CCAGGCATGG TGGCTCACAC
32801 CTGTAATCCC AGCACTTTGA GAGGCTCAGG CAGGGGGATC ACTAGAGGTC
32851 AGGAGTTTGA GACCAGCCTG ACCATCATCA CGAAACCCTG TCTCTACTAA
32901 ACGTACAAAA ATTAGGCAGG CGTGGTGATG CACGCCTGTA GTCCCTACTA
32951 CTCAGGTGGC TGAGTCATGA GGATTGCTTG GACCCCGGGA GACAGAGGTT
```

FIGURE 3K

```
33001 GCAGTGAGCT GAGATCATGA CACTGCACTC CAGCATGGGC AACAGAGCAA
33051 CATCCTGCCT CAAAAAAAAA AAAAAAAAAA AAAAGAAGTA CTGTTACATG
33101 GTACAACATG GATGAACCTT GAAAACATTC TGCTAAATGA AGGAAGACAG
33151 ACACAGAGGG CCACATATTT TATGATTCCA TTTATACGAA ATGTCCAAAA
33201 TTGGCAAATC TAAAGAGAAA GTAGATTAGT GGTTGCCAGG GAGTGAAGAC
33251 GGGTTCTTTC TGGAGTGAAG AAAATGTCCT GGAATTCGTG GTTGTAGTTT
33301 GCAACCTTGT GAATGTATAA GGACCACTGA ATTGTCCACT TCAAAAGGGT
33351 GACTTTTATG TTATGTGCAT TATATCTAAA AAAAAAATCA TAATTAGGAA
33401 GCAAGATTGA CTTCTAAGAA AAAGCGGAGT GAAATTGTTG TTTTGTGGTG
33451 AATAAATTGG GTGGGTGGGT CGCAAGAGTT TTGCTGATTA GTGATTAGAA
33501 AAATTATTCA TAATCATTGA AAATATAAAA TATTTTTCTA TATGATGTAT
33551 GTAAAGAATT TGGCAAGAGA TGATGTTTGG AAAAAATAAA GAATGGCTAT
33601 TGTAGAGATC TTAAGGAAAG AAACTACAGT TAAGTAGTGC TTTGTAATCA
33651 GAATATGAAG TAAGTACTGA AAGTGGATGG AGTGGCTGTT GTCAGCATGT
33701 TATACTTTAT ACATTTCATT CATAAATTTG GACTGTAGAT AAAAGTAAAC
33751 TTTTTTTTTA TTTACTCTTG AACAACAGTT TTTTTTTTTC CACTTAGACT
33801 TGCATCTGCT CCACTGAACA ATACATTTAA TTGTTAATTA TTTCCCCCTT
33851 CAGGATGATA CATATACAGA AAGCTACATC AGCACAATTG GTGTGGATTT
33901 CAAAATAAGA ACTATAGAGT TAGACGGGAA AACAATCAAG CTTCAAATAG
33951 TAAGTGACTT GGCTAGTAAT TTTTTTGAAA TTTATTTTGG TAAATTTGTA
34001 ATGTATTGTT ATTTTGTATA TATTTACTAT GCTAACAAAA TTGAATGTAA
34051 AATGTCTTAA GATTCATGTA CTTAAGATAG AATGGTAGAA TAAGAATTAC
34101 TTAGATTAAA AATAATATTT TCAAGATTAC TTAAGCCTCA TTGAATTTTC
34151 TGTTCATGAA GCAGAGAAAC TCATGTTTTA AGTCAAACTT GGTCCTCATC
34201 TTTTTCTTTT ATCAGTGGAA ATCTAAGTTC AAGTTTACCT TGTCCTACAC
34251 TGCAAATGTT ATAGACCATT TTTGTTTGTC TTTTACTGTG CTAAGTGCAT
34301 GGAACATTAA AGGAACCCTA GGAAGAGATT CTTCATATGT GGCTCAGTTG
34351 AAGAGAAGTA CTTATGTAGT TCTAAGTATT TTTATTAGAT AGTGTGCACC
34401 AACTCTGTAG AAACACAGAA TTTTGTTGGA AAAAGGAACT TAGTTTTTGT
34451 AACATGTTCA TTTTACTGCT CAAAAAAACG AATGCTGAAA GATTTAATGA
34501 CTTGCCTACA GTTACTGGTA GAACCAAGTG ACCGAAGCTC TGTCTTCAAT
34551 ATTTTGTGTC TGTGTGCCAT CCTATCCCCC TTATCCATCT TTACACCCCC
34601 AGCCCCCAAT TAAATATAGG CAATTATAAT AGTTCAGTTG TGCCTCTTCA
34651 GTATGGGTCT GAGTCCTGTC AGTGTGGGCA TATCTGTGGT CTTTTAAAAA
34701 ATAAATCTCT CAGTATTTTT CAGAGTAGGC TATTAGCAAG AAGTAGGCTA
34751 TAAACACAGG AAACCAGTGA CTGCCCCTTT TCATGGAACT GATGACACAT
34801 GGAATTGGAA GGAGTCCTGC ATTAGGAGTC AGAAGACTTA GATTTGTTGT
34851 CTTGGTTCTA GTATTTACCT GTTAGAGAAT CATGGGTTTG TGTCTCTGGG
34901 GAAAAGGCCG AAGTAACCCT GAGACCCAGT TTCCTTTCTA AAATGTGTGT
34951 GATGACACCT GATTTACTAA TTTATAAGCT AGTTGTGAGA ACCAACTGTA
35001 ATAGCTTTGT GTATGTGACA ATACGTGTGA AAGCCCTTTG TAAACTTTTG
35051 GGCAGCATAT AGATACTACT TATGATATGA CATGCCCAGA TAAATGGGTG
35101 TTTGATAGGT TAAGTTGCTC CCTTTTCTTA CATGACTCTG ATGAGGAAAA
35151 GAAGGTATGT TAACAAAAGA TAGGTGGCTG TGGATATTGA TATAAGTAAA
35201 CACACTTGAT GTGTCAAATT AGGACTTGCA AGGATTTAGT TTTCAGAAAT
35251 AGCTTGAAAT ACTTTCAATC AGTGAACAAA TTACCCTCCA TATTTTTTCC
35301 CACGATATAA GTACAGTCTC AACCTTTTAT TTGGCACCAT AAAGAGCACA
35351 TAAAGATCTA CCCAAAACTG TACTTTAAAG CACTGGTATG GAATAATTGT
35401 ATTATGTGTG ATCATTGGTG TTTATAAGAT TTGGGTGTGT ATTCGTGTGT
35451 GAAACATTCA TATTTGTTA CTTTCCTGTG GCTGGAAGGG ATCTTATAGG
35501 ACACTGTCTT TCATCTTTGT CTGTCTTTCA TCTTTAATAG GAATTTCTTT
35551 TCCATGCCTG AAGGCCTCAT TTTGAACATT TTGTTTGTTT GTTTTTTTAT
35601 TTTTTGAGAT ACAGTATTGC TCTGTCTCCC AGGCTGGAGT GCAGTGGCGC
35651 GATTTGAGCT CACTGCAACC TCCGCCTCCT GGGTTCAAGT GATTCTCCTG
35701 CCTCAGCCTC CCTAATAGCT GGGATTACAT GTGTGTACCA CCATGCCCGG
35751 ACAATTTTTT TTTTTTTGAG ATGGAGCCTT GCTTTGTCGC CCAGGCTGGA
35801 GTGCCAGTGG TGCAATCTTG GCTCGCTGCA GCCTCCGCCT CCCAGGTTCA
35851 AGCAGTTCTC TTGCCTCAGC CTCCTGAGTA GCTGGGATTA CAGGCGTGCG
35901 CCACCACACC CTGCTAATTT TTTGTATTTT TAGTAGAGAC AGAGTTTCAC
35951 CATGTTGGTT AGGCTGGTCT CGAACTCCTG ACCTCGTGAT CTGCCTGACT
```

FIGURE 3L

```
36001 CGGCTTCCCA AAGTGCTGGG ATTACAGGCA TGAGCCACTG TGCCCAGCCT
36051 TCCGATAATT TTTGTATTTT TCGTAGAGAT GGGATTTCGC CATGTTGGCC
36101 AGGCTGGTCT CAAACTCCTT ACCTCAAGTG ATCCACCCGT CTTGGCCTCC
36151 CAAAGTGCTG GGATTACAGG CGTGAGCCAC CACGCCTGGG TTTTTGAACA
36201 TTTTTAAGAA GCTTACCATT TTTTCGAAAT AGCTAGTTCC ATTTTACACA
36251 TAACTTCAGC TAGGCATGTT GCCTCATGCC TGTAATCCCA GCACTTTGGG
36301 AGGCCGAGGT CAGAGAGTCA CTTGAGGCCA GGAGTCAACA TAGCTCCTGT
36351 GACCAGCCTG GTCAACATAG AGACTCTATC TCTACCAAAA AAAAAAAAAA
36401 AAAAGTAAC CAGGTGTGGT GGTCCATGCC TGTAGTCCTA GCTCCCAGG
36451 AGACTGAGGT GGGAGGAATG TTTGAGCCCA GGACTTCAAG GCTGCAGTGA
36501 GGCAAGATTG CACCATTGCA CCCCAGCTTT GGGGACAGAG TGAGAGACCC
36551 TGTCTCAAAA ACAAAATAAG CTGGGCGCA GTGGCTGTCC GGGCGTCGTG
36601 GTTCACGCTT ATAGTCCTAG CACTTTGGGA GGCCAAGGTG GCAGATTGC
36651 CTGAGCTCAG GAGGTCTAAG ACCAGCCTGA GCAACATGGC GAAACCTCAT
36701 CTTTGCAAAA CATACAGAAA AAAACAAAAA AAACCACAAA ACCTCTAGTT
36751 GCCAGTTATT TTTTTTATTT ATTCCTAGTG ATTCTTCTTT TTTTCTTTTT
36801 TCTGAGACAA AAATTTCACT TTGTCTCCCT CGCTAGAGTG CAGCGGTCAG
36851 CTCACTACAT GATTCTTTTA GAGACATGTT AATTCTTTAT ATTGAGCTGA
36901 AGCCTGTTTC TTTTACTTCT GTCTCTTCTT ATTCCTCCGC CTTGTAGAGC
36951 TGCCTGAATC AGATTAATTC CTCTTTTATT GGCAAGCCTG CCCTTCAGAT
37001 TGATCTTATC ACAACCTTTC TTCTACCTCT GAAGTCCTCA TTCTTTCCTG
37051 TAATGATATT TTCAGAACCT TGTGCAATTT GGGTTATTCT TACATTTTAT
37101 AAATGCCTTT TATTAAATTT GATTTCTTAA ATCAAGTATG AGATATAACA
37151 CATGAGGTAA ATCCTGTCTT GATTTGGAGC CTGAATGAAT TTCTCTCTTG
37201 AACTTCAAGG GCTCATGGCC CTTTCTTATT ATTAATCAAA GACAACCATT
37251 TGTTGTTTCA GTAGCTATAT TATTTCTAGT TTGGGTCTTA AGGTTTTTGA
37301 TTTGCTTGTT TTTTCTTTTT TCTTTTTTTT TTTTTGAGA CGGAGTTTCG
37351 CTCTTGTTGC CCAGACTGGG AGTGCAATGG CGTGATCTCG GCTCACTGCA
37401 ACCTCCGCCT CCCAGGTTCA AGCGATTCTT CTGCCTCAGC CTCCCTAGTA
37451 GCAGGGATTA CAGGCATGTG CCACCACGCC GGGCTAATTT TGTATTTTTA
37501 GTAGAGATGG GGTTTCTCCA TGTTGGTCAC GCTGGTCTCG AACTCCCGAC
37551 CTCAGGTGAT CCGCCTGCCT TGGCCTCCCA AAGTGCTGGG ATTACAGTCG
37601 TGAGCCACGG CGCCTGGCCG ATTTGCTTGT TTTTAATTAA AATAGGGGCC
37651 TTGGCCAGGT GCAGTTGTTC ACCCCTGTAA TCCCAGTACT TTGGGAGGCT
37701 GAGGCAGGCA GATCTCTTGA GTTCAGGAGT TCAAGACCAG TATGGGCAAC
37751 ATGGTGAAAC CCTGTCTCTA CCAAAACAC AAAATTCAGC CAGGCATGGT
37801 GGTGTGTCCC TGTAGTTCAA GGTACTCAGG AGGCTGAGGT GGGAGGATTG
37851 CTTGAGCCCG GAGATGGAGG TTGCGGTGAG CCAAGATTGT GCCATTTGCA
37901 CTCTAGCCTG GGCAACAGAG CGAGACCTTG TTTCAAAAAA AAAAAAGAAG
37951 AGGGTCTCAC TTTACACTTC TGTGACTGGT GTTTAAAAA TCTAAACACA
38001 GGCCGGGCAC GGTGGCTCAC GCCTGTAATC CCAGCACTTT GGGAGGCAGA
38051 GGCACGCAGA TCACAAGGTC AGGAGTTCGT GACCAGCCTG GCCAGCATGG
38101 TGAAGCCCAT CTCTACTAAA AATACAAAAA AATTAGCTGG GCATGGTGGC
38151 AGGTGCCTGT AATCCCAGCT ACTTGGGAGG CTGAGACAGG GGAATCACTT
38201 GAACCCAGGA GGCGGAGATT GCAGTGAGCC AAGATTGCGC CATTGCACTC
38251 CAGCCTGGTG ACAGAGCGAG ACTCCGTCTG AAAAAAAAAA AAAAAAATCT
38301 AAACACAAGA TTTTACTTTT AATCCTATCA TTTCCTCTTG CTTGGCTTCA
38351 GTAATCCTTC AAGTTTTCTA GGTCTTTTCA AAATCTTGAT TCTGTTGATT
38401 TATATTTTAA TTATCTTTTC CTTTCAGCTT TTCCTGTTCA GGTGTGACAT
38451 CTGGGTCTTT ATCTGAGTTT TATTAGATTA TAAAACATTC AGCAAGATAG
38501 GGCAGGTACT GAGTCCAGTT GTACACCATG GAAGGCCTCT TTCTGTGATT
38551 GTTCATTCAT GAGGCTTTAT GAAAATGTCT ACATTACACC AGGCACTTGG
38601 AGGTTACAGA GATGAATAAA ACATAGTCCA TTAGGAGGCA GACAATGGGA
38651 GAGACAAACA TGGGAAAAAG TTACTCTGAT TATGAGGAGT AATGAGAATT
38701 ACATATGAAG GAAAGTATTG TTAGTACTGT TAGGATTTAG TGTCAGGAAA
38751 GTTTTCAGAG TAGCAAGGAA ACATCAGAAA TTTTACTCTT TCTGCCAGGC
38801 ATGGTGCATG TATTATTCTG TTCTCACACT GCCACAAGGA ACTGACCAAA
38851 ACTGGGTGAT TTATTAAAAA AAAGGTTTAA TTGACTCATA GTTCTGCATG
38901 GCTGAGGAGG CCTCAGGAAA CTTACTGTGG CAGAAAGGGA AGCAGGCACG
38951 TCTTACATGG CAGGAGGCGA GAGAGTGTGA AGGAAGTGAA GGGGGAAGAG
```

FIGURE 3M

```
39001 CCCCTTATGA GACCATCAGA TCTTGTGAGA ATTCATTCAC TATCACTCGA
39051 ATGGGGAAA CCGTCGTCAT AATCCAATCA CTTCTCCATA ATCCAATCAC
39101 TTCCCTCAGT GATTACAACT TGAGATGAGA TTTGGGTGGG GACACAGAGC
39151 CAAACCATAT CAGTGCCTGT AGTCCCAGTT ACTTGGAGGC TGAGGCAGGA
39201 GGAACACTTG AGCCCAGGAG TTCAAGATCT GCCTGGGCAA CATAGCAATA
39251 CCTCCATTTT GGATAAAAAG GAAATTTTAC TTTTTGGGTG CCATTGCTTA
39301 GTTTAATCAG CTGTAACTTC TTGTTGACTT TTAGTCAAAA AACAATTTTT
39351 CCTTCTATCT TTGTGAAAGA GGTTGGTGAG CAAGGAAGAA AAGGAAACTT
39401 GCTTTATTGA GCAGCTTCTA TAGTCAGGCA CATTTTACAA ACATTAGTTC
39451 ATTTAAACCC CTTTAGCTGT TGTACAAGGT GAATGCTATC TAGCATTTAC
39501 AGATGAAGAA ACTGTTAGGT GACTCTCCCT AATATTAAAT AACCAGGAAC
39551 CTGGATTTGA TGTTTTGAAG TCAGGGTAGC TTGATCCTCG AGTTCATGCT
39601 TCCTCCAAGG ATACACTGAA AGACTTTGAG CCTCTTTTTT TTTTTTTCTC
39651 TTTTTTTGAG ACAGGATCTG GCTCTCTTGC CCAGAGTGCA GTGGTGTGAT
39701 CTCAGCTCAC TGCAACCTCT GCCTCCTGGG CTCAAGCGAT TCTGCCTCAG
39751 CCTCTCGAGT AGCTGGGACC ACAGGCGCAC GCCAGCATAC TTGGCTAATT
39801 TTTGGATTTT TAGTAGAGAC AGGGTTTCAC CATGTTGGTC AGGCTGGTCT
39851 CGAACTCCTG AGCTCGTAAT CCGCCCGTCT CGGCCCCACA AAGTGCTGGG
39901 ATTACAGGCG TGAGCCACCG ACCCAGTCCC AACAGTTTTT TAAAACCCAG
39951 AACTATAATG CAATAATGTT AGCATTTGTT TTGGGAGTTT GAGCCTAAAT
40001 GGTTGAAGTG CAGTAAATTG TTCTTAAAAT ACGTTTTATG AAAGTATTTG
40051 GAGTCTCTTC CTTACATTTT TTTCTCTAGC ATGAAGACAA CACCTAGCCA
40101 GGCATGGTGG CTCATGCCAG TAATGCCAGC ACTTTGGGAG AATGAGTTAG
40151 GATAATTGCT TGAGTCCAGG AATTTGAGAC CAGCCTGGGC AATGTAGCGA
40201 GACTCTGTCT CTACAAAAAA GAAAAAATTA GCCGGGTGTG GTGGCATGTG
40251 CCTGTAGTCC CAGCTACTCA GGAGGCTCAG GTGGAAGGAT TGCTTGAGGT
40301 GGGAGGTTGA GGCTGCAGCG AGCCATGATC ATGCCACTGT ACTCAGCCTG
40351 GATGACAGAA TGAGACGCTG CTTGAGAGGG GAAAAAAAG ACACCTGCTT
40401 GGGATGATTA AAGTTCTGTC TTGACTGGTA GTTATTGAA TTAGGTCCCT
40451 CCAGTGCTTT TAATCATGGT AGAATGTGCT AGCAAGTGAG TTTGTCTTAC
40501 ATGGAAGAGT TCTGTGTTCA AGGGCTTTCG GCCAGTGGCA TTCCTAAACA
40551 CAGTGTTAAA GGCGGTAGGG AATGTGAAAA GTATGACATA GTTCCTGCTC
40601 TCAACAGCTT GTAATTTTAG TATTATTATC GTAAGCTCAA TTGTAGGTAC
40651 TACTTCTTTT CTGGACTTTC AGGTGCTTAT TACCGTGCAA TTTAGTGGTA
40701 TGAGTTGAGG ACTAATGTTT CTATATCACA TCCTGATAAT CTCCACAGTT
40751 ATGAAAACTA AACTATTTCC CCTCCCTCCT ACACTTTTCC CCAACTTTAT
40801 TTTAATGGAA TTGTTTGGAT TTCTTGATTG TTTTGTAATA GTGGGACACA
40851 GCAGGCCAGG AAAGATTTCG AACAATCACC TCCAGTTATT ACAGAGGAGC
40901 CCATGGCATC ATAGTTGTGT ATGATGTGAC AGATCAGGTA AGTTCCAAGA
40951 GGAGATTGTG TTACAGTGAC CAAGTAGGAA GCCATTATTT GATTAATGTC
41001 AGATTCATTT ACTACTTCAT ATATAAGCCA TCAGTATTAA TTTTATGGCA
41051 GAAAACTTTG TCCACTCTCA AATATAAATG TGAATCACTT AAAAGACATT
41101 TGTTTTCCTG TAATAAATAA AAGATTAGTA ATTAGTTTTA CGTTTGCTTT
41151 CAAGGGATTC TGGTTGTATT TATTGTCAAC TAAATAACTT TGATCAAATA
41201 GCCAAGACTC TAACATATAG GCAAGAGTTT GTAGGGAATC GTGAGTTGCT
41251 TGGCTTATAC TGTGTTCTTG GTGTTAAGTA TTAACAGGAA TATGGCCTGG
41301 TAATTAGAAC TTGTCCATCA GAATTGCCAA AAGTGGGATT CGGGGGTCTC
41351 TGCCTATGGA GGATGTGGTT CAGAAATAAA GAATTTGAAT AGGATAAGCT
41401 GTAGGAGGAT CTTAGTATGA GAATGAGTAT CTGAAGATTA GCTGTGAGAG
41451 AGGGCAGAGC GATGGAGGGA ACAATGTGGG ACAGTGTGAA GCATGTGATC
41501 CAGGGGCCAT AACTTTTTTT GTTACTATTT TTTTAAATCA GAAACTTAGA
41551 TTTCAGTGTC CTTTCTATCA AAGAAAAGGA CAAAGATAA ACGTTCAAAA
41601 TTGGAATTTA TTTTTCTTTT GGCAAATGTT AAATCTCACC TCTAATGAGA
41651 AATCATAGCT AATTAGGAGA TAACTTACAT GTAAGCATTT AGATTCAGTG
41701 CCATTAGAAG TGCTGGGTGG GTGATATCTG CAGGAGAAAA AAATGATGCT
41751 AGTTTAAAAA ATCTCTACTA TTACCGTGAA ATATTTTAA ATGAAAACTT
41801 TCGTCCTCTA AATATGACTG TGGAAAAGAA AATGAGTATA TTTAATAACA
41851 TCTTTTGACA TCTCTAGTAG TAACAGTAGG TCATCTTATT CATAAACCAA
41901 AATTTTACCA AATTTCAGGC CAGGCGCAGT GGCTCATGCC TGTAATCCCA
41951 GAACTTTGGG AGGCCGAGGC GGGCGGATCA CCTGAGGTCA GGAGTTAGAG
```

FIGURE 3N

```
42001 ACTAGCCTCG CCAACATGGC AAAATCCCAT CTCTAGTAAA AATACAAAAA
42051 TTAGCCAGGC GTGGGGCCC GTGCCTGTAA TCCTAGCCAC TTGGGAGGCT
42101 GAGACAGGAG AATCGCTTGA ACCCAGCGGG CAGAGGTTGC AGTGAGCCGA
42151 GATCGCGCCA TTGCACTCCA GCCTGGATGA CAGAACAAGA CTTTGTCTCA
42201 AAAAAAAAAA AAAAAAAAAA AAAAAAATTA ATCAAATTTC AAAACCAGGT
42251 TTTGTAGTAC ATTTAAATTG CATATTCCAA AGCAGTTGGG TTTGCCTGCG
42301 TTGCAGTTTA ATATTAAGCT ATACTTCCCT TTCAAATAAG GTATTTTCAT
42351 CGTTAAGCCT GTAAATTCTA GTTTGTCATT GTTTAGATAT TTATAGTCAT
42401 TTTAATATAT CTGTTTACGG CCAGCTGCAA TGGCTAACAC CTGTAAACTC
42451 AGCACTTTTT GAGGCCAAGG TGGGCCGATT GAGCTCAGGA GTTCGAGACC
42501 AGCCTGGGCA ACATAGTGAA ACTCCATCTA TACAAAAAAT CCAAAAAAAA
42551 AAAGACAGGT GTGGTGGCAT GTGCCTGTAG TCCCAGCTAT CCCGGAGGCG
42601 GAGGCGGGAG GATGGCTTGA GCTTGGGAGG TCGAGGGTGC AGTGAGCTGT
42651 GATTGTGCCA CTGCACTCCG GCCTAGGTGA CAGAGCAAGA CCCTGTCTCA
42701 AAAAAAAAAA TCTCTTCACT CCTTAGCAGT GGTTATTTTG TAGCTAGAGT
42751 TGTCTCACTA GCTCTTTGTT ATTTGTCTGT TAGGTCAGGA ACGATGTTTC
42801 TGTTTATTCC AGAACTATAT TATCGAACTA TATTATCAGT CTTTCAAATG
42851 TCTTTTTAGG AGTCCTTCAA TAATGTTAAA CAGTGGCTGC AGGAAATAGA
42901 TCGTTATGCC AGTGAAAATG TCAACAAATT GTTGGTAGGG AACAAATGTG
42951 ATCTGACCAC AAAGAAAGTA GTAGACTACA CAACAGCGAA GGTATGTTTA
43001 AAGTTTAATT TTCATACTGA ATTTGAAGGT GTTGAATTAT GTATGGGTTC
43051 TGCAGTAACA GTAAGGCCAC AGCCTTTTAA AAATATGTGC ACTAGAATAC
43101 TGTGACAGTG ACAATTTGTG TAGCATCTGT TTGGATCCAA TGAACTTAGT
43151 TCCTCACGCT CCATTATGGA TGGTAGAAAT GCAGTAAGAA TTAGTGAAAA
43201 AGATTTTTCA GTGTTAATTG TGCCTCATTA TTCTCTTAGG AATTTGCTGA
43251 TTCCCTTGGA ATTCCGTTTT TGGAAACCAG TGCTAAGAAT GCAACGAATG
43301 TAGAACAGTC TTTCATGACG ATGGCAGCTG AGATTAAAAA GCGAATGGGT
43351 CCCGGAGCAA CAGCTGGTGG TGCTGAGAAG TCCAATGTTA AAATTCAGAG
43401 CACTCCAGTC AAGCAGTCAG GTGGAGGTTG CTGCTAAAAT TTGCCTCCAT
43451 CCTTTTCTCA CAGCAATGAA TTTGCAATCT GAACCCAAGT GAAAAAACAA
43501 AATTGCCTGA ATTGTACTGT ATGTAGCTGC ACTACAACAG ATTCTTACCG
43551 TCTCCACAAA GGTCAGAGAT TGTAAATGGT CAATACTGAC TTTTTTTTTA
43601 TTCCCTTGAC TCAAGACAGC TAACTTCATT TTCAGAACTG TTTTAAACCT
43651 TTGTGTGCTG GTTTATAAAA TAATGTGTGT AATCCTTGTT GCTTTCCTGA
43701 TACCAGACTG TTTCCCGTGG TTGGTTAGAA TATATTTTGT TTTGATGTTT
43751 ATATTGGCAT GTTTAGATGT CAGGTTTAGT CTTCTGAAGA TGAAGTTCAG
43801 CCATTTTGTA TCAAACAGTA CAAGCAGTGT CTGTCACTTT CCATGCATAA
43851 AGTTTAGTGA GATGTTATAT GTAAGATCTG ATTTGCTAGT TCTTCCTTGT
43901 AGAGTTATAA ATGGAAAGAT TACACTATCT GATTAATAGT TTCTTCATAC
43951 TCTGCATATA ATTTGTGGCT GCAGAATATT GTAATTTGTT GCACACTATG
44001 TAACAAAACA ACTGAAGATA TGTTTAATAA ATATTGTACT TATTGGAAGT
44051 AATATCAAAC TGTATGGTGA TAAGTATTGT TTTGATTCTT ATGGTTAAAG
44101 GGAAATAGAG CCTTGCATTA TATTCAACAC AGCCATTTGT GTGTGCACAA
44151 TGCAAACTAA GGTATTCTAG ACCTATCTTA GAGCAGCATC CAGTATTTGC
44201 TTTCTAGATA ATATGCCCAA TAACATGACC TAGAGGGGCT TCTGTGCTGT
44251 GTAGGGATTT AACCAACTTC AGTGGTTCAG GGAGCTCAAA CTATATGTAA
44301 AACAAGTTTA GAATGTATGC TATCTAGCCC GTTATCTCTG ATCCTTCTCT
44351 AAAACCATTT GAAATAGCTT CATTGATCAA CATTTCATAA ATGCATCTGT
44401 GGTAGAGGTA GAAAGCAGCA CCTTTCCTAA TTGGCAAATG ATCAGACTAA
44451 TGTGTGCTAA TGTTTTTCTT CCATGCTTTC AGTCAGATTC AACTATTTTA
44501 TCCTCCACAG TTGCTTAACT TGGTGTTGGA GGAGGGTTTA AGCATTAAGA
44551 TAGGAAGCAG GAAATTTGAT TGCTCTAAAT TTAGAAATTA TATCCCTAAA
44601 AATTAAAACA TGAATACTGG GTGGTAATGA TAATTGAGGC AAATGTATTT
44651 ATTTTGGTGA CATTTGCAT ATATGAAGAT TTTCTGAAAT AGGACCTTCA
44701 AGATCCTAGG GGGTTTTGTT TGGTTTTTAA TTGTGAGGAA TAAAAAATCT
44751 TCTGCCCACA CTGGCATTTT AAGGTGACTG AGGTCAAACG TTGTTTCCTT
44801 AGGTTGAAAT AGCAGCCAAA ACATTCTTCA CGCAGGGGCT TGGGATATGG
44851 CTGCTGGCAA CACATTTTGT TGTGGGCTCC TTAATTTAAT GATAAAATTT
44901 AAGCTAAACA CAAGCCAAAA ATGAATAGGT TTTTTTAATT TTTATTTTTC
44951 ACTAAACAGG CAATTGAAAT ACATGGTACA AAAATAAGTG GTAAGATAAT
```

FIGURE 30

```
45001 TGTAAAATGA AATGGACAGA ATATTCAATT TTCCATCTAT GAAAATTTCA
45051 CAATAAAAAT CATAGTTTAC TTTGTATTAT AGGCGTGCTT GGTGGATCTA
45101 TTCATCCTCA CATAAGGCAA CTGACAAATT CCTGAAGTTA CCAATAGTTA
45151 TTTTGGTGAA GATCTTTAAT GCTTCAGAAG TTTTGTTTTT GCCTTAATAC
45201 AGTATAAAGG GGGAAAGAGT TCAGAAACTA TTTTCTAAAG TAGCTAAATG
45251 ACACAAAACA AATGTCAAGA TACTGTGATG CCATGCCGTG CACTTCATTT
45301 TTACACAGTA AAAGTTGTTT AAATTGTCAG CTTATTCTTG GTGAGTTAGC
45351 GGAAACATTA CATGAACTTA AGATGAGCAT ATTTACAGAC TTAAGTTTGG
45401 AAAATTCCAG CGTTCTTTTC CCCATGGCAG TAAAGATTGG GATTTACAAC
45451 AAATTTCAGC ATGCCTTAAG ATTTGCTTCT ATGTATACGC AATAAATGT
45501 GGTTCTGGAA AAAATATATA CCCCTTTATA CCCCCATTTT CAAGTACAAA
45551 CGGTTCAAAG CTACTACAGG TTTTAATAAT CTGTTCACTT AGTAAAGGGA
45601 ATTACCACTT GTTCTAAATA TAAGGTGCTG CCATAAATTA GTTTACATAG
45651 TGAAGAAGAG TGTTCTTAAA TCTAAGCAGC TGCACACTCT GTGAAATCCT
45701 TTCAGAATGA TAGTCATTGT GGTCTGAGCA GTAATTTCCT ATTCTTCGAC
45751 CTTGGATTGA ATTTCCCTTA GCCTACATCT TGCCTTTCCA GCATATCTTA
45801 CCTCAAACCT TCTTTGTGTT CCATTCCCAC CTAAGCTTCA AAATAGCCCT
45851 GTGTTGACGT CGTCTTCCAT TTGCTGAGCT TACCTATGGA TCTCCAAGAA
45901 CCCAGATCTT GAAACTGCTG ATCCAGCTTT GAGTATCATC ACTTCCCTGT
45951 GGATTTAACT TCCATTAATT TTAAGGGACT ACTAAGTTAT TCCAGTGTGG
46001 CATCACAGTG CAGTTAGCAA GCTCAGCTAC TTGACTCTAA TTTGGCCATG   (SEQ ID NO:3)
```

FEATURES:
Start: 2181
Exon: 2181-2203
Intron: 2204-27090
Exon: 27091-27163
Intron: 27164-33853
Exon: 33854-33949
Intron: 33950-42859
Exon: 42860-42991
Intron: 42992-43239
Exon: 43240-43434
Stop: 43435

CHROMOSOME MAP POSITION:
Chromosome 2

ALLELIC VARIANTS (SNPs):

| DNA Position | Major | Minor | Domain | Protein Position | Major | Minor |
|---|---|---|---|---|---|---|
| 397 | T | - | Beyond ORF(5') | | | |
| 2326 | A | G | Intron | | | |
| 3486 | C | A | Intron | | | |
| 6651 | - | A | Intron | | | |
| 8190 | T | - | Intron | | | |
| 8281 | T | C | Intron | | | |
| 11546 | A | G | Intron | | | |
| 11670 | C | T | Intron | | | |
| 11688 | A | G | Intron | | | |
| 14938 | A | C | Intron | | | |
| 22261 | G | A | Intron | | | |
| 22852 | G | A | Intron | | | |
| 27253 | A | C | Intron | | | |
| 28098 | - | A | Intron | | | |
| 28597 | G | T | Intron | | | |
| 31431 | C | T G | Intron | | | |
| 35704 | C | T | Intron | | | |

FIGURE 3P

| | | | |
|---|---|---|---|
| 35728 | C | T | Intron |
| 36690 | C | T | Intron |
| 41002 | G | C | Intron |
| 41033 | A | G | Intron |
| 43161 | C | T | Intron |
| 43765 | A | G | Beyond ORF(3') |
| 44713 | G | T | Beyond ORF(3') |
| 44831 | C | T | Beyond ORF(3') |

Context:

DNA
Position

397    TGCTCTGTCGCCCAGGCTGGAGTGCAGTGGCCTCTCGGCCCACTGTAGCCTCCGCCTCCC
GGGTTCAAGCAATTTTCCTGCCTCAGCCTCCCGAGTAGCTGGGATTACAGGCACGCGCCA
CCATGCCTGGCTAATTTTTGTATTTTTAGTAGAGACAGTGTTTCACCATGTTGGCCAGGC
TGGTCTTGAATTCCTGACCTCGTGATCTGTCCGTTTTGGCCTCTCAAATTCCTGAGATTA
CAGGCATGAGCCACCGAGCCTGGCCAGTTTTCTGAGTTTTTATTTGAAATCAAAATAAGC
[T,-]
TTTTTTTTTTTTTAATGGGCTTTAGAGTCCAGGGTAACGAACACTTTTTGGTGCCTATT
ACTGAACCATTCAGGGTATTCCTGGGGTGGTGACCGTGTTCATTTCAGAAACCAACATGT
TCATTTCAGAAACCAAACTCGGGTAACTTTTGATAAGTTCATCAACTAAGGCCCATGGCA
GAATTTGAGGGCTAAGGGGTGTAATTAGTGTATGGGTAGAAATAAGTGCCTTCTTTCTAT
ATTTTGGCGTTGTAGGAATTTAAAGTGATTCTGCAGTAAGTCTCAGGAGACAATTTTCTT    (SEQ ID
NO:16)

2326    GCTGATTGTGTTCTAGGGGACGGAGTAGGGGAAGACGTTTGCTCTCCCGGAACAGCCTAT
CTCATTCCTTTCTTTCGATTACCCGTGGCGCGGAGAGTCAGGGCGGCGGCTGCGGCAGCA
AGGGCGGCGGTGGCGGCGGCGGCAGCTGCAGTGACATGTCCAGCATGAATCCCGAATAGT
GAGTTCAGGAGAGCACCGGTCGGCTGGGTCCGTGGGCCAGCTTGGGGGATCTTAAAGGGG
TCGAGGAGGGTTGGGGCAGAAGTCGGGGCATCGGCTGGGGTGAGGCGAGGGTGATGGGTC
[A,G]
GGAGAGGCTGGCGGCCGGGAGTCGGGCCCCATTGTCTGACGCGGAGGGGCGGCCGCGCGG
GGGAGGGGTCGGGCCGGAGGGGTGAGCCGCCCGGGCCTGGACCGGGTCAGGTTAGAGGGC
CTGACTGCGGGGCGGGTGCTGAGGAAGCCTGCCGAGGGGCCTGGGGCGGTGTGAAGGGGT
ATCTTCTCTCGGAGGCAGTGACTTTTGAAGGAGGACTTGTCTCTAAGGGGAGGGGATGGG
GTGGGAGAGCCCTTCTAGAGGGCACTGTCAGACCCTGCGCCCGCACTCTGCGGAGCTGTC    (SEQ ID
NO:17)

3486    CTGGGAACTGGTGTTCACTTCCCTTGGGTAGAGTTTGTTGGGCTCTCCTCAATGGCCCTT
TAAAAATTTCCTCTACAGTTTACATGCATGTAAAGTAATGAATAATTGGAAGAGACCGAA
TTGGTATTCCTTTTCAGTGTCAAAGGCCTTTGAGGGATGGGGGAAAATCAGTATTTGTTG
TAAAAGTTGAGTTTATTTGCTGGTTTGGTCAATTACTGCTAGACATTTTCCCCTAAAAGG
TCCACCCACCAGTTTAGCTGACTGTCATATGTGTGTCACATGGCTCTTGCAAAATGCTTA
[C,A]
AAGTTTTGTAATAGTGTGGCTTGAAGCTGAAATCTTTTGCACTAAACAGAAACCGTAGTA
TTTTATTAGAATTTCATGCTTTAGAAGTTGAGGGTAGTGTTCTTGTAGTGACATTTGCTG
TGTTGACAGTTTAAAAAAATTTTTTTTTCAAGGGCTCCAAGGACAAAGTTGGTTTTGCAC
AGTTGAACGGAGGTGAACTTGAGGTTCTTAATTTAGTAGTTTTCTTGGTAACAATAAAGA
ACATGGATTTACTGCTTTATCGAGGTTTATAGACCTCTACTGTTCAGGAAATTTTCTGAA    (SEQ ID
NO:18)

6651    TTTCAGCACATTAAGAAATGCTTAACATGGCCAGGCGCAGTGGCTCACGCCTGTAATTCT
CAGCACTTTGGGAGGCCGAGGTGGGCGGATCATTTGAGGTCATGACCAGCCTGGCCAACA
TGATGAGACACTGCCTCTACTAAAAATACAAAAATTAGCTGGGTGTGGTGGTGCACGCCT
GTAATTCCAGCTACTCAGGAACCTGAGGCAGGAGAGTCACTTGAACCTGGGAGGCGGAGG
CTGCAGTGAGTCCAGATCATGCCACTGCACTCCAGCCTGAGGGACAGAGTGAGACTCCTC
[-,A]
AAAAAAAAAAAAAAAAAAAGAAAGAAATACTTAACATTATTCTCGTGATTATTCTCATAAC
ATTTTTCATAATCCACTGGCTTCCAGTGGATTTTTTTAGTGTCAAGAAAATAATTTTGAT

FIGURE 3Q

```
               TGGTTCATCTTTAAGGAATGTGTTAAGAATAAAGCATGTCTACCTGTCTTCAGTATACCA
               GCTAACTATAGTAGGAAGAAATATAGTAGTCTACTTAGATCAACTATAATTCTTTAATGC
               AGAAAAAGTTTAAAGTATTTACCTTATTTTTAGCCCCCATCCCCTTAAGTATATCATGGC      (SEQ ID
       NO:19)

8190    AGACCGGCCTGGCCAATGTGGTGAAACCCTGCCTCTACTAAAAACACCAAATTAGCTAGG
               CGTGGTGGTGTGCGCTTGTAGTCCCAAGCTACTGAGGAGGCTGAGACAAGAGAATCGCTT
               GAATCTGGGAAAAAGAGGTTGCCGTGAGCCAAGATTGGCCACTGCACTCCAGCCTGGGTG
               ACAGAGTGAGATTCTGTCTCAAAAAAATAAAAAATAAAAATTTCCCCCTTTAATCAAATT
               AAGTTAAAATGAGGGATGTTAGACAGTTTTTAACCATCAAATATTTTAGTTTAGTTTTTT
               [T,-]
               TTTTTAACGTTGTCTTAAAGATGGAAGTGCTTCAAAATCAAATCTTCCTTGCCAGTTCTC
               TACTTGGCTTCTTTTTTTTTCTTTTTGAGATAGAGTCTCACTTTGTCACTGGAGTGCGTT
               GGCGTGATCTCGGCTCACTGCAACCTCCGCCTTCCAGGTTTAAGTGATTCTTCCACCTCA
               GCCTCTCAAGTAGCTGGGAGTACAGGTGTGTGCCACCACACCCGGCTAATTTTTGTAGTT
               TTAGTAGAGACAGGGTTTCACTATGTTGGCCAGGCTGGCCTCAAACTCCTGACCTCGTGA      (SEQ ID
       NO:20)

8281    CTGAGGAGGCTGAGACAAGAGAATCGCTTGAATCTGGGAAAAAGAGGTTGCCGTGAGCCA
               AGATTGGCCACTGCACTCCAGCCTGGGTGACAGAGTGAGATTCTGTCTCAAAAAAATAAA
               AAATAAAAATTTCCCCCTTTAATCAAATTAAGTTAAAATGAGGGATGTTAGACAGTTTTT
               AACCATCAAATATTTTAGTTTAGTTTTTTTTTTTAACGTTGTCTTAAAGATGGAAGTGC
               TTCAAAATCAAATCTTCCTTGCCAGTTCTCTACTTGGCTTCTTTTTTTTTCTTTTTGAGA
               [T,C]
               AGAGTCTCACTTTGTCACTGGAGTGCGTTGGCGTGATCTCGGCTCACTGCAACCTCCGCC
               TTCCAGGTTTAAGTGATTCTTCCACCTCAGCCTCTCAAGTAGCTGGGAGTACAGGTGTGT
               GCCACCACACCCGGCTAATTTTTGTAGTTTTAGTAGAGACAGGGTTTCACTATGTTGGCC
               AGGCTGGCCTCAAACTCCTGACCTCGTGATCCACCCACCTCAGCCAAATTGCTGGGATTA
               CTTGTGTGAGCCACGCGCCTGGCTTCTACTTGGCTTTTAAAGGGAATTTTGCTTTCTGAG      (SEQ ID
       NO:21)

11546   GTTACATTTAACCCATTTATGGTCGTGTAGCCATACTCACGTTACATTTGATGCATCTGC
               TCCCTTTGTGTCTATATACTCATATAACATTTTGCATAAAGTTATAGGCAGTTCACACCA
               AGGCTGTTCATGAACCTCAGATTAAGAATACTTGATTTAGGAGATTGAAAACAGAAAAGA
               GAATGTTAACTATCATTATCAATATTAAAATGTGAAAATCTGAGAGTGACAAAGCTTAGC
               TTTTAAATCTGGTATCCCAAACTCATTTGAGTTTTTTTTTTTTTTTTTTTTTTTGAGAC
               [A,G]
               AGGTGTCGCTTTGTCCCCCAGGCTGGAGTGTAGTGGTGTGATCTTGGCTCACTGCAACCT
               CCACCTCCCAGGTTCAAGTGATTCTCCTGCCTCAGCCTCTGAAGTTGCTGGGATTACAGG
               CTGCGCCACCACGCCCAGCTAATTTTTTGTATTTATAGTAAAGACGGAGTTTCACCTTAT
               TGGCCAGGCTGGTCTCAAACTCCTGATCTTGTGATCCTCCCGCCTCGGCCTCCCAAAGTG
               CTGGGATTACAGGTGTGAGCCACTGTTCCCGGCCTAATTTGAGTTTTAAAATGTGGAGTT      (SEQ ID
       NO:22)

11670   TGTTCATGAACCTCAGATTAAGAATACTTGATTTAGGAGATTGAAAACAGAAAAGAGAAT
               GTTAACTATCATTATCAATATTAAAATGTGAAAATCTGAGAGTGACAAAGCTTAGCTTTA
               AATCTGGTATCCCAAACTCATTTGAGTTTTTTTTTTTTTTTTTTTTTTTTGAGACAAGG
               TGTCGCTTTGTCCCCCAGGCTGGAGTGTAGTGGTGTGATCTTGGCTCACTGCAACCTCCA
               CCTCCCAGGTTCAAGTGATTCTCCTGCCTCAGCCTCTGAAGTTGCTGGGATTACAGGCTG
               [C,T]
               GCCACCACGCCCAGCTAATTTTTTGTATTTATAGTAAAGACGGAGTTTCACCTTATTGGC
               CAGGCTGGTCTCAAACTCCTGATCTTGTGATCCTCCCGCCTCGGCCTCCCAAAGTGCTGG
               GATTACAGGTGTGAGCCACTGTTCCCGGCCTAATTTGAGTTTTAAAATGTGGAGTTTAAG
               ATGTTAGTCTTAAAGTGGGTTAGATGAAATTTATAAAAATAGTCAAATAGCTAAATTTAT
               AAAAGGCCATTTGAAACAATTTTGTGAAATATATAATGTGGATAATTATGTAGTGCTTTA      (SEQ ID
       NO:23)

11688   TAAGAATACTTGATTTAGGAGATTGAAAACAGAAAAGAGAATGTTAACTATCATTATCAA
               TATTAAAATGTGAAAATCTGAGAGTGACAAAGCTTAGCTTTAAATCTGGTATCCCAAACT
               CATTTGAGTTTTTTTTTTTTTTTTTTTTTTTTTGAGACAAGGTGTCGCTTTGTCCCCCAG
```

FIGURE 3R

|  | GCTGGAGTGTAGTGGTGTGATCTTGGCTCACTGCAACCTCCACCTCCCAGGTTCAAGTGA |
|---|---|
|  | TTCTCCTGCCTCAGCCTCTGAAGTTGCTGGGATTACAGGCTGCGCCACCACGCCCAGCTA |
|  | [A,G] |
|  | TTTTTTGTATTTATAGTAAAGACGGAGTTTCACCTTATTGGCCAGGCTGGTCTCAAACTC |
|  | CTGATCTTGTGATCCTCCCGCCTCGGCCTCCCAAAGTGCTGGGATTACAGGTGTGAGCCA |
|  | CTGTTCCCGGCCTAATTTGAGTTTTAAAATGTGGAGTTTAAGATGTTAGTCTTAAAGTGG |
|  | GTTAGATGAAATTTATAAAAATAGTCAAATAGCTAAATTTATAAAAGGCCATTTGAAACA |
| NO:24) | ATTTTGTGAAATATATAATGTGGATAATTATGTAGTGCTTTATGTGTAGATTGGTGGTTA (SEQ ID |
| 14938 | CATGGTAGTGTGCACCTGTAGTCCCAACCACTTGGGAGGCTGAGGTGGGAGGATTGCCTG |
|  | AGGCCAGGAGTTTGAGACCTGGGCAGCATATGAAGACCCTGTCTCTAAAAAAACTAAAAAT |
|  | AAAAAATAGCCAGGTGTGGTTGGTGTGCTTGTGGTCCCAGCTACTCAAGAGGCTGAGGCA |
|  | AGAGGGTTGCTTGAGCCCAGAAGTTGGAGGCTGCCGTGAACTGTGATTGCACCACTGCAC |
|  | TTCAGCCTGGGTGACATAGCAAGACCCTGTCTCTGTGGTGGTGGTGGGTGGGGGTGGGGG |
|  | [A,C] |
|  | AGGGATTTAAGAAGGGTTTGTGAGGTATGTATTATTTATAAATGGGCTTTTAACTTTACC |
|  | CTTCACATCTTGGGTTGAAATTAATTGTATCCATTCTCAGTTTTTCTGTCTTGCTATATA |
|  | TTTAAACTTGGAGACTTAGAGGTCATGGATGTCTTTCTATGAAAAGCAAATGAAGCAGAG |
|  | GGCTGCCTTCTCTTGCTGTAGAGGGCACACTTGCTGCAGAGCATGTTACTGTTTTATGCA |
| NO:25) | TTGCTAGGCTTTGGGAGTTGTGACTTGTATGATCATAGTACTTACAACTATTAGTTGGCA (SEQ ID |
| 22261 | CACCCACAGATAGCTATGTCAAACGTAAGGGTGGAGAAACACAGACCCCAAACTTCTCGA |
|  | GGGTAGAAAATATGAGGTTATAGTAGATTAGAACTACAAAAAGCTAGAGGAAGTTCTGAA |
|  | CTGGAAACAGTGGATAGGATTTACTAGAATAATTTACGAGGGTGACAATTGTAAATCTTC |
|  | ATAGGTTTCTTTTTTTTCCTTTCTCTTTTTTTTTTTGAGATGGAGTCTCGCTCTGTTG |
|  | CCCAGGCTGGAGTGCAATGGCGCAGTCTCTCCTCACTGCAACCTCCGCCTCCTGGGTCCA |
|  | [G,A] |
|  | GTGATTCTCCTGCCTTAGCCACCCAAGTAGCTGGGATTACAGGCATCTGCCACCATGCTG |
|  | AGCTAATTTTTGTATTTTTTTTTTAGTAGAGACGGGGTTTCACCATGTTGGTCAGGCTG |
|  | GTCTTGAACTCCTGACCTCAGGTAATCCACCCACCTTGGCCTCCCAAAGTGCTGGGATTA |
|  | CAGGTGTGAGCCACCGCGCCCAGCCAAATTTTTATTGGTTTCTAAACTAGCGTAATTTAG |
| NO:26) | TTTTTTTCACTTAAGTCAAAATTATATTATTGTAGGATAAAAACTTAGTGATCCAAATTC (SEQ ID |
| 22852 | ATCCAAATTCATGAGGAATGAAGAATAAATACATTTAAAGTCTTACCATTTGCTAAATTA |
|  | GTCTTGGCTCTTTGTACCAAAATTCTGTCCTTGTGCTCTGTAATTTTATATTTGTATATT |
|  | TTCTATCAACATTTTTACTGTGTGGTGTTTTGTAAATTATAAAAACGTTTTAAAGCAAAC |
|  | TCAGAACAATGAATTCTCACGAATATTCAGTATATTTACAGTTGAGAAATAAAACTACTTC |
|  | TGTAGTAGGTAATTTAAAATGTCCCAATGCAAGTTAACGTGTCACTGATCACGCTATTCA |
|  | [G,A] |
|  | GTGTGTGTCTTTGATAAGGGGAGGTGGGGAAGTTTGTGGGTTTGATTTTATTTGCCTTTC |
|  | TCATGTGACTGTTGTCATGTTAGTAAACAAATGGTTTGCGAGAGAACCAGTAGTCTTTTG |
|  | CAAAGATTGTCTTATACAGAGCACTCAATTCTTCATATTATTTATAATGGCTTTAATTTA |
|  | AGCCTTAAATTATTAGAAACTCATAAATAATTTTTTTATTTGTTTTTTTGAGATGGAGTT |
| NO:27) | TCGCCCTTATTGTCCAGGCTGAAGTACAATGATGTGATCTTGACTCACTGCAACCTCCGC (SEQ ID |
| 27253 | GCTTAAGCCATGCATGGGCTTTATAGGAGATGTAGTCTTCACAGTGAGTTGTTATTTGTA |
|  | GCTGTGTTTTTGTTTTTGTATAGCTTATAGCAATGCAGTGTGCTTTTTATTAACATCATT |
|  | TTCTTTTTCTTTTTGCAGTGATTATTTATTCAAGTTACTTCTGATTGGCGACTCAGGGGT |
|  | TGGAAAGTCTTGCCTTCTTCTTAGGTTTGCAGTAAGTTGAAATTGAAATGTCTTTACAAT |
|  | TAATGGTACAATTAATGCTATGTATGTTTTCTAGGTAGATAAAATTAAACAGTTTTATTC |
|  | [A,C] |
|  | GAATAAGTTAATTCTTCCAGAATTTATATATTTAAAGACTCCAAATATACATCCCCAGTG |
|  | GTATCTTGGACTGTTAAATAGAAAAATATTGTTGCTCTTAAAAGAAATTCAGTGAAGTCT |
|  | GGTTATAAAGTCAGAATGTCTAATACTTTTGGTCAGAGTCAAACAGCAGTTCCAATATAG |
|  | GCAGCAAGTTAAAGGGGTAGTTGGTGGCCTGTGTTGAAAGCGACTTGATGAAAATAAATC |

FIGURE 3S

|  | TTTAAATTAAACTTTAGTAGAATAAAAAGAAAAAGCAGAGCCAGGTGACGCAGTGGATCA | (SEQ ID |
| --- | --- | --- |
| NO:28) | | |
| 28098 | CTTTAAATTTAGCATGTTTCCTGGCCAGGTGCGGTGGCTCACGCCTGTAATCCCAGCACT<br>TTGGGAGGCCGAGACGGGCGGATCACAAGGTCAAGAGATTGAGACCATCCTGGCTAACAC<br>GGTGAAACCCCGTCTCTACTAAAAATACAAAAAATCAGCTGGGTGTGGTGCCACACGCCT<br>GTAGTCCCAGCTACTCGGGAGGCTGAGGCAGGAGAATCGCTTGAACCCAGGAGGCGGAGG<br>TTGCAGTGAGCTGAGATGGTGCCACTGCACTCCAGCCTGGCAACAGAGCAAGACTGTCTC<br>[-,A]<br>AAAAAAAAAGAAAAAAAATAAAAAAACAAATTAGCATGTTTCCCTTCTAGAGATCATTGT<br>TTCTCAGAGCATGGACCAAAGACTCCTGGGGGTTACCAAGACCCTCTCAGGTAGCCCATG<br>AGGTCAAAATATCCTAATAATACTAAGATGTTAGTATTTGTAAGGAAATATTTACTTGGT<br>AATAATACTAATATAAAAGATGTTTGCGTTTTTCAGTGATGACATTGGCTCTGGTACAAA<br>AGCATGTGGGTAAAATTGCTGCTGGCTTGGTACACATCAAGGCAGCGCTAAGCTCCAAAT | (SEQ ID |
| NO:29) | | |
| 28597 | GATGTTTGCGTTTTTCAGTGATGACATTGGCTCTGGTACAAAAGCATGTGGGTAAAATTG<br>CTGCTGGCTTGGTACACATCAAGGCAGCGCTAAGCTCCAAATTGTACTCATGGTGATGGC<br>ATTCTTTACCTCTGTGCCCTCACAGGAACAAAAACAAGCCGTGCCATTTTTATTGAAGAT<br>TGTCCTTGACAAAACAGTTAAAATGATTAATTTTTGAAAAATGTTGATCCATGAGTATTC<br>CTTTAAAAATATTTGTGAAGAAATGGGAAGTTCACATAAAACAATGTTTTTTTTTTGTTT<br>[G,T]<br>TTTTTTTTTTTTTTTTTGAGACAGATTCTGGCTGTGTTGCCAAGGCTAGAGTGCAGTGGC<br>GTCTGGCTCCCAGGCTCAAGCTGTTCTCCCACTTCAGCCTCCCAAGTGGCTGGGACCTCC<br>CAAGTGGATGCGCCATCATGCCTGGCTGATTTTTGTATTTTTTGTAGTGACAAGGTCTC<br>ACTGTGTTGCACAGGCTGGTCTCAAACTTCTGAGCTCAAGCGATGCATGTGCCTCAGCCT<br>CCCAAAGTGCTGGAGAAAGCACTTTTTACTGCATACTGGCTAGTGTGTTGGTTATTTTGG | (SEQ ID |
| NO:30) | | |
| 31431 | CTGCATTTTTTTTTTTTTTTGGTTTGAGATGGAGTCTCGCTCTGTCGCCCAGGCTGGA<br>GTGCAGTCGTGCAATCTCGGCTCACTGCAGCCTCCACCTCATGGGTTCAAGCGATTCTCC<br>ATCTTGGTCTCCTGACTAGCTAGGTTTACAGGCGTGTGCCATCACACCCACTAATTTTTT<br>GTATTTTTAGTAGAGACAGGGTTTCACCATGTTGGCCAGGCTGGTCTTGAACTCCTGATC<br>TAAAGTGAGCCTCCCACCTTGGCCTCCCAAAGTGCTGGGATTACATATGTGAGCCACTGC<br>[C,T,G]<br>CCTGGCCTCTATATACTTCTATAGTACCTGATACTTATTAGGCACTCAATTACAACATAA<br>CTTTTTTTTTTTTTTTTTTTGAGACAGAGACATGCCTTGTCGCCTGGGCTGGAGTGC<br>AGTGGCACAGTCTCGGCTCACTGCAACCTTCACCTCCCGGGTTCAAGTGATTCTCCTTCC<br>TCAGCCTCCCGGGTAGCTGGGATTACAGGCGCCCGCCACCACGTCCAGCTAATTTTTTGT<br>ATTTTTAATAGAGATGAGGTTTCACCATCTTGGCCAGGCTGATCTCAAACTCCTGACCTT | (SEQ ID |
| NO:31) | | |
| 35704 | ATGTGTGATCATTGGTGTTTATAAGATTTGGGTGTGTATTCGTGTGTGAAACATTCATAT<br>TTTGTTACTTTCCTGTGGCTGGAAGGGATCTTATAGGACACTGTCTTTCATCTTTGTCTG<br>TCTTTCATCTTTAATAGGAATTTCTTTTCCATGCCTGAAGGCCTCATTTTGAACATTTTG<br>TTTGTTTGTTTTTTTATTTTTTGAGATACAGTATTGCTCTGTCTCCCAGGCTGGAGTGCA<br>GTGGCGCGATTTGAGCTCACTGCAACCTCCGCCTCCTGGGTTCAAGTGATTCTCCTGCCT<br>[C,T]<br>AGCCTCCCTAATAGCTGGGATTACATGTGTGTACCACCATGCCCGGACAATTTTTTTTTT<br>TTTGAGATGGAGCCTTGCTTTGTCGCCCAGGCTGGAGTGCAGTGGTGCAATCTTGGCTC<br>GCTGCAGCCTCCGCCTCCCAGGTTCAAGCAGTTCTCTTGCCTCAGCCTCCTGAGTAGCTG<br>GGATTACAGGCGTGCGCCACCACACCCTGCTAATTTTTGTATTTTTAGTAGAGACAGAG<br>TTTCACCATGTTGGTTAGGCTGGTCTCGAACTCCTGACCTCGTGATCTGCCTGACTCGGC | (SEQ ID |
| NO:32) | | |
| 35728 | GATTTGGGTGTGTATTCGTGTGTGAAACATTCATATTTTGTTACTTTCCTGTGGCTGGAA<br>GGGATCTTATAGGACACTGTCTTTCATCTTTGTCTGTCTTTCATCTTTAATAGGAATTTC<br>TTTTCCATGCCTGAAGGCCTCATTTTGAACATTTTGTTTGTTTGTTTTTTATTTTTTGA<br>GATACAGTATTGCTCTGTCTCCCAGGCTGGAGTGCAGTGGCGCGATTTGAGCTCACTGCA<br>ACCTCCGCCTCCTGGGTTCAAGTGATTCTCCTGCCTCAGCCTCCCTAATAGCTGGGATTA | |

FIGURE 3T

```
            [C,T]
            ATGTGTGTACCACCATGCCCGGACAATTTTTTTTTTTTGAGATGGAGCCTTGCTTTGTC
            GCCCAGGCTGGAGTGCCAGTGGTGCAATCTTGGCTCGCTGCAGCCTCCGCCTCCCAGGTT
            CAAGCAGTTCTCTCTTGCCTCAGCCTCCTGAGTAGCTGGGATTACAGGCGTGCGCCACCACA
            CCCTGCTAATTTTTTGTATTTTTAGTAGAGACAGAGTTTCACCATGTTGGTTAGGCTGGT
            CTCGAACTCCTGACCTCGTGATCTGCCTGACTCGGCTTCCCAAAGTGCTGGGATTACAGG       (SEQ ID
NO:33)

36690       AAAAAAAAAAAAAAAAAGTAACCAGGTGTGGTGGTCCATGCCTGTAGTCCTAGCTCCCCAG
            GAGACTGAGGTGGGAGGAATGTTTGAGCCCAGGACTTCAAGGCTGCAGTGAGGCAAGATT
            GCACCATTGCACCCCAGCTTTGGGGACAGAGTGAGAGACCCTGTCTCAAAAACAAAATAA
            GGCTGGGCGCAGTGGCTGTCCGGGCGTCGTGGTTCACGCTTATAGTCCTAGCACTTTGGG
            AGGCCAAGGTGGGCAGATTGCCTGAGCTCAGGAGGTCTAAGACCAGCCTGAGCAACATGG
            [C,T]
            GAAACCTCATCTTTGCAAAACATACAGAAAAAAACAAAAAAAACCACAAAACCTCTAGTT
            GCCAGTTATTTTTTTTATTTATTCCTAGTGATTCTTCTTTTTTTCTTTTTTCTGAGACAA
            AAATTTCACTTTGTCTCCCTCGCTAGAGTGCAGCGGTCAGCTCACTACATGATTCTTTTA
            GAGACATGTTAATTCTTTATATTGAGCTGAAGCCTGTTTCTTTTACTTCTGTCTCTTCTT
            ATTCCTCCGCCTTGTAGAGCTGCCTGAATCAGATTAATTCCTCTTTTATTGGCAAGCCTG       (SEQ ID
NO:34)

41002       GAGTTGAGGACTAATGTTTCTATATCACATCCTGATAATCTCCACAGTTATGAAAACTAA
            ACTATTTCCCCTCCCTCCTACACTTTTCCCCAACTTTATTTTAATGGAATTGTTTGGATT
            TCTTGATTGTTTTGTAATAGTGGGACACAGCAGGCCAGGAAAGATTTCGAACAATCACCT
            CCAGTTATTACAGAGGAGCCCATGGCATCATAGTTGTGTATGATGTGACAGATCAGGTAA
            GTTCCAAGAGGAGATTGTGTTACAGTGACCAAGTAGGAAGCCATTATTTGATTAATGTCA
            [G,C]
            ATTCATTTACTACTTCATATATAAGCCATCAGTATTAATTTTATGGCAGAAAACTTTGTC
            CACTCTCAAATATAAATGTGAATCACTTAAAAGACATTTGTTTTCCTGTAATAAATAAAA
            GATTAGTAATTAGTTTTACGTTTGCTTTCAAGGGATTCTGGTTGTATTTATTGTCAACTA
            AATAACTTTGATCAAATAGCCAAGACTCTAACATATAGGCAAGAGTTTGTAGGGAATCGT
            GAGTTGCTTGGCTTATACTGTGTTCTTGGTGTTAAGTATTAACAGGAATATGGCCTGGTA       (SEQ ID
NO:35)

41033       CTGATAATCTCCACAGTTATGAAAACTAAACTATTTCCCCTCCCTCCTACACTTTTCCCC
            AACTTTATTTTAATGGAATTGTTTGGATTTCTTGATTGTTTTGTAATAGTGGGACACAGC
            AGGCCAGGAAAGATTTCGAACAATCACCTCCAGTTATTACAGAGGAGCCCATGGCATCAT
            AGTTGTGTATGATGTGACAGATCAGGTAAGTTCCAAGAGGAGATTGTGTTACAGTGACCA
            AGTAGGAAGCCATTATTTGATTAATGTCAGATTCATTTACTACTTCATATATAAGCCATC
            [A,G]
            GTATTAATTTTATGGCAGAAAACTTTGTCCACTCTCAAATATAAATGTGAATCACTTAAA
            AGACATTTGTTTTCCTGTAATAAATAAAAGATTAGTAATTAGTTTTACGTTTGCTTTCAA
            GGGATTCTGGTTGTATTTATTGTCAACTAAATAACTTTGATCAAATAGCCAAGACTCTAA
            CATATAGGCAAGAGTTTGTAGGGAATCGTGAGTTGCTTGGCTTATACTGTGTTCTTGGTG
            TTAAGTATTAACAGGAATATGGCCTGGTAATTAGAACTTGTCCATCAGAATTGCCAAAAG       (SEQ ID
NO:36)

43161       AGTCCTTCAATAATGTTAAACAGTGGCTGCAGGAAATAGATCGTTATGCCAGTGAAAATG
            TCAACAAATTGTTGGTAGGGAACAAATGTGATCTGACCACAAAGAAAGTAGTAGACTACA
            CAACAGCGAAGGTATGTTTAAAGTTTAATTTTCATACTGAATTTGAAGGTGTTGAATTAT
            GTATGGGTTCTGCAGTAACAGTAAGGCCACAGCCTTTTAAAAATATGTGCACTAGAATAC
            TGTGACAGTGACAATTTGTGTAGCATCTGTTTGGATCCAATGAACTTAGTTCCTCACGCT
            [C,T]
            CATTATGGATGGTAGAAATGCAGTAAGAATTAGTGAAAAAGATTTTTCAGTGTTAATTGT
            GCCTCATTATTCTCTTAGGAATTTGCTGATTCCCTTGGAATTCCGTTTTTGGAAACCAGT
            GCTAAGAATGCAACGAATGTAGAACAGTCTTTCATGACGATGGCAGCTGAGATTAAAAAG
            CGAATGGGTCCCGGAGCAACAGCTGGTGGTGCTGAGAAGTCCAATGTTAAAATTCAGAGC
            ACTCCAGTCAAGCAGTCAGGTGGAGGTTGCTGCTAAAATTTGCCTCCATCCTTTTCTCAC       (SEQ ID
NO:37)
```

FIGURE 3U

43765  AATGAATTTGCAATCTGAACCCAAGTGAAAAAACAAAATTGCCTGAATTGTACTGTATGT
AGCTGCACTACAACAGATTCTTACCGTCTCCACAAAGGTCAGAGATTGTAAATGGTCAAT
ACTGACTTTTTTTTATTCCCTTGACTCAAGACAGCTAACTTCATTTTCAGAACTGTTTT
AAACCTTTGTGTGCTGGTTTATAAAATAATGTGTGTAATCCTTGTTGCTTTCCTGATACC
AGACTGTTTCCCGTGGTTGGTTAGAATATATTTTGTTTTGATGTTTATATTGGCATGTTT
[A,G]
GATGTCAGGTTTAGTCTTCTGAAGATGAAGTTCAGCCATTTTGTATCAAACAGCACAAGC
AGTGTCTGTCACTTTCCATGCATAAAGTTTAGTGAGATGTTATATGTAAGATCTGATTTG
CTAGTTCTTCCTTGTAGAGTTATAAATGGAAAGATTACACTATCTGATTAATAGTTTCTT
CATACTCTGCATATAATTTGTGGCTGCAGAATATTGTAATTTGTTGCACACTATGTAACA
AAACAACTGAAGATATGTTTAATAAATATTGTACTTATTGGAAGTAATATCAAACTGTAT  (SEQ ID
NO:38)

44713  AAGCAGCACCTTTCCTAATTGGCAAATGATCAGACTAATGTGTGCTAATGTTTTTCTTCC
ATGCTTTCAGTCAGATTCAACTATTTTATCCTCCACAGTTGCTTAACTTGGTGTTGGAGG
AGGGTTTAAGCATTAAGATAGGAAGCAGGAAATTTGATTGCTCTAAATTTAGAAATTATA
TCCCTAAAAATTAAAACATGAATACTGGGTGGTAATGATAATTGAGGCAAATGTATTTAT
TTTGGTGACATTTTGCATATATGAAGATTTTCTGAAATAGGACCTTCAAGATCCTAGGGG
[G,T]
TTTTGTTTGGTTTTTAATTGTGAGGAATAAAAAATCTTCTGCCCACACTGGCATTTTAAG
GTGACTGAGGTCAAACGTTGTTTCCTTAGGTTGAAATAGCAGCCAAAACATTCTTCACGC
AGGGGCTTGGGATATGGCTGCTGGCAACACATTTTGTTGTGGGCTCCTTAATTTAATGAT
AAAATTTAAGCTAAACACAAGCCAAAAATGAATAGGTTTTTTTAATTTTTATTTTTCACT
AAACAGGCAATTGAAATACATGGTACAAAAATAAGTGGTAAGATAATTGTAAAATGAAAT  (SEQ ID
NO:39)

44831  GGAGGGTTTAAGCATTAAGATAGGAAGCAGGAAATTTGATTGCTCTAAATTTAGAAATTA
TATCCCTAAAAATTAAAACATGAATACTGGGTGGTAATGATAATTGAGGCAAATGTATTT
ATTTTGGTGACATTTTGCATATATGAAGATTTTCTGAAATAGGACCTTCAAGATCCTAGG
GGGTTTTGTTTGGTTTTTAATTGTGAGGAATAAAAAATCTTCTGCCCACACTGGCATTTT
AAGGTGACTGAGGTCAAACGTTGTTTCCTTAGGTTGAAATAGCAGCCAAAACATTCTTCA
[C,T]
GCAGGGGCTTGGGATATGGCTGCTGGCAACACATTTTGTTGTGGGCTCCTTAATTTAATG
ATAAAATTTAAGCTAAACACAAGCCAAAAATGAATAGGTTTTTTTAATTTTTATTTTTCA
CTAAACAGGCAATTGAAATACATGGTACAAAAATAAGTGGTAAGATAATTGTAAAATGAA
ATGGACAGAATATTCAATTTTCCATCTATGAAAATTTCACAATAAAAATCATAGTTTACT
TTGTATTATAGGCGTGCTTGGTGGATCTATTCATCCTCACATAAGGCAACTGACAAATTC  (SEQ ID
NO:40)

FIGURE 3V

SEQUENCE LISTING

<160> NUMBER OF SEQ ID NOS: 4

<210> SEQ ID NO 1
<211> LENGTH: 1405
<212> TYPE: DNA
<213> ORGANISM: Human

<400> SEQUENCE: 1

```
aagcgatagc tgagtgcggc ggctgctgat tgtgttctag gggacggagt agggaagac      60 gtttgctctc ccggaacagc ctatctcatt cctttctttc gattacccgt ggcgcggaga    120
gtcagggcgg cggctgcggc agcaagggcg gcggtggcgg cggcggcagc tgcagtgaca    180
tgtccagcat gaatcccgaa tatgattatt tattcaagtt acttctgatt ggcgactcag    240
gggttggaaa gtcttgcctt cttcttaggt ttgcagatga tacatataca gaaagctaca    300
tcagcacaat tggtgtggat ttcaaaataa gaactataga gttagacggg aaaacaatca    360
agcttcaaat agagtccttc aataatgtta aacagtggct gcaggaaata gatcgttatg    420
ccagtgaaaa tgtcaacaaa ttgttggtag ggaacaaatg tgatctgacc acaaagaaag    480
tagtagacta cacaacagcg aaggaatttg ctgattccct tggaattccg ttttggaaa     540 ccagtgctaa gaatgcaacg aatgtagaac agtctttcat gacgatggca gctgagatta    600
```

```
aaaagcgaat gggtcccgga gcaacagctg gtggtgctga gaagtccaat gttaaaattc    660
agagcactcc agtcaagcag tcaggtggag gttgctgcta aaatttgcct ccatccttt    720 ctcacagcaa tgaatttgca atctgaaccc aagtgaaaaa acaaaattgc ctgaattgta    780
ctgtatgtag ctgcactaca acagattctt accgtctcca caaggtcag agattgtaaa    840 tggtcaatac tgactttttt tttattccct tgactcaaga cagctaactt cattttcaga    900
actgttttaa acctttgtgt gctggtttat aaaataatgt gtgtaatcct tgttgctttc    960
ctgataccag actgtttccc gtggttggtt agaatatatt tgttttgat gtttatattg   1020 gcatgtttag atgtcaggtt tagtcttctg aagatgaagt tcagccattt tgtatcaaac   1080
agcacaagca gtgtctgtca ctttccatgc ataaagttta gtgagatgtt atatgtaaga   1140
tctgatttgc tagttcttcc ttgtagagtt ataaatggaa agattacact atctgattaa   1200
tagtttcttc atactctgca tataatttgt ggctgcagaa tattgtaatt tgttgcacac   1260
tatgtaacaa aacaactgaa gatatgttta ataaatattg tacttattgg aagtaaaaaa   1320
aaaaaaaaaa aaaaaaaaaa aaaaaaaaaa aaaaaaaaaa aaaaaaaaaa aaaaaaaaaa   1380
aaaaaaaaaa aaaaaaaaaa aaaaa                                         1405

<210> SEQ ID NO 2
<211> LENGTH: 173
<212> TYPE: PRT
<213> ORGANISM: Human

<400> SEQUENCE: 2

Met Ser Ser Met Asn Pro Glu Tyr Asp Tyr Leu Phe Lys Leu Leu Leu
1               5                   10                  15

Ile Gly Asp Ser Gly Val Gly Lys Ser Cys Leu Leu Leu Arg Phe Ala
            20                  25                  30

Asp Asp Thr Tyr Thr Glu Ser Tyr Ile Ser Thr Ile Gly Val Asp Phe
        35                  40                  45

Lys Ile Arg Thr Ile Glu Leu Asp Gly Lys Thr Ile Lys Leu Gln Ile
    50                  55                  60

Glu Ser Phe Asn Asn Val Lys Gln Trp Leu Gln Glu Ile Asp Arg Tyr
65                  70                  75                  80

Ala Ser Glu Asn Val Asn Lys Leu Leu Val Gly Asn Lys Cys Asp Leu
                85                  90                  95

Thr Thr Lys Lys Val Val Asp Tyr Thr Thr Ala Lys Glu Phe Ala Asp
            100                 105                 110

Ser Leu Gly Ile Pro Phe Leu Glu Thr Ser Ala Lys Asn Ala Thr Asn
        115                 120                 125

Val Glu Gln Ser Phe Met Thr Met Ala Ala Glu Ile Lys Lys Arg Met
    130                 135                 140

Gly Pro Gly Ala Thr Ala Gly Gly Ala Glu Lys Ser Asn Val Lys Ile
145                 150                 155                 160

Gln Ser Thr Pro Val Lys Gln Ser Gly Gly Gly Cys Cys
                165                 170

<210> SEQ ID NO 3
<211> LENGTH: 46050
<212> TYPE: DNA
<213> ORGANISM: Human
<220> FEATURE:
<221> NAME/KEY: misc_feature
<222> LOCATION: (1)...(46050)
<223> OTHER INFORMATION: n = A,T,C or G
```

<400> SEQUENCE: 3

```
ttttgggtgt gtgtgtgtgt gtgtgtgtgt gtgcctttac tagtgactca ggtcacagtt      60
ttctgagatt ttttttctcc cctcaagaca gaatcttgct ctgtcgccca ggctggagtg     120
cagtggcctc tcggcccact gtagcctccg cctcccgggt tcaagcaatt ttcctgcctc     180
agcctcccga gtagctggga ttacaggcac gcgccaccat gcctggctaa ttttttgtatt    240
tttagtagag acagtgtttc accatgttgg ccaggctggt cttgaattcc tgacctcgtg     300
atctgtccgt tttggcctct caaattcctg agattacagg catgagccac cgagcctggc     360
cagttttctg agttttttatt tgaaatcaaa ataagctttt tttttttttt taatgggctt    420
tagagtccag ggtaacgaac acttttggt gcctattact gaaccattca gggtattcct      480
ggggtggtga ccgtgttcat ttcagaaacc aacatgttca tttcagaaac caaactcggg     540
taactttga taagttcatc aactaaggcc catggcagaa tttgagggct aagggggtgta    600
attagtgtat gggtagaaat aagtgccttc tttctatatt ttggcgttgt aggaatttaa     660
agtgattctg cagtaagtct caggagacaa ttttcttagt tcttagaagt tggaagataa     720
actttggaca atgtattaca ctatgccctt tgtaattaaa taactcaaga taatgtgtta    780
aagtttagcg gagatttaaa ttcctgagct gattaaagag agctgttaag gccataggtt     840
ttttaaaaat gagttaatat tactcccaga aattgtaggc actatatagt gatgaattgc     900
atattttat tgcttattat tttccagtct tgcagaatgg ctcagggtta gtagcaacta      960
aaagataata cattacaatt caacctgaag gccgggacga aggtaggaat tggattttag    1020
gctggctctg ggctgtgtcc ctcccatcca tgggatgtgg agccattgaa ggttgtgggg    1080
tcacgatgca ggtgctgtct cagaaagata catccgactg tgtgtgcaaa tgggctgggg    1140
cggagaagag agagagaggt agagtccatt tggagactac tgcaatagcc aggctgacga   1200
gttaagagcg gggcacagta agaatgggaa gaaatctaag aagaaaatgg tagtgcgcgg   1260
ggccaacaat ggacgatgac cgaacccagg tggggatggg tgagtgacga aagaaccgc    1320
tccgtgccgt ccagggagcc ccttgacttc ccttctgttc ttagagcgga cgtcctccta   1380
ccagccccca accagcgcca ccagggtggc gcaagcctca agctggtcag gtcagcaaca   1440
gccgcaacgg aggcaggagc cgacacgctc gtaccccggc cccctccccg ccccccgcacc  1500
cccggcagtc cctccggttt gaccactccc cccggtccct tgcctccccc gaccccccagc 1560
ctccgtcggc cgccggcacc accctccgcc cctctccgcc cctccccc tgggggcgctg   1620
actcgcccgg ctgccacgtc tcactgatga catcactagg gcagctcggc cttagccaat   1680
ccgccagggg gagtccgagc gaagtcctag ccagcgagtc agagggagg ggagcaggga    1740
ggggccgagg gtggggaggt gagggagtgg ggaatggggc gggcgacaac ccttcaggta   1800
cgcatgcccc agaggcgcgg cgcttggcgg gaagctgagt cctggccttg cgtcgcactg   1860
tctgtcctca gctcgcgtag ccgcgctcgc gactcccttt ccgggcatgc caggcggtgc   1920
ggccgccctc tgggccgtgt aaaggcccct cggtctaagg cttccctatt tcctggttcg   1980
ccggcggcca ttttgggtgg aagcgatagc tgagtggcgg cggctgctga ttgtgttcta   2040
ggggacggag tagggaaga cgtttgctct cccggaacag cctatctcat tcctttcttt    2100
cgattacccg tggcgcggag agtcaggcg cggctgcgg cagcaagggc ggcggtggcg    2160
gcggcggcag ctgcagtgac atgtccagca tgaatcccga atagtgagtt caggagagca   2220
ccggtcggct gggtccgtgg gccagcttgg gggatcttaa aggggtcgag gagggttggg   2280
gcagaagtcg gggcatcggc tggggtgagg cgagggtgat gggtcaggag aggctggcgg   2340
```

```
ccgggagtcg ggccccattg tctgacgcgg aggggcggcc gcgcggggga ggggtcgggc    2400 cggagggtg agccgcccgg gcctggaccg ggtcaggtta gagggcctga ctgcggggcg     2460
ggtgctgagg aagcctgccg aggggcctgg ggcggtgtga agggtatct tctctcggag     2520 gcagtgactt ttgaaggagg acttgtctct aaggggaggg gatgggtgg gagagccctt    2580 ctagagggca ctgtcagacc ctgcgcccgc actctgcgga gctgtcagga tcttcgggt    2640 agaaaccagc tttacttgta aatcctgagc ttgttgggtc tctctccttc catcctcccc   2700
gccaggtttc agtaaatatg gatgcttttc gggactgcgt gggattgagg ggaatgagta   2760
gatggtgaga agcaactgaa catttattag ttctcttttt gagttgtgtc ttggaggagt   2820
tgtttaagag ctcgccgggt ccattgccct cctataaaaa cctgggcatt tgtgagaatt   2880
ttgttttttt tttttttaaa aggacacct aagtcatttt gtcttctgtg ggtcaaggga   2940 aaaaaaaaa actaaagcca agaaatgtct ttttgatact cgcagattaa aggaagcttg   3000
ctgtcaagtt gaaagagaaa cgaacgggac ctatgataga tctgtatgta ggttttggat   3060
tacctgcttg gatgcttgca gatagggaat gaggttccat gacgtgtcat gaaaagttaa   3120
tgcatttctt tttcttgctt actcaagaag tcaccacagc agatgtgaca cacctggcac   3180 cttttcctggg aactggtgtt cacttccctt gggtagagtt tgttgggctc tcctcaatgg   3240 cccttttaaaa atttcctcta cagtttacat gcatgtaaag taatgaataa ttggaagaga   3300
ccgaattggt attccttttc agtgtcaaag gcctttgagg gatggggaa aatcagtatt    3360 tgttgtaaaa gttgagtta tttgctggtt tggtcaatta ctgctagaca ttttcccta    3420 aaaggtccac ccaccagttt agctgactgt catatgtgtg tcacatggct cttgcaaaat   3480
gcttacaagt tttgtaatag tgtggcttga agctgaaatc ttttgcacta aacagaaacc   3540
gtagtatttt attagaattt catgctttag aagttgaggg tagtgttctt gtagtgacat   3600
ttgctgtgtt gacagtttaa aaaattttt ttttcaaggg ctccaaggac aaagttggtt    3660
ttgcacagtt gaacggaggt gaacttgagg ttcttaattt agtagttttc ttggtaacaa   3720
taaagaacat ggatttactg ctttatcgag gtttatagac ctctactgtt caggaaattt   3780
tctgaatttg ctatatatat gtttattagt gtaaataaat cttcaagatt agttgagaac   3840
tttgacaagt tactcagcct ctgaattttt tttccctttt gtaaaatagg ataattggag   3900
tcattattcc tgtcagggta gtggtgaaat tcaaatgtat ataaaagaat ttgaaaaact   3960
gtgtgagcat tcttcaggtg gtatgcatca ttttcatgaa aggcattcta ttagtaccag   4020
gatttaggaa tataatcctt gcgcttaaga agtttagata taggccaggc gcggtggctc   4080
acctcagtaa tcccagcact ttgggaggcc gaggcgggcg gatcccgagg tcaggagatc   4140
gagaccatcc tcggtaacac ggtgaaaccc cgtctctact aaaaatgcaa aaaattagc   4200 cgggcgtggt ggtgggcacc tgtagtccca gctactcgag aggctgaggc aggagaatgg   4260
cgtgatcccg ggaggtggag cttgcagtga accaagatct ggccactgca ctccagcctg   4320
gacgacagag caagactccg tctcaaaaaa aaaattattt attgttttga gacggagttt   4380
caatcttgtt gccaggctg gagtgcaatg gcgcaaatct cctctcaccg ccacctccgc    4440
ctcctgggtt caagtgattc tcctgcctca gattcccgag aagttgggat tacaggcatg   4500
tgccaccact cccggctaat tttgtatttt tggtagagac ggggttctc catgttggtc    4560 aggctggtct caaactcccg aagtgatccg cccgcctcag cttcccaaag tgttgggatt   4620
acaggcgtga gccaccgcgc ccggcagaaa tagatttat acatgtcaaa taccagtaga   4680
tatagcaaat tccagatgtg tggcatggat gagagcaaca agatttcagg gggatggtgg   4740
```

```
gttgtggttg gctatctggg ttttggaaga ctttatagaa gagagacctg aaagggattt   4800
atcagcaatt agatttggag gaacagaggg agtgactagg aattttcaag ggggagaaga   4860
aggaggaatg gctcataaat gacaaggaca gtaataagta aatacggtgt caaatcatcc   4920
tttcttttga agactaatga cctcaaaggg atcaaaccca gaaacagttt ttatatttt   4980
tctgggatca aatacatggg tatctggcct actatatttg tattctagac tgtttagtaa   5040
aataatacag gaatttgaga aaaccttttgc aaaagtgtta gtgaaaatta cttagggtga   5100
gaggaagtga gggatatttt attaggggag gtcacaaggg cagtgagcaa tcagattttt   5160
agtaatctga cttaagcagt ttcttttttgt tttaatgaag cttgttatct ttataaaagt   5220
aattagagaa aatttggaaa ataaaggaaa gaagaaaag ttctttagtg ttttatcacg   5280
caaatacaag ctcattcgtt tttaacatct tgttccaaac tccaaagtct tgctttctct   5340
tcaattaaaa ctttaatggg tggatgcttt tcctgcttcc agtatgttat cttaataact   5400
aacaatggta tattagctaa tgtttacaaa tgtactccag atgttcctta agttactttg   5460
gtttatcatt accaatttat attgtttctt ttagaaattt ataatctttg ttaatgggtt   5520
ctgctaaatt tggtagtgaa aatgggatct tgagaaaaaa gattctgaag caacagaatt   5580
tttagattta tattggttta cataagagtt ggtagctgta ttactttttt tgtttgtttt   5640
gttttttttt tgagacggaa tcttgctctg tcgcccaggc cttggcctcc caaagtgttg   5700
ggattacagg cgtgagccac tgtgcctggc tgtttgtgtt tttttttgtt tttgttttct   5760
tttcttttc tttttttcga gatggagtct cactctgtca cccaggctgg agtgcagtgg   5820
cgcgatcttg gctcactgca atctctgcct cctgggttca agcgattttc ctgccttggt   5880
ctcctgagta gctgggatta caggcatttg ccaccataac cagctaattt ttgtatagag   5940
tacccagcca tctctaatgt tgatcaggct gaagcaggtg gatcacctaa ggtcaggagt   6000
tcaagaccag cctggccaat atggcaaaac cctatctcta ctaatacaga aaattatctg   6060
ggtgtgttgg ctggcgcctg taatcccagc tactcgggag gctgaggcag gacaatctct   6120
tgaacctcgg aggtggaggt tgcagtgagc cgagatcaca ccattgcact ccagcctggg   6180
caacagagca agacttgtct caaaaaaaaa aaaaaaaaaa aaaaaaggc aattgaaagt   6240
gtaatctgaa cagttaaaaa agtagataga aagggttaaa gcttttttttt gaggatctga   6300
agaaaaatgt ggatttttttt tgagctacgt tttgaagcag gcagtgatta tttcagcaca   6360
ttaagaaatg cttaacatgg ccaggcgcag tggctcacgc ctgtaattct cagcactttg   6420
ggaggccgag gtgggcggat catttgaggt catgaccagc ctggccaaca tgatgagaca   6480
ctgcctctac taaaaataca aaaattagct gggtgtggtg gtgcacgcct gtaattccag   6540
ctactcagga acctgaggca ggagagtcac ttgaacctgg gaggcggagg ctgcagtgag   6600
tccagatcat gccactgcac tccagcctga gggacagagt gagactcctc aaaaaaaaaa   6660
aaaaaaaag aaagaaatac ttaacattat tctcgtgatt attctcataa catttttcat   6720
aatccactgg cttccagtgg attttttttag tgtcaagaaa ataattttga ttggttcatc   6780
tttaaggaat gtgttaagaa taaagcatgt ctacctgtct tcagtatacc agctaactat   6840
agtaggaaga aatatagtag tctacttaga tcaactataa ttctttaatg cagaaaaagt   6900
ttaaagtatt taccttattt ttagccccca tccccttaag tatatcatgg ctccagaatc   6960
tctgaaaatg ttatcagtct ttcagacttt gctcttcttt catgttatac tcaagaaaca   7020
tttgaccttt ttttttttttt ttttgcttgc attgtgtttc aaataatttt taacaaaact   7080
taagtgtttg aaagtgaaag caggttgtct ttgtgacttt tggtggtggt ttgaaaaact   7140
```

```
cagaaaagtt taaagaagaa agataactag tattctcatt gtccagaata tgatttttta    7200
aatgtctata gaatatcacc atctgtaatt cttccggtaa tttaagtatt cagtagttgt    7260
ataaaacctt taaatatat atattgagaa ttttgtgtga atgagatgat gagataatct    7320
tgtaggatca tttaaagata agaactgagg cctggcacag tggctcatgc ctataatcac    7380
agcactttgg gaggcccagg cggtagatca cctgaggtca ggagtttgag accagcctgg    7440
ccaacatggc aaaaccctgt ctctactaag catagaaaaa ttaattgggt gtggtcgtgc    7500
ctgcgtgtag tcccagctgc ttgggaagct gaggcgggag aatctcttga accctggagg    7560
tgggcattgc agtgagctga gattgcgcca ctgcactcca gcctgggcga cagagcaaga    7620
ctctgtctca aaataaagta aaataaaatg aagataacaa ctgaaatttc acattaaaaa    7680
tttttttgta gcgactgtgc ctcctatgtt gtgcaggctg tctcaaact cctgcctca    7740
agcgatcctt ccaaagcact gggtgggcca ccatgtccag cctgaaattt tgcattaaaa    7800
aatttcccgc ttttggctgg gcgaggtgtc tcacgcctgt aatagcagtt tgggaggccg    7860
aggcaggcag atcacttgag gtcagttcta gaccggcctg gccaatgtgg tgaaaccctg    7920
cctctactaa aaacaccaaa ttagctaggc gtggtggtgt gcgcttgtag tcccaagcta    7980
ctgaggaggc tgagacaaga gaatcgcttg aatctgggaa aaagaggttg ccgtgagcca    8040
agattggcca ctgcactcca gcctgggtga cagagtgaga ttctgtctca aaaaaataaa    8100
aaataaaaat ttccccttt aatcaaatta agttaaaatg agggatgtta gacagttttt    8160
aaccatcaaa tatttagtt tagtttttt tttttaacgt tgtcttaaag atggaagtgc    8220
ttcaaaatca aatcttcctt gccagttctc tacttggctt cttttttttt cttttttgaga    8280
tagagtctca ctttgtcact ggagtgcgtt ggcgtgatct cggctcactg caacctccgc    8340
cttccaggtt taagtgattc ttccacctca gcctctcaag tagctgggag tacaggtgtg    8400
tgccaccaca cccggctaat ttttgtagtt ttagtagaga cagggtttca ctatgttggc    8460
caggctggcc tcaaactcct gacctcgtga tccacccacc tcagccaaat tgctgggatt    8520
acttgtgtga gccacgcgcc tggcttctac ttggctttta agggaatttt tgctttctga    8580
gtaattttat ttctcaggta tcttggtctt tttaattctg gaagcaatct taataattta    8640
tgtatgtgcc ctgtaatccc agcactttgg gaggccgagg tgggcgaatc acgaggtcag    8700
gagatcgaga ccatcctggc taacacggtg aaaccccatc tactaaaaat acaaaaaatt    8760
agctgggcgt ggtggcaggc gcctgtagtc ccagctactt nnnnnnnnnn nnnnnnnnnn    8820
nnnnnnnnnn nnnnnnnnnn nnnnnnnnnn nnnnnnnnnn nnnnnnnnnn nnnnnnnnnn    8880
nnnnnnnnnn nnnnnnnnnn nnnnnnnnnn nnnnnnnnnn nnnnnnnnnn nnnnnnnnnn    8940
nnnnnnnnnn nnnnnnnnnn nnnnnnnnnn nnnnnnnnnn nnnnnnnnnn nnnnnnnnnn    9000
nnnnnnnnnn nnnnnnnnnn nnnnnnnnnn nnnnnnnnnn nnnnnnnnnn nnnnnnnnnn    9060
nnnnnnnnnn nnnnnnnnnn nnnnnnnnnn nnnnnnnnnn nnnnnnnnnn nnnnnnnnnn    9120
nnnnnnnnnn nnnnnnnnnn nnnnnnnnnn nnnnnnnnnn nnnnnnnnnn nnnnnnnnnn    9180
nnnnnnnnnn nnnnnnnnnn nnnnnnnnnn nnnnnnnnnn nnnnnnnnnn nnnnnnnnnn    9240
nnnnnnnnnn nnnnnnnnnn nnnnnnnnnn nnnnnnnnnn nnnnnnnnnn nnnnnnnnnn    9300
nnnnnnnnnn nnnnnnnnnn nnnnnnnnnn nnnnnnnnnn nnnnnnnnnn nnnnnnnnnn    9360
nnnnnnnnnn nnnnnnnnnn nnnnnnnnnn nnnnnnnnnn nnnnnnnnnn nnnnnnnnnn    9420
nnnnnnnnnn nnnnnnnnnn nnnnnnnnnn nnnnnnnnnn nnnnnnnnnn nnnnnnnnnn    9480
nnnnnnnnnn nnnnnnnnnn nnnnnnnnnn nnnnnnnnnn nnnnnnnnnn nnnnnnnnnn    9540
```

```
nnnnnnnnnn nnnnnnnnnn nnnnnnnnnn nnnnnnnnnn nnnnnnnnnn nnnnnnnnnn    9600
nnnnnnnnnn nnnnnnnnnn nnnnnnnnnn nnnnnnnnnn nnnnnnnnnn nnnnnnnnnn    9660
nnnnnnnnnn nnnnnnnnnn nnnnnnnnnn nnnnnnnnnn nnnnnnnnnn nnnnnnnnnn    9720
nnnnnnnnnn nnnnnnnnnn nnnnnnnnnn nnnnnnnnnn nnnnnnnnnn nnnnnnnnnn    9780
nnnnnnnnnn nnnnnnnnnn nnnnnnnnnn nnnnnnnnnn nnnnnnnnnn nnnnnnnnnn    9840
nnnnnnnnnn nnnnnnnnnn nnccaggctg gagtgcagtg gcacaatctt ggcttactgc    9900
aacctctgtc tcccgggttc cagcatttct tctgcctcag cctcctgagt aactgggact    9960
acaggcgtcc accaccacgg ccagctaatt tttatattag tagagatggg gtttcaccat   10020
gttggccagg ctggtctcca actcctgacc tcaggtgatc cgcctgcctt ggtctcccaa   10080
agtgctagga ttacaggcgt gagccactac gtttggctgc ttatcagctt tttaccactt   10140
tgtcgccact acattttgga attttccttt gagaattagg caaaatgccc agactccccc   10200
ccggcccccg ctttagaggg agagggagc aattagacta ttcctttgtt tccctataga   10260
aggtggggct gagattactg ctttgatatc tggaatgtaa tttagggaag aaaatttagg   10320
tcttggcctt tctttggaac caccctggga gtgttgcaga ttattaatag ggtaatggtg   10380
gaatgatatt caggggaaaa atggtcctga ggagccagag aactaagtgt tagtttgttg   10440
gctgactgaa acatgtgaga gatagggtac agaagaagta ggaaatagtt ttccttggta   10500
cttctgtgac aggttggctc aattggctgg aacaccctac actgctttat taaatccaag   10560
gttgtgatag gttccagtta agtttactgt gttctatgct tgtagatttc ctaattagga   10620
caagtagtgt taaatatgca tgcctttatt cacaagaggg accattcttt tggaaacatc   10680 acttttttaat aatactaggt gctatttagc acttactcgg tgccagccac gtggctatgg   10740
tttttttttt ttttttttttt cgagacatga tctagctctg tctcccaggc tggagtggtg   10800
gtagcacagt catggctcac tgcagtctca acctcctgta ctctagtgat cctcctgtct   10860
cagcctcctg agtaactggc accatgcctg gctaattttt tttaagagat gagatgtcgc   10920
tatgttgcct atgctggtct cgaacacctg ggctcaagtg atcctccccg cctgagcctc   10980
tcaaagtgtt gggattacag gtgtgaccca cctcacttgg ccatctatgg tctttacata   11040
gggcattttg tgcagtctgc atctcaaact agtgatcttc aacagtgaaa ctcagtgaat   11100
tatgtaattc atgttttcca agaacaatga tggatttaat ttctctgaat gtatttcctt   11160
tgtataataa tagtacttaa gtggaattac tctttgtcct ttctactctc cttatagata   11220
ttttctggta tcttgatttg ggactgttac atttaaccca tttatggtcg tgtagccata   11280
ctcacgttac atttgatgca tctgctccct ttgtgtctat atactcatat aacattttgc   11340
ataaagttat aggcagttca caccaaggct gttcatgaac ctcagattaa gaatacttga   11400
tttaggagat tgaaaacaga aaagagaatg ttaactatca ttatcaatat taaaatgtga   11460
aaatctgaga gtgacaaagc ttagctttaa atctggtatc ccaaactcat ttgagttttt   11520
tttttttttt tttttttttt gagacaaggt gtcgctttgt cccccaggct ggagtgtagt   11580
ggtgtgatct tggctcactg caacctccac ctcccaggtt caagtgattc tcctgcctca   11640
gcctctgaag ttgctgggat tacaggctgc gccaccacgc ccagctaatt ttttgtattt   11700
atagtaaaga cggagtttca ccttattggc caggctggtc tcaaactcct gatcttgtga   11760
tcctcccgcc tcggcctccc aaagtgctgg gattacaggt gtgagccact gttcccggcc   11820
taatttgagt tttaaaatgt ggagtttaag atgttagtct taaagtgggt tagatgaaat   11880
ttataaaaat agtcaaatag ctaaatttat aaaaggccat ttgaaacaat tttgtgaaat   11940
```

```
atataatgtg gataattatg tagtgcttta tgtgtagatt ggtggttagc atctgcctga    12000
tgaagagcag ttggatttct tacttactaa agctagtgaa atctgaactc caaattaggc    12060
atcttcacca ggcttttttg agccgagcta acttactctc ttttttattt ttattttta    12120 attaattaat tttttttttt tttttttttt tttggtagag acaggatctc cccatgttac    12180
ccaggcttgt ctctggctcc ttggctcaag cagtcctcct accttagcct cccaaagtgc    12240
taggattaca gctgtgagcc actgcgccag gctgagctta ttctctacta acacaagtgt    12300
tctaatttaa tttaagcagt gaatcacact tttctttgta tttggtcagg ttctgggtgc    12360
tagtttatat atgatttgat tcattctgat agggtttttt tgttttttt tgttttttgtt     12420 tttttgtttt ttttgagaca gagtctagct ctgtcgccca ggctggagtg tggtggctcg    12480
atttcgggtc attgcaactt ctgcctccca cccaggctgg agtgcagtgg ctcgatttcg    12540
ggtcattgca acctctgcct cccaggttca agcgattctc ctgcctcagc ctcctgagta    12600
gctgggatta caagcaccca ccaccatgcc cggctaattt tgtgtatttt tagtagagac    12660
tgggtttcac catgttgacc acgctggtct cgaactcctg acctcaggtg atctgcctgc    12720
cttggcctcc caaagtgctg ggattacagg tgtgagccat cacaccaggc tcaagaact    12780 ttttatttt gagacagggt ctcactctgt cacccaggct ggagtacagt ggtgagatca     12840
tggcttactg cagcctggac ttcccaggct ctggtgatcc tcccatctca gcccctggag    12900
taattaggaa tatagacaca cacccatgcc tggcagtttt tgtatttttt ttctttttc    12960 tcttttttg tagagactgg gtttcacatg ttgtatcagg ctggttttga actcctgagc     13020
tcaagcaatc ctcactcttt gacctcccaa cgtgctggga ttacaggcat gagccactgt    13080
acctggcctt ttctacatta aaactttttt attaaaaaac ccaaatcttc cttgtggttg    13140
tatatacata tatacatagg tacacacatg gagaatttta ccttggagga aggcttggta    13200
aagaaaatag ccctttgggc cgggtgcggg ggctgacgcc tgtagtccta gcactttggg    13260
aggctgaggt gggcggattg cctgagctca ggagttcaag accagcctgg gcaacacagt    13320
gaaaccctgt ctctactaaa atacaaaaaa tcagctgggt gtggcagcat gtgcctgtag    13380
tcccagctac ttgggagcct gaggcaggag aactgcttga acccgggagg cagaggttgc    13440
agtgagccga gattgtgcta ctgcacttca gcctgcgcga cagagcaaaa ctctgtctca    13500 aaaaacaaa caaacaaaca aaaaggaaa atagcctttc tctatcatca gagtatatta     13560
agagttgagt tttttttct gttttttaaa attttgttg tttattttaa attacaaaac      13620
atggactctg cttacaaatt aagaaaatga ctcatgttca aacaagcata atcaatataa    13680
cagttaatac aagttaaata ttgtaatatg tttacggaat agcatggcaa aatagtgcaa    13740
aagatttggg gaaggggcct ataatttctg ttaacagaaa gttttagtta tgttgattca    13800
actggagagg aacagagctc ccagaaggac tccagaacac ttgatgcttg tctgagtggg    13860
gtcagcagca ctgagttccc accagccaga aagtttgtgt gtgtacatta tttcccttaa    13920
ctgccacaat aatcccatga agaaaatgcc ctagttttac aaacaaggaa acagaggcag    13980
agaagagtta aatgacttgc ccaagggcat tcaaagtaag caactgaatt ggaattttaa    14040
ctcaaaggct tggatgtccc actacaacaa ataggctgtt tctgctttac tacatgtgct    14100
tacttctaag aatttaacat tttaggctgg ttgtggtggc tcactcctgt aatctcagca    14160
ctttcggagg ctgaggtggg taaatcactt gagctcagga gtttgagacc aacctgggca    14220
acatggtaaa acctcatctc taccaaaaaa aaaaaaaaa ctagctggac gtggtggcac    14280
gcgcctgtgg tcccagctac tcaggaggct gaagtaggag gatcgtttga gcctgggagg    14340
```

```
tggaggttgc agtgagccca cattgcatca ctgcactcta gcctaggtga cagagtgaga    14400
gcctatctca cacacaaaaa aaagaattta aatttttagt caagtaatta ggcactaaca    14460
ttttgtggtc agttacttta cgaattcatg gttggaggcc tgatgtggtg gctcatgcct    14520
gtaatcccag cactttggga ggctgaggca ggaggattgc ttaaggccaa gagttcaaat    14580
cagcctgagc aacctagtaa gatccccttt ctgcaaaaaa tttaaaaatt agctgggcat    14640
ggtagtgtgc acctgtagtc ccaaccactt gggaggctga ggtgggagga ttgcctgagg    14700
ccaggagttt gagacctggg cagcatatga agaccctgtc tctaaaaaac taaaaataaa    14760
aaatagccag gtgtggttgg tgtgcttgtg gtcccagcta ctcaagaggc tgaggcaaga    14820
gggttgcttg agcccagaag ttggaggctg ccgtgaactg tgattgcacc actgcacttc    14880
agcctgggtg acatagcaag accctgtctc tgtggtggtg gtgggtgggg gtgggggaag    14940
ggatttaaga aggggtttgtg aggtatgtat tatttataaa tgggctttta actttaccct    15000
tcacatcttg ggttgaaatt aattgtatcc attctcagtt tttctgtctt gctatatatt    15060
taaacttgga gacttagagg tcatggatgt cttttctatga aaagcaaatg aagcagaggg    15120
ctgccttctc ttgctgtaga gggcacactt gctgcagagc atgttactgt tttatgcatt    15180
gctaggcttt gggagttgtg acttgtatga tcatagtact tacaactatt agttggcaat    15240
ttttaaactt taactttaga ttatatatgt aaactcctgt gttcctttgt cactgataat    15300
ctgaacagaa gccttggata ataattttg aagttttgt ctgaacctct gaaatttgta    15360
ttgttatctc atggttttgc tgggaggaag gagaaataac aatggccact tactgtgctt    15420
ctgtatgtgc cagacagtat gtgctagatg tttcagaaac gtgatttgta atcctgacaa    15480
gaagcctaat tgggtggtag tgggtgctaa ttgaacctta tagatgagga aattgaggct    15540
catggtggta agtgaataac ttgcaccaag atcctatggc tggtatgcag tagagcctca    15600
attcaagtac gggtcttcca ggtccaaacc catgcaggct ttgagaggta aggaggtaga    15660
gaacgttgac accccttct tggtgtgttt ttcagcaaat acttgtatgc atattaaaga    15720
ctgtctaccc ttttgtcatc ttgtgtcact tgctgcttcc tttggtacta cccaaatttc    15780
tttcagcatt tcagctttga atttttattt ttatttttатт taatttattt atttttttga    15840
gatggagtct cactctgttg tccaggctgg agtgcagtgg cgtgatatca gctcactgca    15900
acctctgcct cacaggttca gcaattctt cctgcctcag cctccttagt agctgggact    15960
ggaggtgccc accaccacgc ccaactaatt tttgtatttt tagtagagat agggtttttac    16020 cttgttggcc aggctggttt tgaactcttg gcctcaagtg atccaccac ctcggcctcc    16080 caaaatgctg ggattacagg catgagccac tgcacctggc cagctttgaa tttttagaat    16140
actgttctaa acagaactat attggaacct ggaaaattaa tctattgtct ctaaatacca    16200
aagaaaaaca tgtaatttta gtggttgatt atgggaacaa ttttttttaa gatggttcat    16260
ctgaatggga agcattttt ttttaattgc ttgactattt ctttaaattt ggagaaaaga    16320
ccattgccct ctcagatttc tggtaattgg tcacattgat catttatatt gactgacagg    16380
ctgctttgtc cacagctgaa ggattgttta atttttttta aattataaga gtaatatgtg    16440
ctcactgtaa aattcacagt acagaagcat atgaactaac taaaagttct tacctcttgt    16500
ctccagcaag gagtaagtgt ttcaacctga aggttggttt tgaattgtgt tctgtgggagc    16560 gtacttaaag tgagtgaaga agaaaaattt atgtcaatca tgatcattgc agctgaagtt    16620
tttattgttt cacccctaa aggttattaa aatagtatgt agtttagtag tcttgataat    16680
tttcccttaa gatttattgg ccagtatatc aggattttgt tttaaatttg atatgtgagc    16740
```

```
ttagttttat gctattttca aataagacat ttagaagaag ataaaataac attcctgtct   16800
tagtctgttt tctgctgcta taacagaata gcacagactg ggtaatttat aaacagtaga   16860
agtttatttg gcctgtggtt ctggaggctg ggaacttcaa gagcatggtt ctgccctttg   16920
tgctgtgtta tcatatggtg gaaggtggaa aggcaagtgg gtatgtcaag acagagagca   16980
agaaggggct tgaactcact tttataacag agtgactcca gagatagcta acccactttt   17040
gagagaatgc attaatccat tcatgagggc agagcccttg tgacctaatc acctctcatt   17100
aggctctgca tccttaaact ggttttttt tgttttttt ttttgagacg gagtctcgct   17160
ctgttgccca ggccggactg cggactgcag tggcgcaatc tcggctcact gcaagctccg   17220
cctcccgggt tcacgccatt ctcctgcctc agcctcccga gtagctggga ctacaggcgc   17280
ccgccaccgt gcccggctaa tttttgtat tttttagta gagacggggt ttcaccttgt   17340
tagccaggat ggtctcgatc tcctgacctc atgatccacc cgcctcggcc tcccaaagtg   17400
ctgggattac aggcgtgagc caccgcgccc ggccccctt aaactgttgt attggggatt   17460
aagtatctaa cacaggaact ttggaggata catttaaacc ataagaattc ctgtcatgca   17520
aatgaatcca ttctagatga aagagaatga atttagtttc cattgaactt tataaatagg   17580
ccttttctaa ggtacttaca gctgatatta taaatttat atttgttttt ataaatttgt   17640
atttgtattt ctgtttgtac aaatacaatt atacactata gttctctgct gttagatttt   17700
ttttcttcct tagcatgttt ccaaagggtg gaatgttgaa agttgggtta atgtcaatca   17760
gcttttcttt gtaaagtgtt cattgacatg tgaaccttgt ctgagaatct aaattttatt   17820
tcatgaaaga agaaaacagt atattctcat ttaacccaga atttaacttc atatacttgt   17880
ggctgtattg ggagtatgcc attgctgtct gtttacaacc tgacctactc tacctactta   17940
gaagtaattt gtgttatgat aggtgtgctg tgctgacata tgctgaacat atttgtaagg   18000
gtgttaagtc attgaataaa acgcttttct cctcctttca aataacattt tttatttctg   18060
gttataaaag tcatacaagc ttactgcagg ttgttaaaaa ggtataaaga agaaaccgtc   18120
aatccattat aatcctacag tttagacttc ctgctccagc ctctcagagt gctgagatga   18180
gctagccatg cccagccct caaaagattt tttaaaaaac aaaaatgagg ttatacttta   18240
aaaaattcta tattcctttc acataacagt gttattttgg aggttttaga atttccagta   18300 gcatttaga ttcagaaaca agctgattca tcctctactt tgtactttag gcaagaaaag   18360
aattttacct aaatagaatt ttgaactgaa aatctgtttt tctaactttt tatttaaaga   18420
atattgttcc atgctttcac agtagtgact tttaatttt atatttttta ttttatttat   18480
ttagagatgg gggtctcact cttgttgcct aggctagagt gagtgcaatg gttctattcc   18540
tagctcactg caaccttgaa ctcctgggct caagttaccc tcctgcctca gccttctaag   18600
tagctgggac tacaggtgtg caccactgca ccaggctttt tttaaaggca tagaaaatgg   18660
tagtgcttgc atacaaaaat ggcgtaggta catacatcag cggacatcaa gactatgttc   18720
agatcataaa tgtacatata tgtaccgatg ccatttttgc acgcaaacaa ataatggaaa   18780
ttgaactcta aactgaaatt tgaaacaagg gttctggggt gggccctctt gctgatttgt   18840
aattgaatgt atagttcaat ttttccccat ctgttaagca aaagacaatt ctaatgttag   18900
caaaaatcca catatcctgt cattgatcat ttttccctta atttcttta agagatgggg   18960 cttctctcta tgttgcccag gctggtctgg aactcttggg ctcaaatgat cctccagcct   19020
cagcctccca agtgctgga attaataggc acaagctgct gtgcctggcc ctgtcatcag   19080
tcatttaact tcatgcaaac tgagtagaat aaaactcgtc cttactgtac cttattgctt   19140
```

```
ttgttttatt gttggaacct ccaatattgc gaaagtagac caaaagttga cttataggaa    19200
aaactgatag caaaaataat ttttctcttg ttgctgtatt tcatgccac catccagttg     19260 ttaaagccta ctgttaattt ctctcagcct cctcctttct gtccaggctt attctatgcc    19320
attcttacct taactgtttt tagctttctc atagagtgaa cttttttaaat taaaataaaa   19380 tatctgctcg tagtattata aaattcaagc agttcaacag aattttttcac taatagaaat   19440 acttgtacct caaaagcagc tttatttac aaacccagcc caatttgtga ttagatttaa     19500
cttgagaaaa catgaaatgt ctctcatatt gtttaaaaat atcataagtg gctgggcacg    19560
gtggcttatg cctataatcc caacactttg ggaggctgag gcaggtggat cacttgaggt    19620
caggagtttg agaccagcca ggnnnnnnnn nnnnnnnnnn nnnnnnnnnn nnnnnnnnnn    19680
nnnnnnnnnn nnnnnnnnnn nnnnnnnnnn nnnnnnnnnn nnnnnnnnnn nnnnnnnnnn    19740
nnnnnnnnnn nnnnnnnnnn nnnnnnnnnn nnnnnnnnnn nnnnnnnnnn nnnnnnnnnn    19800
nnnnnnnnnn nnnnnnnnnn nnnnnnnnnn nnnnnnnnnn nnnnnnnnnn nnnnnnnnnn    19860
nnnnnnnnnn nnnnnnnnnn nnnnnnnnnn nnnnnnnnnn nnnnnnnnnn nnnnnnnnnn    19920
nnnnnnnnnn nnnnnnnnnn nnnnnnnnnn nnnnnnnnnn nnnnnnnnnn nnnnnnttc    19980 accatgttgg ccaggctggt ctcaaactcc tgacctcagg tgatccacct gcctgggcct    20040
cccaaagtgc tgggattata ggcttgagcc tcgcctggcc tcctcataat ttttttaacct   20100 ttataaaaac cttttctaaa acccttttta ttttgaacta aatttagatt tactgaaatt    20160
gtgaaatcaa tgtggagttc ttgtatatccc ttctttccgc ttttcctaat agtaacatct   20220
tacatacatg gtacatttgt ccaaattaag aaataaacat tggtacagtg ttaactatag    20280
acttaatctg gtttctctaa ttttttcact aatgttcttt ttctgttcta ggatctaatt    20340
cagtatacca tattgtattt agttgtaggc catgttagcc accttcaatc tgtgacagtt    20400
tctcagtctt tccttctttt tcgttatctt gacaagtttg aagagtgctg ataggtattt    20460
tatagaatgt ccgtcagttg tctgtcagtt tgtatttgtc tgatgtattt tttttttttt    20520
ttttgagatg gtgtctcgct ctgtcgccta ggctggagtg caatggcatg atcttggctc    20580
aatgcagcct ccacctccgg ggttcaagtg actgtcctgc ctcagtctcc caagtaactg    20640
aaactacagg catgtgccac cacgcctggc taattttttg tattttagta gagaagcagt    20700
ttcaccgtgt tgcccaggct ggtctcgtgc tcctgagctc aggcaatcca cccgcattgg    20760
cctcccaaag cgctaggatt acaggtgtga gccaccatgc ctggccaata ttttgaggga    20820
tatactttgg tgaggtcatg cagatatcct gtttctcctt agttttatcg attaatttag    20880
catttatcca gtaaatcttc cttgcagcaa ttattttttc ttttttcttt ttccttaatt    20940
ttttttttaa gagatgggat ctcactctgt tgcccaagtt ggaatgcagt agtgagttca    21000
tagctcactg cagcctcaaa ctcctgggct caagtgatcc ttctgcctca gcctctcaag    21060
tagctgggac tacaggcata gaccaccaca cccagctaat taaaaaaaat attttagag    21120 atgggggttt tgctatgttg ctcaggctgg tcttgaactt gctggcctca tgtgatcctt    21180
ctacctcagc cttacaagta ggtgggaatt acaggtgtga gccaccacac ccagcattgc    21240
agcaattatt aatgtagtgc tactggtcat tttctgtttt tctcatttct tcagcatgtg    21300
ttattgactt gtctcttccc tcccatttat aatcatttat actgctatga attcatgagt    21360
atttattttg tgagttataa tctaatacgt acttaattta ttttgtgcct caaattgttc    21420
tggcttggcc atttttttt tttttttttg agacggtctc gctctgctgc ccaggctgga    21480
gtgcagtagc gccatctctt ctcactgcaa cctccacctc ccgggttcaa gcgattctcc    21540
```

```
tgcctcagcc tcctgagtag ctgggactac aggcgtgtgc cgccacaccc gtctaatttt    21600
ttgtatttt  agtagagaca gggtttcacc atgttagcca ggatggtctc gatctcctga    21660
cctcgtgatc tgcccgcctc agcctccaaa agtgctggga ttacaggtgt gagccaccaa    21720
gcccgaccgg ctcctgtatc cttttaacat gaggtgctgt catcattttt tcccctaat    21780
attttggcca aaatgttaa  tcaaggatgg cacaaatttt ctgtagctgt atctcacaat    21840
gaaagaggcc tgattaaaaa tgtaaaacta aatgttctc  tgatctctta gcacatgctt    21900
tgtaaaaggc acagtgctag atccttgtat acgtagatga gtaagtcagc ttaccttcca    21960
cacccacaga tagctatgtc aaacgtaagg gtggagaaac acagacccca aacttctcga    22020
gggtagaaaa tatgaggtta tagtagatta gaactacaaa agctagagg  aagttctgaa    22080
ctggaaacag tggataggat ttactagaat aatttacgag ggtgacaatt gtaaatcttc    22140
ataggtttct ttttttttcct ttctctttt  tttttttga  gatggagtct cgctctgttg    22200
cccaggctgg agtgcaatgg cgcagtctct cctcactgca acctccgcct cctgggtcca    22260
ggtgattctc ctgccttagc cacccaagta gctgggatta caggcatctg ccaccatgct    22320
gagctaattt ttgtatttt  tttttagta  gagacgggt  ttcaccatgt tggtcaggct    22380
ggtcttgaac tcctgacctc aggtaatcca cccaccttgg cctcccaaag tgctgggatt    22440
acaggtgtga gccaccgcgc ccagccaaat ttttattggt ttctaaacta gcgtaattta    22500
gtttttttca cttaagtcaa aattatatta ttgtaggata aaaacttagt gatccaaatt    22560
catgaggaat gaagaataaa tacatttaaa gtcttaccat ttgctaaatt agtcttggct    22620
ctttgtacca aaattctgtc cttgtgctct gtaattttat atttgtatat tttctatcaa    22680
catttttact gtgtggtgtt ttgtaaatta taaaaacgtt ttaaagcaaa ctcagaacaa    22740
tgaattctca cgaatattca gtatatttac agttgagaaa taaactactt ctgtagtagg    22800
taatttaaaa tgtcccaatg caagttaacg tgtcactgat cacgctattc aggtgtgtgt    22860
ctttgataag gggaggtggg gaagtttgtg ggtttgattt tatttgcctt tctcatgtga    22920
ctgttgtcat gttagtaaac aaatggtttg cgagagaacc agtagtcttt tgcaaagatt    22980
gtcttataca gagcactcaa ttcttcatat tatttataat ggctttaatt taagccttaa    23040
attattagaa actcataaat aatttttta  tttgtttttt tgagatggag tttcgcccct    23100
attgtccagg ctgaagtaca atgatgtgat cttgactcac tgcaacctcc gcctctcggg    23160
ttcaagtgat tctcctgcct tgcctccca  agtagctggg attacaggca tgcgctacca    23220
tgcctggcta attttgtatt tttagtaaag acaggattgc accatgttgg ccaggctggt    23280
ctcgaactcc caacctcagg tgatccacct gcttcggcct cccagagtgc tgggattaca    23340
ggctcactga gccactgtgc ccagccataa tgcgttaaaa taagagtgtt atatttgtaa    23400
aacttaaaaa aatgtagtgg ttgaaaaagg taatttaaaa agaattgact attaatttct    23460
tgaaaccata atgtaacttg tagtgcaatt aggaaacctt catgtttctt tctttctttc    23520
ttttttttt  ttttgagat  ggagttttgc tcttgttgcc taggctggag tgtgtgatgt    23580
cagcgcactg caacctctgc ctcctgggtt caagcaattc tcctgcctca gcctcccgag    23640
tagctgggat tacaggcgcc tgccaccaca cccagctaat tttgtgtattt ttagtagagg    23700
cggggtttca tcgtgttggc ctggctggtc tcgaactcct gacctcaggt gatccactgc    23760
acctggcccc cgttcatgtc ttttaaagct ttatggttgc tctgaaatag agttgttgat    23820
ttttttttt  ttttgagac  tcctcttttg cccgtgctgg agtgcagtgg tgtgatctga    23880
gctcactgca acctccacct cctgagttca agcaattctc atgggtcagc ctctcaagta    23940
```

-continued

```
gctgagatta aagctgccca ccaccatgcc tagctaattt tagtattttt agtagagatg   24000
gggtttcacc gtattggcca gggtggtctg gaacttctga cctcaggcat gagccactac   24060
gcctagcctg ggttgttgat ctttaaggtg atacttcagg caacatctga ggcccagtac   24120
agtcctttac ttcaactggc tccagtacag caaattcagg gaatgttttt gagtgtttac   24180
tggatgcctg gcgtggagtt cagggagatt ggtacattga gtccagttgt tgtgttgaaa   24240
cttctgttta aaacctccc tactaagtcc cagctactca ggaggctgag gcctgagaat   24300
cacttgaaca cctggaggca gaggttgcag tgaatcgaga tcgagccact gcactccagc   24360
ctgggcgaca gagtgagact gtctaacaac aaaaacaaca ccccccaaaa aaccaaccta   24420
ctatggtagt atcaatgctg tgatagtctt cctttcttca tacaggtaaa ttcttaacat   24480
atactcattg ttaatgttca gtgttcagta ttcttaagag tatttggggc caggcacggt   24540
ggctcatgcc tgtactccca gcactttggg aggctgaggt gagcagatta cctgaggtta   24600
ggagcttgag aacagcctcc aacatgatga aactcccgtc tttactagaa atacaaaaat   24660
tagctgggtg tgttagcaca tgtctgtaat cccagctact tcagaggctg aggcaggaga   24720
attgcttgaa cctgggaggt ggaggctgca gtgacctgag attgcttcac tgcactccag   24780
cctgggcaac agagcgagac tcttgtctca aaacaaacaa acaaaaaaag aatatttggg   24840
gccaggcatg gtggctcaca cctgtagtcc cagcactttg ggaggccaag gtgggtggat   24900
cacttgagat caggagttgg agaccagccc gaccaacatg gctaaatccc gtctctacta   24960
aaagtacaaa aattagcttg agcaacagag caagactctg tctcaaaaaa agaaagaaga   25020
atatttggtt taattaagaa ggaaccttat caatagtagt aaagtcagcc agctgaactg   25080
ccaagtacaa attgttggta ttaggtatca atcatttatt aaggataata ttctacaata   25140
gcgatctttt taaaaatttt aaaatctcaa actggaaagg atgtctagtt cattctatgc   25200
ttcagtcccc tcttctgatt tacttgttta gaagattttt gtttccttct ctgacttcta   25260
ttttgctgct gactggcact tgggattttt aaaaaattat tttcctcata tataattaaa   25320
gacaataagt ataacaataa gtataatatg gtaatttgct aaaacccaaa caatgtttta   25380
agtaatgcat atcattatgt aaacctacgt aatagttgaa tattcacaaa gataatcgct   25440
tatagaagtt ttatatcctc tcttctttgg cagtgcaatt aaaacaaaaa aaataagttt   25500
tatgtcttgt ttacatgtaa ataattttaa tctaaattgt gacgtggttt tcactttagc   25560 atattttga agtaaatca aaaggacaa aatacaaaat catgtatatc ttctacaaaa   25620
acgatatata aattctaagg tttttgtcct tttgaaattg cttaaaagaa tgcatagaac   25680
tggtgtctga gttgggaagg atctatgagg gatttccttg gagaccgtgg gtgaataata   25740
atgttgtctt agttccatga aggaatctct ggggatagtt tttgagttag gcctggcaat   25800
gttagagata cataaagaga gccttgtttt atcactgggt gcggtggctc acacctgtaa   25860
ttccagcact tgggaggct gaggcgggca gatcatgagg tcaggagatc gagaccatcc   25920
tggccaacac ggtgaaaccc gtgtctacta aaaatacaaa aattagctgg gcgtggtggc   25980
gcatgcctat aatcccagct actcggggag ctgaggcagg agaatcactt gaaccaggga   26040
gttggaggtt gcagtgagcc gagatcgcgc cactgcactc cagcctgggt gacagagcaa   26100
gactccgtct caaaaaaaaa aagcttggtt ttcaatggtt ctgaaaaatg ctttaataca   26160
agtgtagagt gttagtcaag ttttgcactt ggataaacag cctgtgaatt tatcacattt   26220
ctagtttata atatgggctt tcagaagtta tatgaacatt gttttgacgg gagaattcaa   26280
gctggatgct agagaaggat cgtgagaacc ccttcattgg aggagtgcta tgaaattatt   26340
```

```
tgatcttgga attttttttt tttttttttt tttttttttt ttttttgagac agagtttcgt   26400
tcttattgcc caggctggag ctggaatgca gtggcacgat ctcggctcac tgcaacctct   26460
gcctcctggg ttcaagcaat tcttctgcct cagcctacca ggtagctggg attacaggca   26520
tgcgcaacca tgcccagcta attttttgtat ttttaatgga gacggggttt caccatgttg   26580
gtcaggctgg tcttgaactc ctgacctcaa gtgaactgcc tgcctcagcc tcccaaagtg   26640
ttgggattac aggtgtgagc cactgcgcct ggcctgatct tagaatttga aggagagact   26700
aatatttcat gggcaaaaac aatgaaaagt tacctttctg tattctaata ctatagagga   26760
gtgggatttta tttagaatgt tttaagtatc ttgggcagtc caagagtgcg tatcacttat   26820
ttttcttttc cttctttctt tttaagtgga agttcactga tgttagagat cataggtggc   26880
attgcctact ttttacataa ttttatcatg tttagtgatc tgtcagaagg gctgtggctg   26940
tttgcagttt tggcttaagc catgcatggg ctttatagga gatgtagtct tcacagtgag   27000
ttgttatttg tagctgtgtt tttgtttttg tatagcttat agcaatgcag tgtgcttttt   27060
attaacatca ttttcttttt cttttttgcag tgattattta ttcaagttac ttctgattgg   27120
cgactcaggg gttggaaagt cttgccttct tcttaggttt gcagtaagtt gaaattgaaa   27180
tgtctttaca attaatggta caattaatgc tatgtatgtt ttctaggtag ataaaattaa   27240
acagttttat tcagaataag ttaattcttc cagaatttat atatttaaag actccaaata   27300
tacatcccca gtggtatctt ggactgttaa atagaaaaat attgttgctc ttaaaagaaa   27360
ttcagtgaag tctggtttata aagtcagaat gtctaatact tttggtcaga gtcaaacagc   27420
agttccaata taggcagcaa gttaaagggg tagttggtgg cctgtgttga aagcgacttg   27480
atgaaaataa atctttaaat taaactttag tagaataaaa agaaaaagca gagccaggtg   27540
acgcagtgga tcatgcctgc agtctcagct actcagggtg ctgagggtgg aaggatcact   27600
tgagtctagg agttttgaga ccaacctgga caacatagca tgactctgtc tctgaaaaaa   27660
aaagttaata aaagaaaaag tagggtcttg acaaacttc gttggccaat ggcatagttc   27720
taaatgctga agctgacaga taaggactt ttgacttaac agaatccaca gtgtccttca   27780
tagtctttat caactaccttt taaatttagc atgtttcctg gccaggtgcg gtggctcacg   27840
cctgtaatcc cagcactttg ggaggccgag acgggcggat cacaaggtca agagattgag   27900
accatcctgg ctaacacggt gaaaccccgt ctctactaaa aatacaaaaa atcagctggg   27960
tgtggtgcca cacgcctgta gtcccagcta ctcgggaggc tgaggcagga gaatcgcttg   28020
aacccaggag gcggaggttg cagtgagctg agatggtgcc actgcactcc agcctggcaa   28080
cagagcaaga ctgtctcaaa aaaaaaagaa aaaaataaa aaaacaaatt agcatgtttc   28140
ccttctagag atcattgttt ctcagagcat ggaccaaaga ctcctggggg ttaccaagac   28200
cctctcaggt agcccatgag gtcaaaatat cctaataata ctaagatgtt agtatttgta   28260
aggaaatatt tacttggtaa taatactaat ataaagatg tttgcgtttt tcagtgatga   28320
cattggctct ggtacaaaag catgtgggta aaattgctgc tggcttggta cacatcaagg   28380
cagcgctaag ctccaaattg tactcatggt gatggcattc tttacctctg tgccctcaca   28440
ggaacaaaaa caagccgtgc cattttattt gaagattgtc cttgacaaaa cagttaaaat   28500
gattaatttt tgaaaaatgt tgatccatga gtattccttt aaaatatttt gtgaagaaat   28560
gggaagttca cataaaacaa tgtttttttt ttgtttttttt tttttttttt ttttgagaca   28620
gattctggct gtgttgccaa ggctagagtg cagtggcgtc tggctcccag gctcaagctg   28680
ttctcccact tcagcctccc aagtggctgg gacctcccaa gtggatgcgc catcatgcct   28740
```

-continued

```
ggctgatttt tgtattttt tgtagtgaca aggtctcact gtgttgcaca ggctggtctc    28800
aaacttctga gctcaagcga tgcatgtgcc tcagcctccc aaagtgctgg agaaagcact    28860
ttttactgca tactggctag tgtgttggtt attttggaga aaagaaaagc atttgtagtt    28920
ttttgagttg taagctgagc taactgcttt attttttttct gtggaacacc atttctttttt   28980
ttttttttga gatggaatat tgctttgttg cccaggctgg agtgcagtgg cacaatctcg    29040
gctcactgca acctccgctt ctcgggttca agcaattctt ctgccgtagc ctcccaagta    29100
gctgggatta taggcacctg ccaccaagcc cagctagttt ttgtatttt agtagagatg    29160
gggtttcacc atgttggcca ggctggtctc gaactcctga cttcgtgatc cgcttgtctc    29220
agcctcccaa agtgctggga ttacaggcgt gaactactgc acctggacat tttttttttt   29280
ttttaactt gaaagaacag ctaacagaca gattagaaca gaattggcta tttgacagat    29340
tttctcagat gaactgtgat agtcatttca agggaagtag ctgcaagcat tgttggctg    29400
aaataaaatt taagtttatc atggaaaatt agaatttgaa aaacttaga gtttaccact    29460
tgacagtatc ctaaatacat atgacttttc tgatgagtgc cgatattaat gaaggttatt    29520
taaaaaatat taaataatgt ataattcttt ttatataaca gttaaaaata aaccatgag    29580
tactagaata aaacataggt ggctctttaa tcttggtttg tgaaggtatt ttttaaaata    29640
agaaaaaagc aagaaatcac tgctaaattt gactattaaa attaatttat cacaggcaca    29700
aaatgttag aaaactaatg gcaatagcaa atatatatat atgaggattg gtattctcaa    29760
catataaagc acatttgcac atcaacaaga aagaatatt tctcctaatg gaaatagtgg    29820
caaatacatg agcagtcagt tgaaaaaga agtaatacaa attgctggct gggtgtgggt    29880
ggggtcacgc ctgtaatccc agcatttaga ggctgaggct ggcggatcat ctgaggtcag    29940
gagttcgaga ccagcctgac caacatggag aaaccctgtc tctactaaaa atacaaaatt    30000
agccggatgt ggtggcgcat gcctgtaatc ccagctactt gggaggctga ggcaggagaa    30060
ttgcttgaac ccaggaggcg gaggttgtgg tgagtcgaga tcgcaccatt gcactccagc    30120
ctgggcaaca agagcgaaac tccatctcaa aaaaaaaaa aaaaaaaaaa aaaaggaagt    30180
aatacaaatt gccaataaat atggaaaaaa aaaaaggctc aactttattt gtaattaaag    30240
gcctttaagt taaacttagg tgtcattaa tttttattaa attggcaaat attaaaatta    30300
agcataattc ttaagcaact ctcggtaggt gggaagaatc tagctgtagc ctcaggtgtt    30360
tgtgcctcaa ggaaaaccct ctctgggatg tccattgctt gaagtcaaag gttttccaat    30420
aatacctgga aactattttt aaaatgctga tcccatacc ctcaaaatat taatagagac    30480
aatcgtgagg actataataa agaaatgtgc aataagctct gggggcacag agggaagaat    30540
ctattggctg aggagttgaa gaaattgttt ggacactcag tattgcctga gctcaaaact    30600
gaaggatgaa taaatgccac atgaccttgg ggctggggag taagtagggt tatgcagaga    30660
gagataactg aggcttttgg gcagacgaat agtaacggct caggcatggg agtaaaggtc    30720
atttagagat ttacaagaat tcagcatttc tttctttttc tttttttttt ttgagatgga    30780
gtctagctct gtcatccagg ctggagtaca gtggcatgat ctcagctcac tataactccc    30840
acctccgggg ttcaagtgat tctcatgcct cagcctcccg agtagctggt attacaggcg    30900
tgtactactg tgcctggcta attttgtat ttttagtaga gatggggttt caccatgttg    30960
gtcaggctgg tctccaactg ctgagctcaa gtgatatgtg cacctctgct ccccaaagtg    31020
ctgggattac aggcgtgagc cactgtaccc ggccaagaat tcagtatttc tatccaagta    31080
cctgggggat agatgtgcta catgaatatt tattgcattc attttgttct ctgcattttt    31140
```

```
tttttttttt ttggtttgag atggagtctc gctctgtcgc ccaggctgga gtgcagtcgt   31200
gcaatctcgg ctcactgcag cctccacctc atgggttcaa gcgattctcc atcttggtct   31260
cctgactagc taggtttaca ggcgtgtgcc atcacaccca ctaattttt gtattttag    31320 tagagacagg gtttcaccat gttggccagg ctggtcttga actcctgatc taaagtgagc   31380
ctcccacctt ggcctcccaa agtgctggga ttacatatgt gagccactgc gcctggcctc   31440
tatatacttc tatagtacct gatacttatt aggcactcaa ttacaacata actttttt    31500 tttttttttt ttttgagaca gagacatgcc ttgtcgcctg gctggagtg cagtggcaca    31560 gtctcggctc actgcaacct tcacctcccg ggttcaagtg attctcttc ctcagcctcc    31620 cgggtagctg ggattacagg cgcccgccac cacgtccagc taatttttg tatttaat    31680 agagatgagg tttcaccatc ttggccaggc tgatctcaaa ctcctgacct tgtgatccac   31740
tcaccttggc ctcccaaagt gctggtatta caggtgtgag ccatcatgcc cggcccatat   31800
ttctaaaaac attttcttat aaaatgacat tgccattatc aacctgcaaa atacatttcc   31860
atttggttgt tttcttgctt agtcttttaa tctagagttt tataccttat ctttttatt   31920 tatatttt ttatgtcatt gacttttgc agaaactgaa gcacttgtcc tgtagattgt    31980
ccaatattct agatttgtca ttttgtttcc ttgtgatgtc cttatgctta tttgtttgtc   32040 cctcttctg taattagaag acctagaact gcactatcct tagagtagct actagctcta   32100
tgtagctatt taaatttaaa ttaattaaaa ttgaaaagt ttggtggctc acctgtaa     32160 tcccagcact tgggaggcc aaggtgggag gattgcttga gtgcaggagt tcaaggcttc    32220
agtaagctac gattgtactc tagcctggga gacatcaaga ccctgtccct ttaaggggga   32280
aaaataattg aaaaaatcaa aaacttagtt tccttgtttc acaagctgca tagggctaat   32340
ggctaccata ttggctagca cagcttatag aacctttcca ttgtcacaga aagttctgtt   32400
tggcagtgcc gttctcatta gacctgattc gattaaggtc catctttgtt gacagagtac   32460
ttcttaggtg gtgctttgtg gttcatatga tgatagcctg gtctgttcat tcatatatct   32520
tttcacgaga aatattttta ttccattctg aataaaattt catggcaggt acttgcaaga   32580
agcagttata attttaaagt ttaacattag gttaaaaaat tgacaggaaa catatattca   32640
caggtaaaac ttgtacacaa atgttcatgg cagcattatt cataatagcc aagaagtgga   32700
aacaacccaa atcaatttat gaatggataa aatgttgtat atttgtagta catgtaatat   32760
tattcagcca ataaaatggg ccaggcatgg tggctcacac ctgtaatccc agcactttga   32820
gaggctcagg caggggatc actagaggtc aggagtttga gaccagcctg accatcatca    32880
cgaaaccctg tctctactaa acgtacaaaa attaggcagg cgtggtgatg cacgcctgta   32940
gtccctacta ctcaggtggc tgagtcatga ggattgcttg gaccccggga gacagaggtt   33000
gcagtgagct gagatcatga cactgcactc cagcatgggc aacagagcaa catcctgcct   33060 caaaaaaaa aaaaaaaaa aaaagaagta ctgttcatg gtacaacatg gatgaaccctt     33120 gaaacattc tgctaaatga aggaagacag acacagaggg ccacatattt tatgattcca   33180
tttatacgaa atgtccaaaa ttggcaaatc taaagagaaa gtagattagt ggttgccagg   33240
gagtgaagac gggttctttc tggagtgaag aaaatgtcct ggaattcgtg gttgtagttt   33300
gcaaccttgt gaatgtataa ggaccactga attgtccact tcaaagggg gacttttatg    33360 ttatgtgcat tatatctaaa aaaaaaatca taattaggaa gcaagattga cttctaagaa   33420
aaagcggagt gaaattgttg ttttgtggtg aataaattgg gtgggtgggt cgcaagagtt   33480
ttgctgatta gtgattagaa aaattattca taatcattga aaatataaaa tatttttcta   33540
```

```
tatgatgtat gtaaagaatt tggcaagaga tgatgtttgg aaaaaataaa gaatggctat    33600
tgtagagatc ttaaggaaag aaactacagt taagtagtgc tttgtaatca gaatatgaag    33660
taagtactga aagtggatgg agtggctgtt gtcagcatgt tatactttat acatttcatt    33720
cataaatttg gactgtagat aaaagtaaac ttttttttta tttactcttg aacaacagtt    33780
tttttttttc cacttagact tgcatctgct ccactgaaca atacatttaa ttgttaatta    33840
tttcccccct caggatgata catatacaga aagctacatc agcacaattg gtgtggattt    33900
caaaataaga actatagagt tagacgggaa aacaatcaag cttcaaatag taagtgactt    33960
ggctagtaat ttttttgaaa tttattttgg taaatttgta atgtattgtt attttgtata    34020
tatttactat gctaacaaaa ttgaatgtaa aatgtcttaa gattcatgta cttaagatag    34080
aatggtagaa taagaattac ttagattaaa aataatattt tcaagattac ttaagcctca    34140
ttgaattttc tgttcatgaa gcagagaaac tcatgtttta agtcaaactt ggtcctcatc    34200
ttttttcttt atcagtggaa atctaagttc aagtttacct tgtcctacac tgcaaatgtt    34260
atagaccatt tttgtttgtc ttttactgtg ctaagtgcat ggaacattaa aggaaccctta   34320 ggaagagatt cttcatatgt ggctcagttg aagagaagta cttatgtagt tctaagtatt    34380
tttattagat agtgtgcacc aactctgtag aaacacagaa ttttgttgga aaaaggaact    34440 tagttttttgt aacatgttca ttttactgct caaaaaaacg aatgctgaaa gatttaatga    34500
cttgcctaca gttactggta gaaccaagtg accgaagctc tgtcttcaat attttgtgtc    34560
tgtgtgccat cctatccccc ttatccatct ttacaccccc agcccccaat taaatatagg    34620
caattataat agttcagttg tgcctcttca gtatgggtct gagtcctgtc agtgtgggca    34680
tatctgtggt cttttaaaaa ataaatctct cagtattttt cagagtaggc tattagcaag    34740
aagtaggcta taaacacagg aaaccagtga ctgccccttt tcatggaact gatgacacat    34800
ggaattggaa ggagtcctgc attaggagtc agaagactta gatttgttgt cttggttcta    34860
gtatttacct gttagagaat catgggtttg tgtctctggg gaaaaggccg aagtaaccct    34920
gagacccagt ttcctttcta aaatgtgtgt gatgacacct gatttactaa tttataagct    34980
agttgtgaga accaactgta atagctttgt gtatgtgaca atacgtgtga aagccctttg    35040 taaactttttg ggcagcatat agatactact tatgatatga catgcccaga taaatgggtg    35100
tttgataggt taagttgctc ccttttctta catgactctg atgaggaaaa gaaggtatgt    35160
taacaaaaga taggtggctg tggatattga tataagtaaa cacacttgat gtgtcaaatt    35220
aggacttgca aggatttagt tttcagaaat agcttgaaat actttcaatc agtgaacaaa    35280
ttaccctcca tatttttttcc cacgatataa gtacagtctc aacctttttat ttggcaccat    35340 aaaagagcaca taaagatcta cccaaaactg tactttaaag cactggtatg gaataattgt    35400
attatgtgtg atcattggtg tttataagat ttgggtgtgt attcgtgtgt gaaacattca    35460
tattttgtta ctttcctgtg gctggaaggg atcttatagg acactgtctt tcatctttgt    35520
ctgtctttca tctttaatag gaatttcttt tccatgcctg aaggcctcat tttgaacatt    35580
ttgtttgttt gtttttttat tttttgagat acagtattgc tctgtctccc aggctggagt    35640
gcagtggcgc gatttgagct cactgcaacc tccgcctcct gggttcaagt gattctcctg    35700
cctcagcctc cctaatagct gggattacat gtgtgtacca ccatgcccgg acaatttttt    35760
tttttttgag atggagcctt gctttgtcgc ccaggctgga gtgccagtgg tgcaatcttg    35820
gctcgctgca gcctccgcct cccaggttca agcagttctc ttgcctcagc ctcctgagta    35880
gctgggatta caggcgtgcg ccaccacacc ctgctaattt tttgtatttt tagtagagac    35940
```

```
agagtttcac catgttggtt aggctggtct cgaactcctg acctcgtgat ctgcctgact    36000
cggcttccca aagtgctggg attacaggca tgagccactg tgcccagcct tccgataatt    36060
tttgtatttt tcgtagagat gggatttcgc catgttggcc aggctggtct caaactcctt    36120
acctcaagtg atccacccgt cttggcctcc caaagtgctg ggattacagg cgtgagccac    36180
cacgcctggg ttttgaaca ttttaagaa gcttaccatt ttttcgaaat agctagttcc      36240
attttacaca taacttcagc taggcatgtt gcctcatgcc tgtaatccca gcactttggg    36300
aggccgaggt cagagagtca cttgaggcca ggagtcaaca tagctcctgt gaccagcctg    36360
gtcaacatag agactctatc tctaccaaaa aaaaaaaaa aaaagtaac caggtgtggt      36420 ggtccatgcc tgtagtccta gctccccagg agactgaggt gggaggaatg tttgagccca    36480
ggacttcaag gctgcagtga ggcaagattg caccattgca ccccagcttt ggggacagag    36540
tgagagaccc tgtctcaaaa acaaaataag gctgggcgca gtggctgtcc gggcgtcgtg    36600
gttcacgctt atagtcctag cactttggga ggccaaggtg gcagattgc ctgagctcag     36660 gaggtctaag accagcctga gcaacatggc gaaacctcat ctttgcaaaa catacagaaa    36720
aaaacaaaaa aaaccacaaa acctctagtt gccagttatt ttttttattt attcctagtg    36780
attcttcttt ttttctttt tctgagacaa aaatttcact ttgtctccct cgctagagtg     36840
cagcggtcag ctcactacat gattctttta gagacatgtt aattctttat attgagctga    36900
agcctgtttc ttttacttct gtctcttctt attcctccgc cttgtagagc tgcctgaatc    36960
agattaattc ctcttttatt ggcaagcctg cccttcagat tgatcttatc acaacctttc    37020
ttctacctct gaagtcctca ttctttcctg taatgatatt ttcagaacct tgtgcaattt    37080
gggttattct tacattttat aaatgccttt tattaaattt gatttcttaa atcaagtatg    37140
agatataaca catgaggtaa atcctgtctt gatttggagc ctgaatgaat ttctctcttg    37200
aacttcaagg gctcatggcc ctttcttatt attaatcaaa gacaaccatt tgttgtttca    37260
gtagctatat tatttctagt ttgggtctta aggttttga tttgcttgtt ttttcttttt     37320 tcttttttt tttttgaga cggagtttcg ctcttgttgc ccagactggg agtgcaatgg      37380
cgtgatctcg gctcactgca acctccgcct cccaggttca agcgattctt ctgcctcagc    37440
ctccctagta gcagggatta caggcatgtg ccaccacgcc gggctaattt tgtattttta    37500
gtagagatgg ggtttctcca tgttggtcac gctggtctcg aactcccgac ctcaggtgat    37560
ccgcctgcct tggcctccca aagtgctggg attacagtcg tgagccacgg cgcctggccg    37620
atttgcttgt tttaattaa ataggggcc ttggccaggt gcagttgttc acccctgtaa      37680
tcccagtact tgggaggct gaggcaggca gatctcttga gttcaggagt tcaagaccag     37740
tatgggcaac atggtgaaac cctgtctcta ccaaaaacac aaaattcagc caggcatggt    37800
ggtgtgtccc tgtagttcaa ggtactcagg aggctgaggt gggaggattg cttgagcccg    37860
gagatggagg ttgcggtgag ccaagattgt gccatttgca ctctagcctg gcaacagag     37920 cgagaccttg tttcaaaaaa aaaaagaag agggtctcac tttacacttc tgtgactggt    37980
gttttaaaaa tctaaacaca ggccgggcac ggtggctcac gcctgtaatc ccagcacttt    38040
gggaggcaga ggcacgcaga tcacaaggtc aggagttcgt gaccagcctg gccagcatgg    38100
tgaagcccat ctctactaaa aatacaaaaa aattagctgg gcatggtggc aggtgcctgt    38160
aatcccagct acttgggagg ctgagacagg ggaatcactt gaacccagga ggcggagatt    38220
gcagtgagcc aagattgcgc cattgcactc cagcctggtg acagagcgag actccgtctc    38280
aaaaaaaaaa aaaaaaatct aaacacaaga ttttacttt aatcctatca tttcctcttg     38340
```

```
cttggcttca gtaatccttc aagttttcta ggtcttttca aaatcttgat tctgttgatt    38400
tatattttaa ttatcttttc ctttcagctt ttcctgttca ggtgtgacat ctgggtcttt    38460
atctgagttt tattagatta taaaacattc agcaagatag ggcaggtact gagtccagtt    38520
gtacaccatg gaaggcctct ttctgtgatt gttcattcat gaggctttat gaaaatgtct    38580
acattacacc aggcacttgg aggttacaga gatgaataaa acatagtcca ttaggaggca    38640
gacaatggga gagacaaaca tgggaaaaag ttactctgat tatgaggagt aatgagaatt    38700
acatatgaag gaaagtattg ttagtactgt taggatttag tgtcaggaaa gttttcagag    38760
tagcaaggaa acatcagaaa ttttactctt tctgccaggc atggtgcatg tattattctg    38820
ttctcacact gccacaagga actgaccaaa actgggtgat ttattaaaaa aaaggtttaa    38880
ttgactcata gttctgcatg gctgaggagg cctcaggaaa cttactgtgg cagaaaggga    38940
agcaggcacg tcttacatgg caggaggcga gagagtgtga aggaagtgaa gggggaagag    39000 cccccttatga gaccatcaga tcttgtgaga attcattcac tatcactcga atggggggaaa    39060 ccgtcgtcat aatccaatca cttctccata atccaatcac ttccctcagt gattacaact    39120
tgagatgaga tttgggtggg gacacagagc caaaccatat cagtgcctgt agtcccagtt    39180
acttggaggc tgaggcagga ggaacacttg agcccaggag ttcaagatct gcctgggcaa    39240
catagcaata cctccatttt ggataaaaag gaaatttttac tttttgggtg ccattgctta    39300
gtttaatcag ctgtaacttc ttgttgactt ttagtcaaaa acaattttt ccttctatct    39360 ttgtgaaaga ggttggtgag caaggaagaa aaggaaactt gctttattga gcagcttcta    39420
tagtcaggca cattttacaa acattagttc atttaaaccc ctttagctgt tgtacaaggt    39480
gaatgctatc tagcatttac agatgaagaa actgttaggt gactctccct aatattaaat    39540
aaccaggaac ctggatttga tgttttgaag tcagggtagc ttgatcctcg agttcatgct    39600
tcctccaagg atacactgaa agactttgag cctcttttt tttttttctc ttttttttgag    39660 acaggatctg gctctcttgc ccagagtgca gtggtgtgat ctcagctcac tgcaacctct    39720
gcctcctggg ctcaagcgat tctgcctcag cctctcgagt agctgggacc acaggcgcac    39780
gccagcatac ttggctaatt tttggatttt tagtagagac agggtttcac catgttggtc    39840
aggctggtct cgaactcctg agctcgtaat ccgcccgtct cggccccaca aagtgctggg    39900
attacaggcg tgagccaccg acccagtccc aacagttttt taaaacccag aactataatg    39960
caataatgtt agcatttgtt tgggagtttt gagcctaaat ggttgaagtg cagtaaattg    40020
ttcttaaaat acgttttatg aaagtatttg gagtctcttc cttacatttt tttctctagc    40080
atgaagacaa cacctagcca ggcatggtgg ctcatgccag taatgccagc actttgggag    40140
aatgagttag gataattgct tgagtccagg aatttgagac cagcctgggc aatgtagcga    40200
gactctgtct ctacaaaaaa gaaaaaatta gccgggtgtg gtggcatgtg cctgtagtcc    40260
cagctactca ggaggctcag gtggaaggat tgcttgaggt gggaggttga ggctgcagcg    40320
agccatgatc atgccactgt actcagcctg gatgacagaa tgagacgctg cttgagaggg    40380
gaaaaaaaag acacctgctt gggatgatta agttctgtc ttgactggta gttatttgaa    40440
ttaggtccct ccagtgcttt taatcatggt agaatgtgct agcaagtgag tttgtcttac    40500
atggaagagt tctgtgttca agggctttcg gccagtggca ttcctaaaca cagtgttaaa    40560
ggcggtaggg aatgtgaaaa gtatgacata gttcctgctc tcaacagctt gtaattttag    40620
tattattatc gtaagctcaa ttgtaggtac tacttctttt ctggactttc aggtgcttat    40680
taccgtgcaa tttagtggta tgagttgagg actaatgttt ctatatcaca tcctgataat    40740
```

```
ctccacagtt atgaaaacta aactatttcc cctccctcct acacttttcc ccaactttat    40800
tttaatggaa ttgtttggat ttcttgattg ttttgtaata gtgggacaca gcaggccagg    40860
aaagatttcg aacaatcacc tccagttatt acagaggagc ccatggcatc atagttgtgt    40920
atgatgtgac agatcaggta agttccaaga ggagattgtg ttacagtgac caagtaggaa    40980
gccattattt gattaatgtc agattcattt actacttcat atataagcca tcagtattaa    41040
ttttatggca gaaaactttg tccactctca aatataaatg tgaatcactt aaaagacatt    41100
tgttttcctg taataaataa aagattagta attagttttta cgtttgcttt caagggattc    41160
tggttgtatt tattgtcaac taaataactt tgatcaaata gccaagactc taacatatag    41220
gcaagagttt gtagggaatc gtgagttgct tggcttatac tgtgttcttg gtgttaagta    41280
ttaacaggaa tatggcctgg taattagaac ttgtccatca gaattgccaa agtgggatt    41340 cgggggtctc tgcctatgga ggatgtggtt cagaaataaa gaatttgaat aggataagct    41400
gtaggaggat cttagtatga gaatgagtat ctgaagatta gctgtgagag agggcagagc    41460
gatggaggga acaatgtggg acagtgtgaa gcatgtgatc cagggggccat aacttttttt    41520 gttactattt ttttaaatca gaaacttaga tttcagtgtc ctttctatca aagaaaagga    41580
caaaagataa acgttcaaaa ttggaattta tttttctttt ggcaaatgtt aaatctcacc    41640
tctaatgaga aatcatagct aattaggaga taacttacat gtaagcattt agattcagtg    41700
ccattagaag tgctgggtgg gtgatatctg caggagaaaa aaatgatgct agtttaaaaa    41760
atctctacta ttaccgtgaa atatttttaa atgaaaactt tcgtcctcta aatatgactg    41820
tggaaaagaa aatgagtata tttaataaca tcttttgaca tctctagtag taacagtagg    41880
tcatcttatt cataaaccaa aattttacca aatttcaggc caggcgcagt ggctcatgcc    41940
tgtaatccca gaactttggg aggccgaggc gggcggatca cctgaggtca ggagttagag    42000
actagcctcg ccaacatggc aaaatcccat ctctagtaaa aatacaaaaa ttagccaggc    42060 gtggggccc gtgcctgtaa tcctagccac ttgggaggct gagacaggag aatcgcttga    42120
acccagcggg cagaggttgc agtgagccga gatcgcgcca ttgcactcca gcctggatga    42180
cagaacaaga ctttgtctca aaaaaaaaa aaaaaaaaa aaaaaatta atcaaatttc    42240 aaaaccaggt tttgtagtac atttaaattg catattccaa agcagttggg tttgcctgcg    42300
ttgcagttta atattaagct atacttccct ttcaaataag gtattttcat cgttaagcct    42360
gtaaattcta gtttgtcatt gtttagatat ttatagtcat tttaatatat ctgtttacgg    42420
ccagctgcaa tggctaacac ctgtaaactc agcactttt gaggccaagg tgggccgatt    42480
gagctcagga gttcgagacc agcctgggca acatagtgaa actccatcta tacaaaaaat    42540
ccaaaaaaaa aaagacaggt gtggtggcat gtgcctgtag tcccagctat cccggaggcg    42600
gaggcgggag gatggcttga gcttgggagg tcgaggtgc agtgagctgt gattgtgcca    42660
ctgcactccg gcctaggtga cagagcaaga ccctgtctca aaaaaaaaa tctcttcact    42720 ccttagcagt ggttatttttg tagctagagt tgtctcacta gctctttgtt atttgtctgt    42780
taggtcagga acgatgtttc tgtttattcc agaactatat tatcgaacta tattatcagt    42840
ctttcaaatg tcttttttagg agtccttcaa taatgttaaa cagtggctgc aggaaataga    42900
tcgttatgcc agtgaaaatg tcaacaaatt gttggtaggg aacaaatgtg atctgaccac    42960
aaagaaagta gtagactaca caacagcgaa ggtatgttta agtttaattt ttcatactga    43020
atttgaaggt gttgaattat gtatgggttc tgcagtaaca gtaaggccac agccttttaa    43080
aaatatgtgc actagaatac tgtgacagtg acaatttgtg tagcatctgt ttggatccaa    43140
```

```
tgaacttagt tcctcacgct ccattatgga tggtagaaat gcagtaagaa ttagtgaaaa    43200
agatttttca gtgttaattg tgcctcatta ttctcttagg aatttgctga ttcccttgga    43260
attccgtttt tggaaaccag tgctaagaat gcaacgaatg tagaacagtc tttcatgacg    43320
atggcagctg agattaaaaa gcgaatgggt cccggagcaa cagctggtgg tgctgagaag    43380
tccaatgtta aaattcagag cactccagtc aagcagtcag gtggaggttg ctgctaaaat    43440
ttgcctccat cctttctca cagcaatgaa tttgcaatct gaacccaagt gaaaaaacaa    43500
aattgcctga attgtactgt atgtagctgc actacaacag attcttaccg tctccacaaa    43560
ggtcagagat tgtaaatggt caatactgac ttttttttta ttcccttgac tcaagacagc    43620
taacttcatt ttcagaactg ttttaaacct ttgtgtgctg gtttataaaa taatgtgtgt    43680
aatccttgtt gctttcctga taccagactg tttcccgtgg ttggttagaa tatattttgt    43740
tttgatgttt atattggcat gtttagatgt caggtttagt cttctgaaga tgaagttcag    43800 ccatttgta tcaaacagca caagcagtgt ctgtcacttt ccatgcataa agtttagtga    43860
gatgttatat gtaagatctg atttgctagt tcttccttgt agagttataa atggaaagat    43920
tacactatct gattaaatagt ttcttcatac tctgcatata atttgtggct gcagaatatt    43980
gtaatttgtt gcacactatg taacaaaaca actgaagata tgtttaataa atattgtact    44040
tattggaagt aatatcaaac tgtatggtga taagtattgt tttgattctt atggttaaag    44100
ggaaatagag ccttgcatta tattcaacac agccatttgt gtgtgcacaa tgcaaactaa    44160
ggtattctag acctatctta gagcagcatc cagtatttgc tttctagata atatgcccaa    44220
taacatgacc tagaggggct tctgtgctgt gtagggattt aaccaacttc agtggttcag    44280
ggagctcaaa ctatatgtaa aacaagttta gaatgtatgc tatctagccc gttatctctg    44340
atccttctct aaaaccattt gaaatagctt cattgatcaa catttcataa atgcatctgt    44400
ggtagaggta gaaagcagca cctttcctaa ttggcaaatg atcagactaa tgtgtgctaa    44460 tgttttctt ccatgctttc agtcagattc aactatttta tcctccacag ttgcttaact    44520
tggtgttgga ggagggttta agcattaaga taggaagcag gaaatttgat tgctctaaat    44580
ttagaaatta tatccctaaa aattaaaaca tgaatactgg gtggtaatga taattgaggc    44640
aaatgtattt attttggtga cattttgcat atatgaagat tttctgaaat aggaccttca    44700
agatcctagg gggttttgtt tggtttttaa ttgtgaggaa taaaaaatct tctgcccaca    44760
ctggcatttt aaggtgactg aggtcaaacg ttgtttcctt aggttgaaat agcagccaaa    44820
acattcttca cgcagggct tgggatatgg ctgctggcaa cacattttgt tgtgggctcc    44880
ttaatttaat gataaaattt aagctaaaca caagccaaaa atgaataggt ttttttaatt    44940 tttattttc actaaacagg caattgaaat acatggtaca aaaataagtg gtaagataat    45000
tgtaaaatga aatggacaga atattcaatt ttccatctat gaaaatttca caataaaaat    45060
catagtttac tttgtattat aggcgtgctt ggtggatcta ttcatcctca cataaggcaa    45120
ctgacaaatt cctgaagtta ccaatagtta ttttggtgaa gatctttaat gcttcagaag    45180
ttttgttttt gccttaatac agtataaagg gggaaagagt tcagaaacta ttttctaaag    45240
tagctaaatg acacaaaaca aatgtcaaga tactgtgatg ccatgccgtg cacttcattt    45300
ttacacagta aaagttgttt aaattgtcag cttattcttg gtgagttagc ggaaacatta    45360
catgaactta agatgagcat atttacagac ttaagtttgg aaaattccag cgttcttttc    45420
cccatggcag taaagattgg gatttacaac aaatttcagc atgccttaag atttgcttct    45480
atgtatacgc caataaatgt ggttctggaa aaaatatata cccctttata cccccatttt    45540
```

-continued

```
caagtacaaa cggttcaaag ctactacagg tttaataat ctgttcactt agtaaaggga    45600
attaccactt gttctaaata taaggtgctg ccataaatta gtttacatag tgaagaagag    45660
tgttcttaaa tctaagcagc tgcacactct gtgaaatcct ttcagaatga tagtcattgt    45720
ggtctgagca gtaatttcct attcttcgac cttggattga atttcccta gcctacatct    45780
tgcctttcca gcatatctta cctcaaacct tctttgtgtt ccattcccac ctaagcttca    45840
aaatagccct gtgttgacgt cgtcttccat ttgctgagct tacctatgga tctccaagaa    45900
cccagatctt gaaactgctg atccagcttt gagtatcatc acttccctgt ggatttaact    45960
tccattaatt ttaagggact actaagttat tccagtgtgg catcacagtg cagttagcaa    46020
gctcagctac ttgactctaa tttggccatg                                     46050
```

<210> SEQ ID NO 4
<211> LENGTH: 222
<212> TYPE: PRT
<213> ORGANISM: Human

<400> SEQUENCE: 4

```
Gly Gly Cys Gly Ser Lys Gly Gly Gly Gly Gly Ser Cys Ser
 1               5                  10                  15

Asp Met Ser Ser Met Asn Pro Glu Tyr Asp Tyr Leu Phe Lys Leu Leu
                20                  25                  30

Leu Ile Gly Asp Ser Gly Val Gly Lys Ser Cys Leu Leu Leu Arg Phe
            35                  40                  45

Ala Asp Asp Thr Tyr Thr Glu Ser Tyr Ile Ser Thr Ile Gly Val Asp
        50                  55                  60

Phe Lys Ile Arg Thr Ile Glu Leu Asp Gly Lys Thr Ile Lys Leu Gln
65                  70                  75                  80

Ile Trp Asp Thr Ala Gly Gln Glu Arg Phe Arg Thr Ile Thr Ser Ser
                85                  90                  95

Tyr Tyr Arg Gly Ala His Gly Ile Ile Val Val Tyr Asp Val Thr Asp
            100                 105                 110

Gln Glu Ser Phe Asn Asn Val Lys Gln Trp Leu Gln Glu Ile Asp Arg
        115                 120                 125

Tyr Ala Ser Glu Asn Val Asn Lys Leu Leu Val Gly Asn Lys Cys Asp
130                 135                 140

Leu Thr Thr Lys Lys Val Val Asp Tyr Thr Thr Ala Lys Glu Phe Ala
145                 150                 155                 160

Asp Ser Leu Gly Ile Pro Phe Leu Glu Thr Ser Ala Lys Asn Ala Thr
                165                 170                 175

Asn Val Glu Gln Ser Phe Met Thr Met Ala Ala Glu Ile Lys Lys Arg
            180                 185                 190

Met Gly Pro Gly Ala Thr Ala Gly Gly Ala Glu Lys Ser Asn Val Lys
        195                 200                 205

Ile Gln Ser Thr Pro Val Lys Gln Ser Gly Gly Gly Cys Cys
210                 215                 220
```

ISOLATED HUMAN RAS-LIKE PROTEINS, NUCLEIC ACID MOLECULES ENCODING THESE HUMAN RAS-LIKE PROTEINS, AND USES THEREOF

FIELD OF THE INVENTION

The present invention is in the field of Ras-like proteins that are related to the Rab subfamily, recombinant DNA molecules and protein production. The present invention specifically provides novel Ras-like protein polypeptides and proteins and nucleic acid molecules encoding such peptide and protein molecules, all of which are useful in the development of human therapeutics and diagnostic compositions and methods.

BACKGROUND OF THE INVENTION

Ras-like proteins, particularly members of the Rab subfamilies, are a major target for drug action and development. Accordingly, it is valuable to the field of pharmaceutical development to identify and characterize previously unknown members of this subfamily of Ras-like proteins. The present invention advances the state of the art by providing a previously unidentified human Ras-like proteins that have homology to members of the Rab subfamilies.

Ras Protein

Ras proteins are small regulatory GTP-binding proteins, or small G proteins, which belong to the Ras protein superfamily. They are monomeric GTPases, but their GTPase activity is very slow (less than one GTP molecule per minute).

Ras proteins are key relays in the signal-transducing cascade induced by the binding of a ligand to specific receptors such as receptor tyrosine kinases (RTKs), since they trigger the MAP kinase cascade. The ligand can be a growth factor (epidermal growth factor (EGF), platelet-derived growth factor (PDGF), insulin, an interleukin (IL), granulocyte colony-stimulating factor (G-CSF), granulocyte/macrophage colony-stimulating factor (GM-CSF).

Ras proteins contain sequences highly conserved during evolution. Their tertiary structure includes ten loops connecting six strands of beta-sheet and five alpha helices.

In mammalians, there are four Ras proteins, which are encoded by Ha-ras, N-ras, Ki-rasA and Ki-rasB genes. They are composed of about 170 residues and have a relative molecular mass of 21 kD. Ras proteins contain covalently attached modified lipids allowing these proteins to bind to the plasma membrane. Ha-Ras has a C-terminal farnesyl group, a C-terminal palmitoyl group and a N-terminal myristoyl group. In Ki-Ras(B), a C-terminal polylysine domain replaces the palmitoyl group.

Ras proteins alternate between an inactive form bound to GDP and an active form bound to GTP. Their activation results from reactions induced by a guanine nucleotide-exchange factor (GEF). Their inactivation results from reactions catalyzed by a GTPase-activating protein (GAP).

When a Ras protein is activated by a GEF such as a Sos protein, the N-terminal region of a serine/threonine kinase, called "Raf protein", can bind to Ras protein. The C-terminal region of the activated Raf thus formed binds to another protein, MEK, and phosphorylates it on both specific tyrosine and serine residues. Active MEK phosphorylates and activates, in turn, a MAP kinase (ERK1 or ERK2), which is also a serine/threonine kinase. This phosphorylation occurs on both specific tyrosine and threonine residues of MAP kinase.

MAP kinase phosphorylates many different proteins, especially nuclear transcription factors (TFs) that regulate expression of many genes during cell proliferation and differentiation.

Recent researches suggest that, in mammalians, phosphatidyl inositol 3'-kinase (PI3-kinase) might be a target of Ras protein, instead of Raf protein. In certain mutations, the translation of ras genes may produce oncogenic Ras proteins.

Ras-Like Protein

Guanine nucleotide-binding proteins (GTP-binding proteins, or G proteins) participate in a wide range of regulatory functions including metabolism, growth, differentiation, signal transduction, cytoskeletal organization, and intracellular vesicle transport and secretion. These proteins control diverse sets of regulatory pathways in response to hormones, growth factors, neuromodulators, or other signaling molecules. When these molecules bind to transmembrane receptors, signals are propagated to effector molecules by intracellular signal transducing proteins. Many of these signal-transducing proteins are members of the Ras superfamily.

The Ras superfamily is a class of low molecular weight (LMW) GTP-binding proteins that consist of 21–30 kDa polypeptides. These proteins regulate cell growth, cell cycle control, protein secretion, and intracellular vesicle interaction. In particular, the LMW GTP-binding proteins activate cellular proteins by transducing mitogenic signals involved in various cell functions in response to extracellular signals from receptors (Tavitian, A. (1995) C. R. Seances Soc. Biol. Fil. 189:7–12). During this process, the hydrolysis of GTP acts as an energy source as well as an on-off switch for the GTPase activity of the LMW GTP-binding proteins.

The Ras superfamily is comprised of five subfamilies: Ras, Rho, Ran, Rab, and ADP-ribosylation factor (ARF). Specifically, Ras genes are essential in the control of cell proliferation. Mutations in Ras genes have been associated with cancer. Rho proteins control signal transduction in the process of linking receptors of growth factors to actin polymerization that is necessary for cell division. Rab proteins control the translocation of vesicles to and from membranes for protein localization, protein processing, and secretion. Ran proteins are localized to the cell nucleus and play a key role in nuclear protein import, control of DNA synthesis, and cell-cycle progression. ARF and ARF-like proteins participate in a wide variety of cellular functions including vesicle trafficking, exocrine secretion, regulation of phospholipase activity, and endocytosis.

Despite their sequence variations, all five subfamilies of the Ras superfamily share conserved structural features. Four conserved sequence regions (motifs I–IV) have been studied in the LMW GTP-binding proteins. Motif I is the most variable but has the conserved sequence, GXXXXGK (SEQ ID NO:41). The lysine residue is essential in interacting with the .beta.- and .gamma.-phosphates of GTP. Motif II, III, and IV contain highly conserved sequences of DTAGQ (SEQ ID NO:42), NKXD (SEQ ID NO:43), and EXSAX (SEQ ID NO:44), respectively. Specifically, Motif II regulates the binding of gamma-phosphate of GTP; Motif III regulates the binding of GTP; and Motif IV regulates the guanine base of GTP. Most of the membrane-bound LMW GTP-binding proteins generally require a carboxy terminal isoprenyl group for membrane association and biological activity. The isoprenyl group is added posttranslationally through recognition of a terminal cysteine residue alone or a terminal cysteine-aliphatic amino acid-aliphatic amino acid-any amino acid (CAAX; SEQ ID NO:45) motif. Additional membrane-binding energy is often provided by either internal palmitoylation or a carboxy terminal cluster of basic amino acids. The LMW GTP-binding proteins also have a variable effector region, located between motifs I and II, which is characterized as the interaction site for guanine nucleotide exchange factors (GEFs) or GTPase-activating proteins (GAPs). GEFs induce the release of GDP from the active form of the G protein, whereas GAPs interact with the inactive form by stimulating the GTPase activity of the G protein.

The ARF subfamily has at least 15 distinct members encompassing both ARF and ARF-like proteins. ARF proteins identified to date exhibit high structural similarity and ADP-ribosylation enhancing activity. In contrast, several ARF-like proteins lack ADP-ribosylation enhancing activity and bind GTP differently. An example of ARF-like proteins is a rat protein, ARL184. ARL184 has been shown to have a molecular weight of 22 kDa and four functional GTP-binding sites (Icard-Liepkalns, C. et al. (1997) Eur. J. Biochem. 246: 388–393). ARL184 is active in both the cytosol and the Golgi apparatus and is closely associated with acetylcholine release, suggesting that ARL184 is a potential regulatory protein associated with $Ca^{2+}$-dependent release of acetylcholine.

A number of Rho GTP-binding proteins have been identified in plasma membrane and cytoplasm. These include RhoA, B and C, and D, rhoG, rac 1 and 2, G25K-A and B, and TC10 (Hall, A. et al. (1993) Philos. Trans. R. Soc. Lond. (Bil.) 340:267–271). All Rho proteins have a CAAX (SEQ ID NO:45) motif that binds a prenyl group and either a palmitoylation site or a basic amino acid-rich region, suggesting their role in membrane-associated functions. In particular, RhoD is a protein that functions in early endosome motility and distribution by inducing rearrangement of actin cytoskeleton and cell surface (Murphy, C. et al. (1996) Nature 384:427–432). During cell adhesion, the Rho proteins are essential for triggering focal complex assembly and integrin-dependent signal transduction (Hotchin, N. A. and Hall, A. (1995) J. Cell Biol. 131:1857–1865).

The Ras subfamily proteins already indicated supra are essential in transducing signals from receptor tyrosine kinases (RTKs) to a series of serine/threonine kinases which control cell growth and differentiation. Mutant Ras proteins, which bind but cannot hydrolyze GTP, are permanently activated and cause continuous cell proliferation or cancer. TC21, a Ras-like protein, is found to be highly expressed in a human teratocarcinoma cell line (Drivas, G. T. et al. (1990) Mol. Cell. Biol. 10: 1793–1798). Rin and Rit are characterized as membrane-binding, Ras-like proteins without the lipid-binding CAAX (SEQ ID NO:45) motif and carboxy terminal cysteine (Lee, C.-H. J. et al. (1996) J. Neurosci. 16: 6784–6794). Further, Rin is shown to localize in neurons and have calcium-dependant calmodulin-binding activity.

Rab Proteins

The novel human protein, and encoding gene, provided by the present invention is related to the Rab family of Ras-like proteins and shows the highest degree of similarity to Rab1. Rab GTP-binding proteins are similar to YPT1/SEC4 in *Saccharomyces cerevisiae,* which are critical for transport along the exocytic route (Chavrier et al., *Mol Cell Biol* 1990 Dec.;10(12):6578–85). Different Rab proteins are presumed to control different steps in membrane traffic, leading to a high level of diversity and complexity within the Rab family (Chavrier et al., *Mol Cell Biol* 1990 Dec.;10(12):6578–85). The Rab1 gene maps in close viscinity to the 'wobbler' spinal muscular atrophy gene.

RAB proteins are important for regulating the targeting and fusion of membranous vesicles during organelle assembly and transport. RAB proteins undergo controlled exchange of GTP for GDP, and they hydrolyze GTP in a reaction that may regulate the timing and unidirectional nature of these assemblies. Generally, known RAB proteins terminate in sequences such as cys-X-cys (e.g., RAB3A), cys-cys (e.g., RAB1A), or a similar sequence, and generally all are geranylgeranylated.

The tethering factor p115 is a RAB1 effector that binds directly to activated RAB1. It is thought that RAB1-regulated assembly of functional effector-SNARE complexes serves as a conserved molecular mechanism for regulating recognition between different subcellular compartments such as endoplasmic reticulum and Golgi apparatus (Allan et al., *Science* 289: 444–448, 2000).

GTPases play important roles in a wide variety of cell functions such as signal transduction, cytoskeletal organization, and membrane trafficking. Rab GTPases are particularly important for regulating cellular membrane dynamics by modulating the activity of effector proteins that then regulate vesicle trafficking. The Rab8 GTPase plays important roles in Golgi to plasma membrane vesicle trafficking. Studies have suggested that Rab37 plays an important role in mast cell degranulation. Thus, novel human Rab GTPases may be valuable as potential therapeutic targets for the development of allergy treatments (Masuda et al., *FEBS Lett* 2000 Mar. 17;470). Rab15 may act, together with Rab3A, to regulate synaptic vesicle membrane flow within nerve terminals, thereby regulating neurotransmitter release. Rab15 and Rab3A are low molecular weight GTP-binding proteins. Rab proteins are generally comprised of four conserved structural domains necessary for GTP binding, as well as additional domains for membrane localization and effector protein interactions. Rab15 is expressed primarily in neural tissues such as the brain and is localized to synaptic vesicles (Elferink et al., J. Biol. Chem. 267 (9), 5768–5775 (1992)).

For a further review of Rab1 and other Rab proteins, see Wedemeyer et al., *Genomics* 32: 447–454, 1996 and Zahraoui et al., *J Biol. Chem.* 264: 12394–12401, 1989.

Due to their importance in human physiology, particularly in regulating membrane trafficking, novel human Rab proteins/genes, such as provided by the present invention, are valuable as potential targets for the development of therapeutics to treat a wide variety of diseases/disorders caused or influenced by defects in membrane trafficking. Furthermore, SNPs in Rab genes, such as provided by the present invention, are valuable markers for the diagnosis, prognosis, prevention, and/or treatment of such diseases/disorders.

Using the information provided by the present invention, reagents such as probes/primers for detecting the SNPs or the expression of the protein/gene provided herein may be readily developed and, if desired, incorporated into kit formats such as nucleic acid arrays, primer extension reactions coupled with mass spec detection (for SNP detection), or TaqMan PCR assays (Applied Biosystems, Foster City, Calif.).

The discovery of new human Ras-like proteins and the polynucleotides that encode them satisfies a need in the art by providing new compositions that are useful in the diagnosis, prevention, and treatment of inflammation and disorders associated with cell proliferation and apoptosis.

SUMMARY OF THE INVENTION

The present invention is based in part on the identification of amino acid sequences of human Ras-like protein polypeptides and proteins that are related to the Rab Ras-like protein subfamily, as well as allelic variants and other mammalian orthologs thereof. These unique peptide sequences, and nucleic acid sequences that encode these peptides, can be used as models for the development of human therapeutic targets, aid in the identification of therapeutic proteins, and serve as targets for the development of human therapeutic agents that modulate Ras-like protein activity in cells and tissues that express the Ras-like protein. Experimental data as provided in FIG. 1 indicates expression in the adult and fetal brain, adrenal gland, brain neuroblastoma, skin melanotic melanoma, uterus leiomyosarcoma, and placenta.

DESCRIPTION OF THE FIGURE SHEETS

FIG. 1 provides the nucleotide sequence of a cDNA molecule that encodes the Ras-like protein of the present invention. (SEQ ID NO:1) In addition, structure and functional information is provided, such as ATG start, stop and tissue distribution, where available, that allows one to readily determine specific uses of inventions based on this molecular sequence. Experimental data as provided in FIG. 1 indicates expression in the adult and fetal brain, adrenal gland, brain neuroblastoma, skin melanotic melanoma, uterus leiomyosarcoma, and placenta.

FIG. 2 provides the predicted amino acid sequence of the Ras-like protein of the present invention. (SEQ ID NO:2) In addition structure and functional information such as protein family, function, and modification sites is provided where available, allowing one to readily determine specific uses of inventions based on this molecular sequence.

FIG. 3 provides genomic sequences that span the gene encoding the Ras-like protein of the present invention. (SEQ ID NO:3) In addition structure and functional information, such as intron/exon structure, promoter location, etc., is provided where available, allowing one to readily determine specific uses of inventions based on this molecular sequence. As illustrated in FIG. 3, SNPs were identified at 25 different nucleotide positions.

DETAILED DESCRIPTION OF THE INVENTION

General Description

The present invention is based on the sequencing of the human genome. During the sequencing and assembly of the human genome, analysis of the sequence information revealed previously unidentified fragments of the human genome that encode peptides that share structural and/or sequence homology to protein/peptide/domains identified and characterized within the art as being a Ras-like protein or part of a Ras-like protein and are related to the Rab subfamily. Utilizing these sequences, additional genomic sequences were assembled and transcript and/or cDNA sequences were isolated and characterized. Based on this analysis, the present invention provides amino acid sequences of human Ras-like protein polypeptides that are related to the Rab subfamily, nucleic acid sequences in the form of transcript sequences, cDNA sequences and/or genomic sequences that encode these Ras-like protein polypeptide, nucleic acid variation (allelic information), tissue distribution of expression, and information about the closest art known protein/peptide/domain that has structural or sequence homology to the Ras-like protein of the present invention.

In addition to being previously unknown, the peptides that are provided in the present invention are selected based on their ability to be used for the development of commercially important products and services. Specifically, the present peptides are selected based on homology and/or structural relatedness to known Ras-like proteins of the Rab subfamily and the expression pattern observed. Experimental data as provided in FIG. 1 indicates expression in the adult and fetal brain, adrenal gland, brain neuroblastoma, skin melanotic melanoma, uterus leiomyosarcoma, and placenta. The art has clearly established the commercial importance of members of this family of proteins and proteins that have expression patterns similar to that of the present gene. Some of the more specific features of the peptides of the present invention, and the uses thereof, are described herein, particularly in the Background of the Invention and in the annotation provided in the Figures, and/or are known within the art for each of the known Rab family or subfamily of Ras-like proteins.

Specific Embodiments

Peptide Molecules

The present invention provides nucleic acid sequences that encode protein molecules that have been identified as being members of the Ras-like protein family and are related to the Rab subfamily (protein sequences are provided in FIG. 2, transcript/cDNA sequences are provided in FIG. 1 and genomic sequences are provided in FIG. 3). The peptide sequences provided in FIG. 2, as well as the obvious variants described herein, particularly allelic variants as identified herein and using the information in FIG. 3, will be referred herein as the Ras-like proteins or peptides of the present invention, Ras-like proteins or peptides, or peptides/proteins of the present invention.

The present invention provides isolated peptide and protein molecules that consist of, consist essentially of, or comprise the amino acid sequences of the Ras-like protein polypeptide disclosed in the FIG. 2, (encoded by the nucleic acid molecule shown in FIG. 1, transcript/cDNA or FIG. 3, genomic sequence), as well as all obvious variants of these peptides that are within the art to make and use. Some of these variants are described in detail below.

As used herein, a peptide is said to be "isolated" or "purified" when it is substantially free of cellular material or free of chemical precursors or other chemicals. The peptides of the present invention can be purified to homogeneity or other degrees of purity. The level of purification will be based on the intended use. The critical feature is that the preparation allows for the desired function of the peptide, even if in the presence of considerable amounts of other components.

In some uses, "substantially free of cellular material" includes preparations of the peptide having less than about 30% (by dry weight) other proteins (i.e., contaminating protein), less than about 20% other proteins, less than about 10% other proteins, or less than about 5% other proteins. When the peptide is recombinantly produced, it can also be substantially free of culture medium, i.e., culture medium represents less than about 20% of the volume of the protein preparation.

The language "substantially free of chemical precursors or other chemicals" includes preparations of the peptide in which it is separated from chemical precursors or other chemicals that are involved in its synthesis. In one embodiment, the language "substantially free of chemical precursors or other chemicals" includes preparations of the Ras-like protein polypeptide having less than about 30% (by dry weight) chemical precursors or other chemicals, less than about 20% chemical precursors or other chemicals, less than about 10% chemical precursors or other chemicals, or less than about 5% chemical precursors or other chemicals.

The isolated Ras-like protein polypeptide can be purified from cells that naturally express it, purified from cells that have been altered to express it (recombinant), or synthesized using known protein synthesis methods. Experimental data as provided in FIG. 1 indicates expression in the adult and fetal brain, adrenal gland, brain neuroblastoma, skin melanotic melanoma, uterus leiomyosarcoma, and placenta. For example, a nucleic acid molecule encoding the Ras-like protein polypeptide is cloned into an expression vector, the expression vector introduced into a host cell and the protein expressed in the host cell. The protein can then be isolated from the cells by an appropriate purification scheme using standard protein purification techniques. Many of these techniques are described in detail below.

Accordingly, the present invention provides proteins that consist of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). The amino acid sequence of such a protein is provided in FIG. 2. A protein consists of an amino acid sequence when the amino acid sequence is the final amino acid sequence of the protein.

The present invention further provides proteins that consist essentially of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein consists essentially of an amino acid sequence when such an amino acid sequence is present with only a few additional amino acid residues, for example from about 1 to about 100 or so additional residues, typically from 1 to about 20 additional residues in the final protein.

The present invention further provides proteins that comprise the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein comprises an amino acid sequence when the amino acid sequence is at least part of the final amino acid sequence of the protein. In such a fashion, the protein can be only the peptide or have additional amino acid molecules, such as amino acid residues (contiguous encoded sequence) that are naturally associated with it or heterologous amino acid residues/peptide sequences. Such a protein can have a few additional amino acid residues or can comprise several hundred or more additional amino acids. The preferred classes of proteins that are comprised of the Ras-like protein polypeptide of the present invention are the naturally occurring mature proteins. A brief description of how various types of these proteins can be made/isolated is provided below.

The Ras-like protein polypeptides of the present invention can be attached to heterologous sequences to form chimeric or fusion proteins. Such chimeric and fusion proteins comprise a Ras-like protein polypeptide operatively linked to a heterologous protein having an amino acid sequence not substantially homologous to the Ras-like protein polypeptide. "Operatively linked" indicates that the Ras-like protein polypeptide and the heterologous protein are fused in-frame. The heterologous protein can be fused to the N-terminus or C-terminus of the Ras-like protein polypeptide.

In some uses, the fusion protein does not affect the activity of the Ras-like protein polypeptide per se. For example, the fusion protein can include, but is not limited to, enzymatic fusion proteins, for example beta-galactosidase fusions, yeast two-hybrid GAL fusions, poly-His fusions, MYC-tagged, HI-tagged and Ig fusions. Such fusion proteins, particularly poly-His fusions, can facilitate the purification of recombinant Ras-like protein polypeptide. In certain host cells (e.g., mammalian host cells), expression and/or secretion of a protein can be increased by using a heterologous signal sequence.

A chimeric or fusion protein can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al., *Current Protocols in Molecular Biology*, 1992). Moreover, many expression vectors are commercially available that already encode a fusion moiety (e.g., a GST protein). A Ras-like protein polypeptide-encoding nucleic acid can be cloned into such an expression vector such that the fusion moiety is linked in-frame to the Ras-like protein polypeptide.

As mentioned above, the present invention also provides and enables obvious variants of the amino acid sequence of the peptides of the present invention, such as naturally occurring mature forms of the peptide, allelic/sequence variants of the peptides, non-naturally occurring recombinantly derived variants of the peptides, and orthologs and paralogs of the peptides. Such variants can readily be generated using art know techniques in the fields of recombinant nucleic acid technology and protein biochemistry. It is understood, however, that variants exclude any amino acid sequences disclosed prior to the invention.

Such variants can readily be identified/made using molecular techniques and the sequence information disclosed herein. Further, such variants can readily be distinguished from other peptides based on sequence and/or structural homology to the Ras-like protein polypeptides of the present invention. The degree of homology/identity present will be based primarily on whether the peptide is a functional variant or non-functional variant, the amount of divergence present in the paralog family, and the evolutionary distance between the orthologs.

To determine the percent identity of two amino acid sequences or two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, 40%, 50%, 60%, 70%, 80%, or 90% or more of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity and similarity between two sequences can be accomplished using a mathematical algorithm. (*Computational Molecular Biology,* Lesk, A. M., ed., Oxford University Press, New York, 1988; *Biocomputing: Informatics and Genome Projects,* Smith, D. W., ed., Academic Press, New York, 1993; *Computer Analysis of Sequence Data, Part* 1, Griffin, A. M., and Griffin, H. G., eds., Humana Press, New Jersey, 1994; *Sequence Analysis in Molecular Biology,* von Heinje, G., Academic Press, 1987; and *Sequence Analysis Primer,* Gribskov, M. and Devereux, J., eds., M Stockton Press, New York, 1991). In a preferred embodiment, the percent identity between two amino acid sequences is determined using the Needleman and Wunsch (*J. Mol. Biol.* (48):444–453 (1970)) algorithm which has been incorporated into the GAP program in the GCG software package, using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (Devereux, J., et al., *Nucleic Acids Res.* 12(1):387 (1984)), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Meyers and W. Miller (*CABIOS,* 4:11–17 (1989)) which has been incorporated into the ALIGN program (version 2.0), using a PAM120 weight residue table, a gap length penalty of 12 and a gap penalty of 4.

The nucleic acid and protein sequences of the present invention can further be used as a "query sequence" to perform a search against sequence databases to, for example, identify other family members or related sequences. Such searches can be performed using the NBLAST and XBLAST programs (version 2.0) of Altschul, et al. (*J. Mol. Biol.* 215:403–10 (1990)). BLAST nucleotide searches can be performed with the NBLAST program, score=100, word length=12 to obtain nucleotide sequences homologous to the nucleic acid molecules of the invention. BLAST protein searches can be performed with the XBLAST program, score=50, word length=3, to obtain amino acid sequences homologous to the proteins of the invention. To obtain gapped alignments for comparison purposes, Gapped BLAST can be utilized as described in Altschul et al. (i Nucleic Acids Res. 25(17):3389–3402 (1997)). When utilizing BLAST and gapped BLAST programs, the default parameters of the respective programs (e.g., XBLAST and NBLAST) can be used.

Full-length pre-processed forms, as well as mature processed forms, of proteins that comprise one of the peptides of the present invention can readily be identified as having complete sequence identity to one of the Ras-like protein polypeptides of the present invention as well as being encoded by the same genetic locus as the Ras-like protein polypeptide provided herein. The gene encoding the novel Ras-like protein of the present invention is located on a genome component that has been mapped to human chromosome 2 (as indicated in FIG. 3), which is supported by multiple lines of evidence, such as STS and BAC map data.

Allelic variants of a Ras-like protein polypeptide can readily be identified as being a human protein having a high degree (significant) of sequence homology/identity to at least a portion of the Ras-like protein polypeptide as well as being encoded by the same genetic locus as the Ras-like protein polypeptide provided herein. Genetic locus can readily be determined based on the genomic information provided in FIG. 3, such as the genomic sequence mapped to the reference human. The gene encoding the novel Ras-like protein of the present invention is located on a genome component that has been mapped to human chromosome 2 (as indicated in FIG. 3), which is supported by multiple lines of evidence, such as STS and BAC map data. As used herein, two proteins (or a region of the proteins) have significant homology when the amino acid sequences are typically at least about 70–80%, 80–90%, and more typically at least about 90–95% or more homologous. A significantly homologous amino acid sequence, according to the present invention, will be encoded by a nucleic acid sequence that will hybridize to a Ras-like protein polypeptide encoding nucleic acid molecule under stringent conditions as more fully described below.

FIG. 3 provides information on SNPs that have been found in the gene encoding the Ras-like protein of the present invention. SNPs were identified at 25 different nucleotide positions. Some of these SNPs that are located outside the ORF and in introns may affect gene transcription.

Paralogs of a Ras-like protein polypeptide can readily be identified as having some degree of significant sequence homology/identity to at least a portion of the Ras-like protein polypeptide, as being encoded by a gene from humans, and as having similar activity or function. Two proteins will typically be considered paralogs when the amino acid sequences are typically at least about 40–50%, 50–60%, and more typically at least about 60–70% or more homologous through a given region or domain. Such paralogs will be encoded by a nucleic acid sequence that will hybridize to a Ras-like protein polypeptide encoding nucleic acid molecule under moderate to stringent conditions as more fully described below.

Orthologs of a Ras-like protein polypeptide can readily be identified as having some degree of significant sequence homology/identity to at least a portion of the Ras-like protein polypeptide as well as being encoded by a gene from another organism. Preferred orthologs will be isolated from mammals, preferably primates, for the development of human therapeutic targets and agents. Such orthologs will be encoded by a nucleic acid sequence that will hybridize to a Ras-like protein polypeptide encoding nucleic acid molecule under moderate to stringent conditions, as more fully described below, depending on the degree of relatedness of the two organisms yielding the proteins.

Non-naturally occurring variants of the Ras-like protein polypeptides of the present invention can readily be generated using recombinant techniques. Such variants include, but are not limited to deletions, additions and substitutions in the amino acid sequence of the Ras-like protein polypeptide. For example, one class of substitutions is conserved amino acid substitutions. Such substitutions are those that substitute a given amino acid in a Ras-like protein polypeptide by another amino acid of like characteristics. Typically seen as conservative substitutions are the replacements, one for another, among the aliphatic amino acids Ala, Val, Leu, and Ile; interchange of the hydroxyl residues Ser and Thr, exchange of the acidic residues Asp and Glu, substitution between the amide residues Asn and Gln, exchange of the basic residues Lys and Arg, replacements among the aromatic residues Phe, Tyr, and the like. Guidance concerning which amino acid changes are likely to be phenotypically silent are found in Bowie et al., *Science* 247:1306–1310 (1990).

Variant Ras-like protein polypeptides can be fully functional or can lack function in one or more activities. Fully functional variants typically contain only conservative variations or variations in non-critical residues or in non-critical regions. Functional variants can also contain substitution of similar amino acids that result in no change or an insignificant change in function. Alternatively, such substitutions may positively or negatively affect function to some degree.

Non-functional variants typically contain one or more non-conservative amino acid substitutions, deletions, insertions, inversions, or truncation or a substitution, insertion, inversion, or deletion in a critical residue or critical region.

Amino acids that are essential for function can be identified by methods known in the art, such as site-directed mutagenesis or alanine-scanning mutagenesis (Cunningham et al, *Science* 244:1081–1085 (1989)). The latter procedure introduces single alanine mutations at every residue in the molecule. The resulting mutant molecules are then tested for biological activity such as receptor binding or in vitro proliferative activity. Sites that are critical for ligand-receptor binding can also be determined by structural analysis such as crystallography, nuclear magnetic resonance, or photoaffinity labeling (Smith et al., *J. Mol. Biol.* 224:899–904 (1992); de Vos et al. *Science* 255:306–312 (1992)).

The present invention further provides fragments of the Ras-like protein polypeptides, in addition to proteins and peptides that comprise and consist of such fragments. Particularly those comprising the residues identified in FIG. 2. The fragments to which the invention pertains, however, are not to be construed as encompassing fragments that have been disclosed publicly prior to the present invention.

As used herein, a fragment comprises at least 8, 10, 12, 14, 16 or more contiguous amino acid residues from a Ras-like protein polypeptide. Such fragments can be chosen based on the ability to retain one or more of the biological activities of the Ras-like protein polypeptide, or can be chosen for the ability to perform a function, e.g., act as an immunogen. Particularly important fragments are biologically active fragments, peptides that are, for example about 8 or more amino acids in length. Such fragments will typically comprise a domain or motif of the Ras-like protein polypeptide, e.g., active site. Further, possible fragments include, but are not limited to, domain or motif containing fragments, soluble peptide fragments, and fragments containing immunogenic structures. Predicted domains and functional sites are readily identifiable by computer programs well known and readily available to those of skill in the art (e.g., PROSITE, HMMer, eMOTIF, etc.). The results of one such analysis are provided in FIG. 2.

Polypeptides often contain amino acids other than the 20 amino acids commonly referred to as the 20 naturally occurring amino acids. Further, many amino acids, including the terminal amino acids, may be modified by natural processes, such as processing and other post-translational modifications, or by chemical modification techniques well known in the art. Common modifications that occur naturally in Ras-like protein polypeptides are described in basic texts, detailed monographs, and the research literature, and they are well known to those of skill in the art (some of these features are identified in FIG. 2).

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutamate, formulation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as *Proteins—Structure and Molecular Properties*, 2nd Ed., T. E. Creighton, W. H. Freeman and Company, New York (1993). Many detailed reviews are available on this subject, such as by Wold, F., *Posttranslational Covalent Modification of Proteins*, B. C. Johnson, Ed., Academic Press, New York 1–12 (1983); Seifter et al. (*Meth. Enzymol.* 182: 626–646 (1990)) and Rattan et al. (*Ann. N. Y. Acad Sci.* 663:48–62 (1992)).

Accordingly, the Ras-like protein polypeptides of the present invention also encompass derivatives or analogs in which a substituted amino acid residue is not one encoded by the genetic code, in which a substituent group is included, in which the mature Ras-like protein polypeptide is fused with another compound, such as a compound to increase the half-life of the Ras-like protein polypeptide (for example, polyethylene glycol), or in which the additional amino acids are fused to the mature Ras-like protein polypeptide, such as a leader or secretory sequence or a sequence for purification of the mature Ras-like protein polypeptide, or a pro-protein sequence.

Protein/Peptide Uses

The proteins of the present invention can be used in assays to determine the biological activity of the protein, including in a panel of multiple proteins for high-throughput screening; to raise antibodies or to elicit another immune response; as a reagent (including the labeled reagent) in assays designed to quantitatively determine levels of the protein (or its ligand or receptor) in biological fluids; and as markers for tissues in which the corresponding protein is preferentially expressed (either constitutively or at a particular stage of tissue differentiation or development or in a disease state). Where the protein binds or potentially binds to another protein (such as, for example, in a receptor-ligand interaction), the protein can be used to identify the binding partner so as to develop a system to identify inhibitors of the binding interaction. Any or all of these research utilities are capable of being developed into reagent grade or kit format for commercialization as research products.

Methods for performing the uses listed above are well known to those skilled in the art. References disclosing such methods include "Molecular Cloning: A Laboratory Manual", 2d ed., Cold Spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A. R. Kimmel eds., 1987.

The potential uses of the peptides of the present invention are based primarily on the source of the protein as well as the class/action of the protein. For example, Ras-like proteins isolated from humans and their human/mammalian orthologs serve as targets for identifying agents for use in mammalian therapeutic applications, e.g. a human drug, particularly in modulating a biological or pathological response in a cell or tissue that expresses the Ras-like protein. Experimental data as provided in FIG. 1 indicates that Ras-like proteins of the present invention are expressed in humans in fetal brain, adrenal gland, brain neuroblastoma, skin melanotic melanoma, uterus leiomyosarcoma, and placenta, as indicated by virtual northern blot analysis. PCR-based tissue screening panels also indicate expression in the brain. A large percentage of pharmaceutical agents are being developed that modulate the activity of Ras-like proteins, particularly members of the Rab subfamily (see Background of the Invention). The structural and functional information provided in the Background and Figures provide specific and substantial uses for the molecules of the present invention, particularly in combination with the expression information provided in FIG. 1. Experimental data as provided in FIG. 1 indicates expression in the adult and fetal brain, adrenal gland, brain neuroblastoma, skin melanotic melanoma, uterus leiomyosarcoma, and placenta. Such uses can readily be determined using the information provided herein, that which is known in the art, and routine experimentation.

The proteins of the present invention (including variants and fragments that may have been disclosed prior to the present invention) are useful for biological assays related to Ras-like proteins that are related to members of the Rab subfamily. Such assays involve any of the known Ras-like protein functions or activities or properties useful for diagnosis and treatment of Ras-like protein-related conditions that are specific for the subfamily of Ras-like proteins that the one of the present invention belongs to, particularly in cells and tissues that express the Ras-like protein. Experimental data as provided in FIG. 1 indicates that Ras-like proteins of the present invention are expressed in humans in fetal brain, adrenal gland, brain neuroblastoma, skin melanotic melanoma, uterus leiomyosarcoma, and placenta, as indicated by virtual northern blot analysis. PCR-based tissue screening panels also indicate expression in the brain.

The proteins of the present invention are also useful in drug screening assays, in cell-based or cell-free systems. Cell-based systems can be native, i.e., cells that normally express the Ras-like protein, as a biopsy or expanded in cell culture. Experimental data as provided in FIG. 1 indicates expression in the adult and fetal brain, adrenal gland, brain neuroblastoma, skin melanotic melanoma, uterus leiomyosarcoma, and placenta. In an alternate embodiment, cell-based assays involve recombinant host cells expressing the Ras-like protein.

The polypeptides can be used to identify compounds that modulate Ras-like protein activity. Both the Ras-like protein of the present invention and appropriate variants and fragments can be used in high-throughput screens to assay candidate compounds for the ability to bind to the Ras-like protein. These compounds can be further screened against a functional Ras-like protein to determine the effect of the compound on the Ras-like protein activity. Further, these compounds can be tested in animal or invertebrate systems to determine activity/effectiveness. Compounds can be identified that activate (agonist) or inactivate (antagonist) the Ras-like protein to a desired degree.

Therefore, in one embodiment, Rab or a fragment or derivative thereof may be administered to a subject to prevent or treat a disorder associated with an increase in apoptosis. Such disorders include, but are not limited to, AIDS and other infectious or genetic immunodeficiencies, neurodegenerative diseases such as Alzheimer's disease, Parkinson's disease, amyotrophic lateral sclerosis, retinitis pigmentosa, and cerebellar degeneration, myelodysplastic syndromes such as aplastic anemia, ischemic injuries such as myocardial infarction, stroke, and reperfusion injury, toxin-induced diseases such as alcohol-induced liver damage, cirrhosis, and lathyrism, wasting diseases such as cachexia, viral infections such as those caused by hepatitis B and C, and osteoporosis.

In another embodiment, a pharmaceutical composition comprising Rab may be administered to a subject to prevent or treat a disorder associated with increased apoptosis including, but not limited to, those listed above.

In still another embodiment, an agonist which is specific for Rab may be administered to prevent or treat a disorder associated with increased apoptosis including, but not limited to, those listed above.

In a further embodiment, a vector capable of expressing Rab, or a fragment or a derivative thereof, may be used to prevent or treat a disorder associated with increased apoptosis including, but not limited to, those listed above.

In cancer, where Rab promotes cell proliferation, it is desirable to decrease its activity. Therefore, in one embodiment, an antagonist of Rab may be administered to a subject to prevent or treat cancer including, but not limited to, adenocarcinoma, leukemia, lymphoma, melanoma, myeloma, sarcoma, and teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus. In one aspect, an antibody specific for Rab may be used directly as an antagonist, or indirectly as a targeting or delivery mechanism for bringing a pharmaceutical agent to cells or tissue which express Rab.

In another embodiment, a vector expressing the complement of the polynucleotide encoding Rab may be administered to a subject to prevent or treat a cancer including, but not limited to, the types of cancer listed above.

In inflammation, where Rab promotes cell proliferation, it is desirable to decrease its activity. Therefore, in one embodiment, an antagonist of Rab may be administered to a subject to prevent or treat an inflammation. Disorders associated with inflammation include, but are not limited to, Addison's disease, adult respiratory distress syndrome, allergies, anemia, asthma, atherosclerosis, bronchitis, cholecystitis, Crohn's disease, ulcerative colitis, atopic dermatitis, dermatomyositis, diabetes mellitus, emphysema, atrophic gastritis, glomerulonephritis, gout, Graves' disease, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, rheumatoid arthritis, scleroderma, Sjogren's syndrome, and autoimmune thyroiditis; complications of cancer, hemodialysis, extracorporeal circulation; viral, bacterial, fungal, parasitic, protozoal, and helminthic infections and trauma. In one aspect, an antibody specific for Rab may be used directly as an antagonist, or indirectly as a targeting or delivery mechanism for bringing a pharmaceutical agent to cells or tissue which express Rab.

Further, the Ras-like protein polypeptides can be used to screen a compound for the ability to stimulate or inhibit interaction between the Ras-like protein and a molecule that normally interacts with the Ras-like protein, e.g. a ligand or a component of the signal pathway that the Ras-like protein normally interacts. Such assays typically include the steps of combining the Ras-like protein with a candidate compound under conditions that allow the Ras-like protein, or fragment, to interact with the target molecule, and to detect the formation of a complex between the protein and the target or to detect the biochemical consequence of the interaction with the Ras-like protein and the target, such as any of the associated effects of signal transduction.

Candidate compounds include, for example, 1) peptides such as soluble peptides, including Ig-tailed fusion peptides and members of random peptide libraries (see, e.g., Lam et al., Nature 354:82–84 (1991); Houghten et al., Nature 354:84–86 (1991)) and combinatorial chemistry-derived molecular libraries made of D- and/or L-configuration amino acids; 2) phosphopeptides (e.g., members of random and partially degenerate, directed phosphopeptide libraries, see, e.g., Songyang et al., Cell 72:767–778 (1993)); 3) antibodies (e.g., polyclonal, monoclonal, humanized, anti-idiotypic, chimeric, and single chain antibodies as well as Fab, F(ab')$_2$, Fab expression library fragments, and epitope-binding fragments of antibodies); and 4) small organic and inorganic molecules (e.g., molecules obtained from combinatorial and natural product libraries). (Hodgson, Bio/technology, 1992, Sep. 10(9);973–80).

One candidate compound is a soluble fragment of the Ras-like protein that competes for ligand binding. Other candidate compounds include mutant Ras-like proteins or appropriate fragments containing mutations that affect Ras-like protein function and thus compete for ligand. Accordingly, a fragment that competes for ligand, for example with a higher affinity, or a fragment that binds ligand but does not allow release, is within the scope of the invention.

The invention further includes other end point assays to identify compounds that modulate (stimulate or inhibit) Ras-like protein activity. The assays typically involve an assay of events in the Ras-like protein mediated signal transduction pathway that indicate Ras-like protein activity. Thus, the phosphorylation of a protein/ligand target, the expression of genes that are up- or down-regulated in response to the Ras-like protein dependent signal cascade can be assayed. In one embodiment, the regulatory region of such genes can be operably linked to a marker that is easily detectable, such as luciferase. Alternatively, phosphorylation of the Ras-like protein, or a Ras-like protein target, could also be measured.

Any of the biological or biochemical functions mediated by the Ras-like protein can be used as an endpoint assay. These include all of the biochemical or biochemical/biological events described herein, in the references cited herein, incorporated by reference for these endpoint assay targets, and other functions known to those of ordinary skill in the art.

Binding and/or activating compounds can also be screened by using chimeric Ras-like proteins in which any of the protein's domains, or parts thereof, can be replaced by heterologous domains or subregions. Accordingly, a different set of signal transduction components is available as an end-point assay for activation. This allows for assays to be performed in other than the specific host cell from which the Ras-like protein is derived.

The Ras-like protein polypeptide of the present invention is also useful in competition binding assays in methods designed to discover compounds that interact with the Ras-like protein. Thus, a compound is exposed to a Ras-like protein polypeptide under conditions that allow the compound to bind or to otherwise interact with the polypeptide. Soluble Ras-like protein polypeptide is also added to the mixture. If the test compound interacts with the soluble Ras-like protein polypeptide, it decreases the amount of complex formed or activity from the Ras-like protein target. This type of assay is particularly useful in cases in which compounds are sought that interact with specific regions of the Ras-like protein. Thus, the soluble polypeptide that competes with the target Ras-like protein region is designed to contain peptide sequences corresponding to the region of interest.

To perform cell free drug screening assays, it is sometimes desirable to immobilize either the Ras-like protein, or fragment, or its target molecule to facilitate separation of complexes from uncomplexed forms of one or both of the proteins, as well as to accommodate automation of the assay.

Techniques for immobilizing proteins on matrices can be used in the drug screening assays. In one embodiment, a fusion protein can be provided which adds a domain that allows the protein to be bound to a matrix. For example, glutathione-S-transferase/15625 fusion proteins can be adsorbed onto glutathione sepharose beads (Sigma Chemical, St. Louis, Mo.) or glutathione derivatized microtitre plates, which are then combined with the cell lysates (e.g., $^{35}$S-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes are dissociated. Alternatively, the complexes can be dissociated from the matrix, separated by SDS-PAGE, and the level of Ras-like protein-binding protein found in the bead fraction quantitated from the gel using standard electrophoretic techniques. For example, either the polypeptide or its target molecule can be immobilized utilizing conjugation of biotin and streptavidin with techniques well known in the art. Alternatively, antibodies reactive with the protein but which do not interfere with binding of the protein to its target molecule can be derivatized to the wells of the plate, and the protein trapped in the wells by antibody conjugation. Preparations of a Ras-like protein-binding protein and a candidate compound are incubated in the Ras-like protein-presenting wells and the amount of complex trapped in the well can be quantitated. Methods for detecting such complexes, in addition to those described above for the GST-immobilized complexes, include immunodetection of complexes using antibodies reactive with the Ras-like protein target molecule, or which are reactive with Ras-like protein and compete with the target molecule, as well as enzyme-linked assays which rely on detecting an enzymatic activity associated with the target molecule.

Agents that modulate one of the Ras-like proteins of the present invention can be identified using one or more of the above assays, alone or in combination. It is generally preferable to use a cell-based or cell free system first and then confirm activity in an animal/insect model system. Such model systems are well known in the art and can readily be employed in this context.

Modulators of Ras-like protein activity identified according to these drug screening assays can be used to treat a subject with a disorder mediated by the Ras-like protein associated pathway, by treating cells that express the Ras-like protein. Experimental data as provided in FIG. 1 indicates expression in the adult and fetal brain, adrenal gland, brain neuroblastoma, skin melanotic melanoma, uterus leiomyosarcoma, and placenta. These methods of treatment include the steps of administering the modulators of protein activity in a pharmaceutical composition as described herein, to a subject in need of such treatment.

In yet another aspect of the invention, the Ras-like proteins can be used as "bait proteins" in a two-hybrid assay or three-hybrid assay (see, e.g., U.S. Pat. No. 5,283,317; Zervos et al., *Cell* 72:223–232 (1993); Madura et al., *J. Biol. Chem.* 268:12046–12054 (1993); Bartel et al., *Biotechniques* 14:920–924 (1993); Iwabuchi et al., *Oncogene* 8:1693–1696 (1993); and Brent WO94/10300), to identify other proteins that bind to or interact with the Ras-like protein and are involved in Ras-like protein activity. Such Ras-like protein-binding proteins are also likely to be involved in the propagation of signals by the Ras-like proteins or Ras-like protein targets as, for example, downstream elements of a Ras-like protein-mediated signaling pathway, e.g., a pain signaling pathway. Alternatively, such Ras-like protein-binding proteins are likely to be Ras-like protein inhibitors.

The two-hybrid system is based on the modular nature of most transcription factors, which consist of separable DNA-binding and activation domains. Briefly, the assay utilizes two different DNA constructs. In one construct, the gene that codes for a Ras-like protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a Ras-like protein-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the Ras-like protein.

This invention further pertains to novel agents identified by the above-described screening assays. Accordingly, it is within the scope of this invention to further use an agent identified as described herein in an appropriate animal model. For example, an agent identified as described herein (e.g., a Ras-like protein modulating agent, an antisense Ras-like protein nucleic acid molecule, a Ras-like protein-specific antibody, or a Ras-like protein-binding partner) can be used in an animal or insect model to determine the efficacy, toxicity, or side effects of treatment with such an agent. Alternatively, an agent identified as described herein can be used in an animal or insect model to determine the mechanism of action of such an agent. Furthermore, this invention pertains to uses of novel agents identified by the above-described screening assays for treatments as described herein.

The Ras-like proteins of the present invention are also useful to provide a target for diagnosing a disease or predisposition to a disease mediated by the peptide, Accordingly, the invention provides methods for detecting the presence, or levels of, the protein (or encoding mRNA) in a cell, tissue, or organism. Experimental data as provided in FIG. 1 indicates expression in the adult and fetal brain, adrenal gland, brain neuroblastoma, skin melanotic melanoma, uterus leiomyosarcoma, and placenta. The method involves contacting a biological sample with a compound capable of interacting with the receptor protein such that the interaction can be detected. Such an assay can be provided in a single detection format or a multi-detection format such as an antibody chip array.

One agent for detecting a protein in a sample is an antibody capable of selectively binding to protein. A biological sample includes tissues, cells and biological fluids isolated from a subject, as well as tissues, cells, and fluids present within a subject.

The peptides also are useful to provide a target for diagnosing a disease or predisposition to a disease mediated by the peptide, Accordingly, the invention provides methods for detecting the presence, or levels of, the protein in a cell, tissue, or organism. The method involves contacting a biological sample with a compound capable of interacting with the receptor protein such that the interaction can be detected.

The peptides of the present invention also provide targets for diagnosing active disease, or predisposition to a disease, in a patient having a variant peptide. Thus, the peptide can be isolated from a biological sample and assayed for the presence of a genetic mutation that results in translation of an aberrant peptide. This includes amino acid substitution, deletion, insertion, rearrangement, (as the result of aberrant splicing events), and inappropriate post-translational modification. Analytic methods include altered electrophoretic mobility, altered tryptic peptide digest, altered receptor activity in cell-based or cell-free assay, alteration in ligand or antibody-binding pattern, altered isoelectric point, direct amino acid sequencing, and any other of the known assay techniques useful for detecting mutations in a protein. Such an assay can be provided in a single detection format or a multi-detection format such as an antibody chip array.

In vitro techniques for detection of peptide include enzyme linked immunosorbent assays (ELISAs), Western blots, immunoprecipitations, and immunofluorescence using a detection reagents, such as an antibody or protein binding agent. Alternatively, the peptide can be detected in vivo in a subject by introducing into the subject a labeled anti-peptide antibody. For example, the antibody can be labeled with a radioactive marker whose presence and location in a subject can be detected by standard imaging techniques. Particularly useful are methods that detect the allelic variant of a peptide expressed in a subject and methods which detect fragments of a peptide in a sample.

The peptides are also useful in pharmacogenomic analysis. Pharmacogenomics deal with clinically significant hereditary variations in the response to drugs due to altered drug disposition and abnormal action in affected persons. See, e.g., Eichelbaum, M. (*Clin. Exp. Pharmacol. Physiol.* 23(10–11) :983–985 (1996)), and Linder, M. W. (*Clin. Chem.* 43(2):254–266 (1997)). The clinical outcomes of these variations result in severe toxicity of therapeutic drugs in certain individuals or therapeutic failure of drugs in certain individuals as a result of individual variation in metabolism. Thus, the genotype of the individual can determine the way a therapeutic compound acts on the body or the way the body metabolizes the compound. Further, the activity of drug metabolizing enzymes effects both the intensity and duration of drug action. Thus, the pharmacogenomics of the individual permit the selection of effective compounds and effective dosages of such compounds for prophylactic or therapeutic treatment based on the individual's genotype. The discovery of genetic polymorphisms in some drug metabolizing enzymes has explained why some patients do not obtain the expected drug effects, show an exaggerated drug effect, or experience serious toxicity from standard drug dosages. Polymorphisms can be expressed in the phenotype of the extensive metabolizer and the phenotype of the poor metabolizer. Accordingly, genetic polymorphism may lead to allelic protein variants of the receptor protein in which one or more of the receptor functions in one population is different from those in another population. The peptides thus allow a target to ascertain a genetic predisposition that can affect treatment modality. Thus, in a ligand-based treatment, polymorphism may give rise to amino terminal extracellular domains and/or other ligand-binding regions that are more or less active in ligand binding, and receptor activation. Accordingly, ligand dosage would necessarily be modified to maximize the therapeutic effect within a given population containing a polymorphism. As an alternative to genotyping, specific polymorphic peptides could be identified.

The peptides are also useful for treating a disorder characterized by an absence of, inappropriate, or unwanted expression of the protein. Experimental data as provided in FIG. 1 indicates expression in the adult and fetal brain, adrenal gland, brain neuroblastoma, skin melanotic melanoma, uterus leiomyosarcoma, and placenta. Accordingly, methods for treatment include the use of the Ras-like protein or fragments.

Antibodies

The invention also provides antibodies that selectively bind to one of the peptides of the present invention, a protein comprising such a peptide, as well as variants and fragments thereof. As used herein, an antibody selectively binds a target peptide when it binds the target peptide and does not significantly bind to unrelated proteins. An antibody is still considered to selectively bind a peptide even if it also binds to other proteins that are not substantially homologous with the target peptide so long as such proteins share homology with a fragment or domain of the peptide target of the antibody. In this case, it would be understood that antibody binding to the peptide is still selective despite some degree of cross-reactivity.

As used herein, an antibody is defined in terms consistent with that recognized within the art: they are multi-subunit proteins produced by a mammalian organism in response to an antigen challenge. The antibodies of the present invention include polyclonal antibodies and monoclonal antibodies, as well as fragments of such antibodies, including, but not limited to, Fab or F(ab')$_2$, and Fv fragments.

Many methods are known for generating and/or identifying antibodies to a given target peptide. Several such methods are described by Harlow, Antibodies, Cold Spring Harbor Press, (1989).

In general, to generate antibodies, an isolated peptide is used as an immunogen and is administered to a mammalian organism, such as a rat, rabbit or mouse. The full-length protein, an antigenic peptide fragment or a fusion protein can be used. Particularly important fragments are those covering functional domains, such as the domains identified in FIG. 2, and domain of sequence homology or divergence amongst the family, such as those that can readily be identified using protein alignment methods and as presented in the Figures.

Antibodies are preferably prepared from regions or discrete fragments of the Ras-like proteins. Antibodies can be prepared from any region of the peptide as described herein. However, preferred regions will include those involved in function/activity and/or receptor/binding partner interaction. FIG. 2 can be used to identify particularly important regions while sequence alignment can be used to identify conserved and unique sequence fragments.

An antigenic fragment will typically comprise at least 8 contiguous amino acid residues. The antigenic peptide can comprise, however, at least 10, 12, 14, 16 or more amino acid residues. Such fragments can be selected on a physical property, such as fragments correspond to regions that are located on the surface of the protein, e.g., hydrophilic regions or can be selected based on sequence uniqueness (see FIG. 2).

Detection of an antibody of the present invention can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include urnbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$, or $^{3}H$.

Antibody Uses

The antibodies can be used to isolate one of the proteins of the present invention by standard techniques, such as affinity chromatography or immunoprecipitation. The antibodies can facilitate the purification of the natural protein from cells and recombinantly produced protein expressed in host cells. In addition, such antibodies are useful to detect the presence of one of the proteins of the present invention in cells or tissues to determine the pattern of expression of the protein among various tissues in an organism and over the course of normal development. Experimental data as provided in FIG. 1 indicates that Ras-like proteins of the present invention are expressed in humans in fetal brain, adrenal gland, brain neuroblastoma, skin melanotic melanoma, uterus leiomyosarcoma, and placenta, as indicated by virtual northern blot analysis. PCR-based tissue screening panels also indicate expression in the brain. Further, such antibodies can be used to detect protein in situ, in vitro, or in a cell lysate or supernatant in order to evaluate the abundance and pattern of expression. Also, such antibodies can be used to assess abnormal tissue distribution or abnormal expression during development. Antibody detection of circulating fragments of the full-length protein can be used to identify turnover.

Further, the antibodies can be used to assess expression in disease states such as in active stages of the disease or in an individual with a predisposition toward disease related to the protein's function. When a disorder is caused by an inappropriate tissue distribution, developmental expression, level of expression of the protein, or expressed/processed form, the antibody can be prepared against the normal protein. Experimental data as provided in FIG. 1 indicates expression in the adult and fetal brain, adrenal gland, brain neuroblastoma, skin melanotic melanoma, uterus leiomyosarcoma, and placenta. If a disorder is characterized by a specific mutation in the protein, antibodies specific for this mutant protein can be used to assay for the presence of the specific mutant protein.

The antibodies can also be used to assess normal and aberrant subcellular localization of cells in the various tissues in an organism. Experimental data as provided in FIG. 1 indicates expression in the adult and fetal brain, adrenal gland, brain neuroblastoma, skin melanotic melanoma, uterus leiomyosarcoma, and placenta. The diagnostic uses can be applied, not only in genetic testing, but also in monitoring a treatment modality. Accordingly, where treatment is ultimately aimed at correcting expression level or the presence of aberrant sequence and aberrant tissue distribution or developmental expression, antibodies directed against the or relevant fragments can be used to monitor therapeutic efficacy.

Additionally, antibodies are useful in pharmacogenomic analysis. Thus, antibodies prepared against polymorphic proteins can be used to identify individuals that require modified treatment modalities. The antibodies are also useful as diagnostic tools as an immunological marker for aberrant protein analyzed by electrophoretic mobility, isoelectric point, tryptic peptide digest, and other physical assays known to those in the art.

The antibodies are also useful for tissue typing. Experimental data as provided in FIG. 1 indicates expression in the adult and fetal brain, adrenal gland, brain neuroblastoma, skin melanotic melanoma, uterus leiomyosarcoma, and placenta. Thus, where a specific protein has been correlated with expression in a specific tissue, antibodies that are specific for this protein can be used to identify a tissue type.

The antibodies are also useful for inhibiting protein function, for example, blocking the binding of the Ras-like protein to a binding partner such as a substrate. These uses can also be applied in a therapeutic context in which treatment involves inhibiting the protein's function. An antibody can be used, for example, to block binding, thus modulating (agonizing or antagonizing) the peptides activity. Antibodies can be prepared against specific fragments containing sites required for function or against intact protein that is associated with a cell or cell membrane. See FIG. 2 for structural information relating to the proteins of the present invention.

The invention also encompasses kits for using antibodies to detect the presence of a protein in a biological sample. The kit can comprise antibodies such as a labeled or labelable antibody and a compound or agent for detecting protein in a biological sample; means for determining the amount of protein in the sample; means for comparing the amount of protein in the sample with a standard; and instructions for use.

Nucleic Acid Molecules

The present invention further provides isolated nucleic acid molecules that encode a Ras-like protein polypeptide of the present invention. Such nucleic acid molecules will consist of, consist essentially of, or comprise a nucleotide sequence that encodes one of the Ras-like protein polypeptides of the present invention, an allelic variant thereof, or an ortholog or paralog thereof.

As used herein, an "isolated" nucleic acid molecule is one that is separated from other nucleic acid present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. However, there can be some flanking nucleotide sequences, for example up to about 5KB, particularly contiguous peptide encoding sequences and peptide encoding sequences within the same gene but separated by introns in the genomic sequence. The important point is that the nucleic acid is isolated from remote and unimportant flanking sequences such that it can be subjected to the specific manipulations described herein such as recombinant expression, preparation of probes and primers, and other uses specific to the nucleic acid sequences.

Moreover, an "isolated" nucleic acid molecule, such as a cDNA molecule, can be substantially free of other cellular material, or culture medium when produced by recombinant techniques, or chemical precursors or other chemicals when chemically synthesized. However, the nucleic acid molecule can be fused to other coding or regulatory sequences and still be considered isolated.

For example, recombinant DNA molecules contained in a vector are considered isolated. Further examples of isolated DNA molecules include recombinant DNA molecules maintained in heterologous host cells or purified (partially or substantially) DNA molecules in solution. Isolated RNA molecules include in vivo or in vitro RNA transcripts of the isolated DNA molecules of the present invention. Isolated nucleic acid molecules according to the present invention further include such molecules produced synthetically.

Accordingly, the present invention provides nucleic acid molecules that consist of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists of a nucleotide sequence when the nucleotide sequence is the complete nucleotide sequence of the nucleic acid molecule. The present invention further provides nucleic acid molecules that consist essentially of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists essentially of a nucleotide sequence when such a nucleotide sequence is present with only a few additional nucleic acid residues in the final nucleic acid molecule.

The present invention further provides nucleic acid molecules that comprise the nucleotide sequences shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule comprises a nucleotide sequence when the nucleotide sequence is at least part of the final nucleotide sequence of the nucleic acid molecule. In such a fashion, the nucleic acid molecule can be only the nucleotide sequence or have additional nucleic acid residues, such as nucleic acid residues that are naturally associated with it or heterologous nucleotide sequences. Such a nucleic acid molecule can have a few additional nucleotides or can comprises several hundred or more additional nucleotides. A brief description of how various types of these nucleic acid molecules can be readily made/isolated is provided below.

In FIGS. 1 and 3, both coding and non-coding sequences are provided. Because of the source of the present invention, humans genomic sequence (FIG. 3) and cDNA/transcript sequences (FIG. 1), the nucleic acid molecules in the Figures will contain genomic intronic sequences, 5' and 3' non-coding sequences, gene regulatory regions and non-coding intergenic sequences. In general such sequence features are either noted in FIGS. 1 and 3 or can readily be identified using computational tools known in the art. As discussed below, some of the non-coding regions, particularly gene regulatory elements such as promoters, are useful for a variety of purposes, e.g. control of heterologous gene expression, target for identifying gene activity modulating compounds, and are particularly claimed as fragments of the genomic sequence provided herein.

Full-length genes may be cloned from known sequence using any one of a number of methods known in the art. For example, a method which employs XL-PCR (Perkin-Elmer, Foster City, Calif.) to amplify long pieces of DNA may be used. Other methods for obtaining full-length sequences are well known in the art.

The isolated nucleic acid molecules can encode the mature protein plus additional amino or carboxyl-terminal amino acids, or amino acids interior to the mature peptide (when the mature form has more than one peptide chain, for instance). Such sequences may play a role in processing of a protein from precursor to a mature form, facilitate protein trafficking, prolong or shorten protein half-life, or facilitate manipulation of a protein for assay or production, among other things. As generally is the case in situ, the additional amino acids may be processed away from the mature protein by cellular enzymes.

As mentioned above, the isolated nucleic acid molecules include, but are not limited to, the sequence encoding the Ras-like protein polypeptide alone, the sequence encoding the mature peptide and additional coding sequences, such as a leader or secretory sequence (e.g., a pre-pro or pro-protein sequence), the sequence encoding the mature peptide, with or without the additional coding sequences, plus additional non-coding sequences, for example introns and non-coding 5' and 3' sequences such as transcribed but non-translated sequences that play a role in transcription, mRNA processing (including splicing and polyadenylation signals), ribosome binding, and stability of mRNA. In addition, the nucleic acid molecule may be fused to a marker sequence encoding, for example, a peptide that facilitates purification.

Isolated nucleic acid molecules can be in the form of RNA, such as mRNA, or in the form of DNA, including cDNA and genomic DNA obtained by cloning or produced by chemical synthetic techniques or by a combination thereof. The nucleic acid, especially DNA, can be double-stranded or single-stranded. Single-stranded nucleic acid can be the coding strand (sense strand) or the non-coding strand (anti-sense strand).

The invention further provides nucleic acid molecules that encode fragments of the peptides of the present invention and that encode obvious variants of the Ras-like proteins of the present invention that are described above. Such nucleic acid molecules may be naturally occurring, such as allelic variants (same locus), paralogs (different locus), and orthologs (different organism), or may be constructed by recombinant DNA methods or by chemical synthesis. Such non-naturally occurring variants may be made by mutagenesis techniques, including those applied to nucleic acid molecules, cells, or whole organisms. Accordingly, as discussed above, the variants can contain nucleotide substitutions, deletions inversions, and/or insertions. Variation can occur in either or both the coding and non-coding regions. The variations can produce both conservative and non-conservative amino acid substitutions.

The present invention further provides non-coding fragments of the nucleic acid molecules provided in the FIGS. 1 and 3. Preferred non-coding fragments include, but are not limited to, promoter sequences, enhancer sequences, gene modulating sequences, and gene termination sequences. Such fragments are useful in controlling heterologous gene expression and in developing screens to identify gene-modulating agents.

A fragment comprises a contiguous nucleotide sequence greater than 12 or more nucleotides. Further, a fragment could be at least 30, 40, 50, 100 250, or 500 nucleotides in length. The length of the fragment will be based on its intended use. For example, the fragment can encode epitope-bearing regions of the peptide, or can be useful as DNA probes and primers. Such fragments can be isolated using the known nucleotide sequence to synthesize an oligonucleotide probe. A labeled probe can then be used to screen a cDNA library, genomic DNA library, or mRNA to isolate nucleic acid corresponding to the coding region. Further, primers can be used in PCR reactions to clone specific regions of gene.

A probe/primer typically comprises substantially a purified oligonucleotide or oligonucleotide pair. The oligonucleotide typically comprises a region of nucleotide sequence that hybridizes under stringent conditions to at least about 12, 20, 25, 40, 50, or more consecutive nucleotides.

Orthologs, homologs, and allelic variants can be identified using methods well known in the art. As described in the Peptide Section, these variants comprise a nucleotide sequence encoding a peptide that is typically 60–70%, 70–80%, 80–90%, and more typically at least about 90–95% or more homologous to the nucleotide sequence shown in the Figure sheets or a fragment of this sequence. Such nucleic acid molecules can readily be identified as being able to hybridize under moderate to stringent conditions, to the nucleotide sequence shown in the Figure sheets or a fragment of the sequence. The gene encoding the novel Ras-like protein of the present invention is located on a genome component that has been mapped to human chromosome 2 (as indicated in FIG. 3), which is supported by multiple lines of evidence, such as STS and BAC map data.

FIG. 3 provides information on SNPs that have been found in the gene encoding the Ras-like protein of the present invention. SNPs were identified at 25 different nucleotide positions. Some of these SNPs that are located outside the ORF and in introns may affect gene transcription.

As used herein, the term "hybridizes under stringent conditions" is intended to describe conditions for hybridization and washing under which nucleotide sequences encoding a peptide at least 60–70% homologous to each other typically remain hybridized to each other. The conditions can be such that sequences at least about 60%, at least about 70%, or at least about 80% or more homologous to each other typically remain hybridized to each other. Such stringent conditions are known to those skilled in the art and can be found in *Current Protocols in Molecular Biology*, John Wiley & Sons, N.Y. (1989), 6.3.1–6.3.6. One example of stringent hybridization conditions are hybridization in 6× sodium chloride/sodium citrate (SSC) at about 45 C., followed by one or more washes in 0.2×SSC, 0.1% SDS at 50–65° C. Examples of moderate to low stringency hybridization conditions are well known in the art.

Nucleic Acid Molecule Uses

The nucleic acid molecules of the present invention are useful for probes, primers, chemical intermediates, and in biological assays. The nucleic acid molecules are useful as a hybridization probe for messenger RNA, transcript/cDNA and genomic DNA to isolate full-length cDNA and genomic clones encoding the peptide described in FIG. 2 and to isolate cDNA and genomic clones that correspond to variants (alleles, orthologs, etc.) producing the same or related peptides shown in FIG. 2. As illustrated in FIG. 3, SNPs were identified at 25 different nucleotide positions.

The probe can correspond to any sequence along the entire length of the nucleic acid molecules provided in the Figures. Accordingly, it could be derived from 5' noncoding regions, the coding region, and 3' noncoding regions. However, as discussed, fragments are not to be construed as those, which may encompass fragments disclosed prior to the present invention.

The nucleic acid molecules are also useful as primers for PCR to amplify any given region of a nucleic acid molecule and are useful to synthesize antisense molecules of desired length and sequence.

The nucleic acid molecules are also useful for constructing recombinant vectors. Such vectors include expression vectors that express a portion of, or all of, the peptide sequences. Vectors also include insertion vectors, used to integrate into another nucleic acid molecule sequence, such as into the cellular genome, to alter in situ expression of a gene and/or gene product. For example, an endogenous coding sequence can be replaced via homologous recombination with all or part of the coding region containing one or more specifically introduced mutations.

The nucleic acid molecules are also useful for expressing antigenic portions of the proteins.

The nucleic acid molecules are also useful as probes for determining the chromosomal positions of the nucleic acid molecules by means of in situ hybridization methods. The gene encoding the novel Ras-like protein of the present invention is located on a genome component that has been mapped to human chromosome 2 (as indicated in FIG. 3), which is supported by multiple lines of evidence, such as STS and BAC map data.

The nucleic acid molecules are also useful in making vectors containing the gene regulatory regions of the nucleic acid molecules of the present invention.

The nucleic acid molecules are also useful for designing ribozymes corresponding to all, or a part, of the mRNA produced from the nucleic acid molecules described herein.

The nucleic acid molecules are also useful for constructing host cells expressing a part, or all, of the nucleic acid molecules and peptides. Moreover, the nucleic acid molecules are useful for constructing transgenic animals wherein a homolog of the nucleic acid molecule has been "knocked-out" of the animal's genome.

The nucleic acid molecules are also useful for constructing transgenic animals expressing all, or a part, of the nucleic acid molecules and peptides.

The nucleic acid molecules are also useful for making vectors that express part, or all, of the peptides.

The nucleic acid molecules are also useful as hybridization probes for determining the presence, level, form, and distribution of nucleic acid expression. Experimental data as provided in FIG. 1 indicates that Ras-like proteins of the present invention are expressed in humans in fetal brain, adrenal gland, brain neuroblastoma, skin melanotic melanoma, uterus leiomyosarcoma, and placenta, as indicated by virtual northern blot analysis. PCR-based tissue screening panels also indicate expression in the brain. Accordingly, the probes can be used to detect the presence of, or to determine levels of, a specific nucleic acid molecule in cells, tissues, and in organisms. The nucleic acid whose level is determined can be DNA or RNA. Accordingly, probes corresponding to the peptides described herein can be used to assess expression and/or gene copy number in a given cell, tissue, or organism. These uses are relevant for diagnosis of disorders involving an increase or decrease in Ras-like protein expression relative to normal results.

In vitro techniques for detection of mRNA include Northern hybridizations and in situ hybridizations. In vitro techniques for detecting DNA include Southern hybridizations and in situ hybridization.

Probes can be used as a part of a diagnostic test kit for identifying cells or tissues that express a Ras-like protein, such as by measuring a level of a receptor-encoding nucleic acid in a sample of cells from a subject e.g., mRNA or genomic DNA, or determining if a receptor gene has been mutated. Experimental data as provided in FIG. 1 indicates that Ras-like proteins of the present invention are expressed in humans in fetal brain, adrenal gland, brain neuroblastoma, skin melanotic melanoma, uterus leiomyosarcoma, and placenta, as indicated by virtual northern blot analysis. PCR-based tissue screening panels also indicate expression in the brain.

Nucleic acid expression assays are useful for drug screening to identify compounds that modulate Ras-like protein nucleic acid expression.

The invention thus provides a method for identifying a compound that can be used to treat a disorder associated with nucleic acid expression of the Ras-like protein gene, particularly biological and pathological processes that are mediated by the Ras-like protein in cells and tissues that express it. Experimental data as provided in FIG. 1 indicates expression in the adult and fetal brain, adrenal gland, brain neuroblastoma, skin melanotic melanoma, uterus leiomyosarcoma, and placenta. The method typically includes assaying the ability of the compound to modulate the expression of the Ras-like protein nucleic acid and thus identifying a compound that can be used to treat a disorder characterized by undesired Ras-like protein nucleic acid expression. The assays can be performed in cell-based and cell-free systems. Cell-based assays include cells naturally expressing the Ras-like protein nucleic acid or recombinant cells genetically engineered to express specific nucleic acid sequences.

The assay for Ras-like protein nucleic acid expression can involve direct assay of nucleic acid levels, such as mRNA levels, or on collateral compounds involved in the signal pathway. Further, the expression of genes that are up- or down-regulated in response to the Ras-like protein signal pathway can also be assayed. In this embodiment the regulatory regions of these genes can be operably linked to a reporter gene such as luciferase.

Thus, modulators of Ras-like protein gene expression can be identified in a method wherein a cell is contacted with a candidate compound and the expression of mRNA determined. The level of expression of Ras-like protein mRNA in the presence of the candidate compound is compared to the level of expression of Ras-like protein mRNA in the absence of the candidate compound. The candidate compound can then be identified as a modulator of nucleic acid expression based on this comparison and be used, for example to treat a disorder characterized by aberrant nucleic acid expression. When expression of mRNA is statistically significantly greater in the presence of the candidate compound than in its absence, the candidate compound is identified as a stimulator of nucleic acid expression. When nucleic acid expression is statistically significantly less in the presence of the candidate compound than in its absence, the candidate compound is identified as an inhibitor of nucleic acid expression.

The invention further provides methods of treatment, with the nucleic acid as a target, using a compound identified through drug screening as a gene modulator to modulate Ras-like protein nucleic acid expression in cells and tissues that express the Ras-like protein. Experimental data as provided in FIG. 1 indicates that Ras-like proteins of the present invention are expressed in humans in fetal brain, adrenal gland, brain neuroblastoma, skin melanotic melanoma, uterus leiomyosarcoma, and placenta, as indicated by virtual northern blot analysis. PCR-based tissue screening panels also indicate expression in the brain. Modulation includes both up-regulation (i.e. activation or agonization) or down-regulation (suppression or antagonization) of nucleic acid expression.

Alternatively, a modulator for Ras-like protein nucleic acid expression can be a small molecule or drug identified using the screening assays described herein as long as the drug or small molecule inhibits the Ras-like protein nucleic acid expression in the cells and tissues that express the protein. Experimental data as provided in FIG. 1 indicates expression in the adult and fetal brain, adrenal gland, brain neuroblastoma, skin melanotic melanoma, uterus leiomyosarcoma, and placenta.

The nucleic acid molecules are also useful for monitoring the effectiveness of modulating compounds on the expression or activity of the Ras-like protein gene in clinical trials or in a treatment regimen. Thus, the gene expression pattern can serve as a barometer for the continuing effectiveness of treatment with the compound, particularly with compounds to which a patient can develop resistance. The gene expression pattern can also serve as a marker indicative of a physiological response of the affected cells to the compound. Accordingly, such monitoring would allow either increased administration of the compound or the administration of alternative compounds to which the patient has not become resistant. Similarly, if the level of nucleic acid expression falls below a desirable level, administration of the compound could be commensurately decreased.

The nucleic acid molecules are also useful in diagnostic assays for qualitative changes in Ras-like protein nucleic acid, and particularly in qualitative changes that lead to pathology. The nucleic acid molecules can be used to detect mutations in Ras-like protein genes and gene expression products such as mRNA. The nucleic acid molecules can be used as hybridization probes to detect naturally occurring genetic mutations in the Ras-like protein gene and thereby to determine whether a subject with the mutation is at risk for a disorder caused by the mutation. Mutations include deletion, addition, or substitution of one or more nucleotides in the gene, chromosomal rearrangement, such as inversion or transposition, modification of genomic DNA, such as aberrant methylation patterns, or changes in gene copy number, such as amplification. Detection of a mutated form of the Ras-like protein gene associated with a dysfunction provides a diagnostic tool for an active disease or susceptibility to disease when the disease results from overexpression, underexpression, or altered expression of a Ras-like protein.

Individuals carrying mutations in the Ras-like protein gene can be detected at the nucleic acid level by a variety of techniques. FIG. 3 provides information on SNPs that have been found in the gene encoding the Ras-like protein of the present invention. SNPs were identified at 25 different nucleotide positions. Some of these SNPs that are located outside the ORF and in introns may affect gene transcription. The gene encoding the novel Ras-like protein of the present invention is located on a genome component that has been mapped to human chromosome 2 (as indicated in FIG. 3), which is supported by multiple lines of evidence, such as STS and BAC map data. Genomic DNA can be analyzed directly or can be amplified by using PCR prior to analysis. RNA or cDNA can be used in the same way. In some uses, detection of the mutation involves the use of a probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al., Science 241:1077–1080 (1988); and Nakazawa et al., PNAS 91 :360–364 (1994)), the latter of which can be particularly useful for detecting point mutations in the gene (see Abravaya et al., Nucleic Acids Res. 23:675–682 (1995)). This method can include the steps of collecting a sample of cells from a patient, isolating nucleic acid (e.g., genomic, mRNA or both) from the cells of the sample, contacting the nucleic acid sample with one or more primers which specifically hybridize to a gene under conditions such that hybridization and amplification of the gene (if present) occurs, and detecting the presence or absence of an amplification product, or detecting the size of the amplification product and comparing the length to a control sample. Deletions and insertions can be detected by a change in size of the amplified product compared to the normal genotype. Point mutations can be identified by hybridizing amplified DNA to normal RNA or antisense DNA sequences.

Alternatively, mutations in a Ras-like protein gene can be directly identified, for example, by alterations in restriction enzyme digestion patterns determined by gel electrophoresis.

Further, sequence-specific ribozymes (U.S. Pat. No. 5,498,531) can be used to score for the presence of specific mutations by development or loss of a ribozyme cleavage site. Perfectly matched sequences can be distinguished from mismatched sequences by nuclease cleavage digestion assays or by differences in melting temperature.

Sequence changes at specific locations can also be assessed by nuclease protection assays such as RNase and S1 protection or the chemical cleavage method. Furthermore, sequence differences between a mutant Ras-like protein gene and a wild-type gene can be determined by direct DNA sequencing. A variety of automated sequencing procedures can be utilized when performing the diagnostic assays (Naeve, C. W., Biotechniques 19:448 (1995)), including sequencing by mass spectrometry (see, e.g., PCT International Publication No. WO 94/16101; Cohen et al., Adv. Chromatogr. 36:127–162 (1996); and Griffin et al., Appl. Biochem. Biotechnol. 38:147–159 (1993)).

Other methods for detecting mutations in the gene include methods in which protection from cleavage agents is used to detect mismatched bases in RNA/RNA or RNA/DNA duplexes (Myers et al., Science 230:1242 (1985)); Cotton et al., PNAS 85:4397 (1988); Saleeba et al., Meth. Enzymol. 217:286–295 (1992)), electrophoretic mobility of mutant and wild type nucleic acid is compared (Orita et al., PNAS 86:2766 (1989); Cotton et al., Mutat. Res. 285:125–144 (1993); and Hayashi et al., Genet. Anal. Tech. Appl. 9:73–79 (1992)), and movement of mutant or wild-type fragments in polyacrylamide gels containing a gradient of denaturant is assayed using denaturing gradient gel electrophoresis (Myers et al., Nature 313:495 (1985)). Examples of other techniques for detecting point mutations include, selective oligonucleotide hybridization, selective amplification, and selective primer extension.

The nucleic acid molecules are also useful for testing an individual for a genotype that while not necessarily causing the disease, nevertheless affects the treatment modality. Thus, the nucleic acid molecules can be used to study the relationship between an individual's genotype and the individual's response to a compound used for treatment (pharmacogenomic relationship). Accordingly, the nucleic acid molecules described herein can be used to assess the mutation content of the Ras-like protein gene in an individual in order to select an appropriate compound or dosage regimen for treatment. FIG. 3 provides information on SNPs that have been found in the gene encoding the Ras-like protein of the present invention. SNPs were identified at 25 different nucleotide positions. Some of these SNPs that are located outside the ORF and in introns may affect gene transcription.

Thus nucleic acid molecules displaying genetic variations that affect treatment provide a diagnostic target that can be used to tailor treatment in an individual. Accordingly, the production of recombinant cells and animals containing these polymorphisms allow effective clinical design of treatment compounds and dosage regimens.

The nucleic acid molecules are thus useful as antisense constructs to control Ras-like protein gene expression in cells, tissues, and organisms. A DNA antisense nucleic acid molecule is designed to be complementary to a region of the gene involved in transcription, preventing transcription and hence production of Ras-like protein. An antisense RNA or DNA nucleic acid molecule would hybridize to the mRNA and thus block translation of mRNA into Ras-like protein.

Alternatively, a class of antisense molecules can be used to inactivate mRNA in order to decrease expression of Ras-like protein nucleic acid. Accordingly, these molecules can treat a disorder characterized by abnormal or undesired Ras-like protein nucleic acid expression. This technique involves cleavage by means of ribozymes containing nucleotide sequences complementary to one or more regions in the mRNA that attenuate the ability of the mRNA to be translated. Possible regions include coding regions and particularly coding regions corresponding to the catalytic and other functional activities of the Ras-like protein, such as ligand binding.

The nucleic acid molecules also provide vectors for gene therapy in patients containing cells that are aberrant in Ras-like protein gene expression. Thus, recombinant cells, which include the patient's cells that have been engineered ex vivo and returned to the patient, are introduced into an individual where the cells produce the desired Ras-like protein to treat the individual.

The invention also encompasses kits for detecting the presence of a Ras-like protein nucleic acid in a biological sample. Experimental data as provided in FIG. 1 indicates that Ras-like proteins of the present invention are expressed in humans in fetal brain, adrenal gland, brain neuroblastoma, skin melanotic melanoma, uterus leiomyosarcoma, and placenta, as indicated by virtual northern blot analysis. PCR-based tissue screening panels also indicate expression in the brain. For example, the kit can comprise reagents such as a labeled or labelable nucleic acid or agent capable of detecting Ras-like protein nucleic acid in a biological sample; means for determining the amount of Ras-like protein nucleic acid in the sample; and means for comparing the amount of Ras-like protein nucleic acid in the sample with a standard. The compound or agent can be packaged in a suitable container. The kit can further comprise instructions for using the kit to detect Ras-like protein mRNA or DNA.

Nucleic Acid Arrays

The present invention further provides arrays or microarrays of nucleic acid molecules that are based on the sequence information provided in FIGS. 1 and 3 (SEQ ID NOS:1 and 3).

As used herein "Arrays" or "Microarrays" refers to an array of distinct polynucleotides or oligonucleotides synthesized on a substrate, such as paper, nylon or other type of membrane, filter, chip, glass slide, or any other suitable solid support. In one embodiment, the microarray is prepared and used according to the methods described in U.S. Pat. No. 5,837,832, Chee et al., PCT application WO95/11995 (Chee et al.), Lockhart, D. J. et al. (1996; Nat. Biotech. 14: 1675–1680) and Schena, M. et al. (1996; Proc. Natl. Acad. Sci. 93: 10614–10619), all of which are incorporated herein in their entirety by reference. In other embodiments, such arrays are produced by the methods described by Brown et. al., U.S. Pat. No. 5,807,522.

The microarray is preferably composed of a large number of unique, single-stranded nucleic acid sequences, usually either synthetic antisense oligonucleotides or fragments of cDNAs, fixed to a solid support. The oligonucleotides are preferably about 6–60 nucleotides in length, more preferably 15–30 nucleotides in length, and most preferably about 20–25 nucleotides in length. For a certain type of microarray, it may be preferable to use oligonucleotides that are only 7–20 nucleotides in length. The microarray may contain oligonucleotides that cover the known 5', or 3', sequence, sequential oligonucleotides that cover the full-length sequence; or unique oligonucleotides selected from particular areas along the length of the sequence. Polynucleotides used in the microarray may be oligonucleotides that are specific to a gene or genes of interest.

In order to produce oligonucleotides to a known sequence for a microarray, the gene(s) of interest (or an ORF identified from the contigs of the present invention) is typically examined using a computer algorithm that starts at the 5' or at the 3' end of the nucleotide sequence. Typical algorithms will then identify oligomers of defined length that are unique to the gene, have a GC content within a range suitable for hybridization, and lack predicted secondary structure that may interfere with hybridization. In certain situations it may be appropriate to use pairs of oligonucleotides on a microarray. The "pairs" will be identical, except for one nucleotide that preferably is located in the center of the sequence. The second oligonucleotide in the pair (mismatched by one) serves as a control. The number of oligonucleotide pairs may range from two to one million. The oligomers are synthesized at designated areas on a substrate using a light-directed chemical process. The substrate may be paper, nylon or other type of membrane, filter, chip, glass slide or any other suitable solid support.

In another aspect, an oligonucleotide may be synthesized on the surface of the substrate by using a chemical coupling procedure and an ink jet application apparatus, as described in PCT application WO95/251116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536, 6144 or more oligonucleotides, or any other number between two and one million which lends itself to the efficient use of commercially available instrumentation.

In order to conduct sample analysis using a microarray, the RNA or DNA from a biological sample is made into hybridization probes. The mRNA is isolated, and cDNA is produced and used as a template to make antisense RNA (aRNA). The aRNA is amplified in the presence of fluorescent nucleotides, and labeled probes are incubated with the microarray so that the probe sequences hybridize to complementary oligonucleotides of the microarray. Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray. The biological samples may be obtained from any bodily fluids (such as blood, urine, saliva, phlegm, gastric juices, etc.), cultured cells, biopsies, or other tissue preparations. A detection system may be used to measure the absence, presence, and amount of hybridization for all of the distinct sequences simultaneously. This data may be used for large-scale correlation studies on the sequences, expression patterns, mutations, variants, or polymorphisms among samples.

Using such arrays, the present invention provides methods to identify the expression of one or more of the proteins/peptides of the present invention. In detail, such methods comprise incubating a test sample with one or more nucleic acid molecules and assaying for binding of the nucleic acid molecule with components within the test sample. Such assays will typically involve arrays comprising many genes, at least one of which is a gene of the present invention. FIG. 3 provides information on SNPs that have been found in the gene encoding the Ras-like protein of the present invention. SNPs were identified at 25 different nucleotide positions. Some of these SNPs that are located outside the ORF and in introns may affect gene transcription.

Conditions for incubating a nucleic acid molecule with a test sample vary. Incubation conditions depend on the format employed in the assay, the detection methods employed, and the type and nature of the nucleic acid molecule used in the assay. One skilled in the art will recognize that any one of the commonly available hybridization, amplification or array assay formats can readily be adapted to employ the novel fragments of the human genome disclosed herein. Examples of such assays can be found in Chard, T, *An Introduction to Radioimmunoassay and Related Techniques,* Elsevier Science Publishers, Amsterdam, The Netherlands (1986); Bullock, G. R. et al., *Techniques in Immunocytochemistry,* Academic Press, Orlando, Fla. Vol. 1 (1982), Vol. 2 (1983), Vol. 3 (1985); Tijssen, P., *Practice and Theory of Enzyme Immunoassays: Laboratory Techniques in Biochemistry and Molecular Biology,* Elsevier Science Publishers, Amsterdam, The Netherlands (1985).

The test samples of the present invention include cells, protein or membrane extracts of cells. The test sample used in the above-described method will vary based on the assay format, nature of the detection method and the tissues, cells or extracts used as the sample to be assayed. Methods for preparing nucleic acid extracts or of cells are well known in the art and can be readily be adapted in order to obtain a sample that is compatible with the system utilized.

In another embodiment of the present invention, kits are provided which contain the necessary reagents to carry out the assays of the present invention.

Specifically, the invention provides a compartmentalized kit to receive, in close confinement, one or more containers which comprises: (a) a first container comprising one of the nucleic acid molecules that can bind to a fragment of the human genome disclosed herein; and (b) one or more other containers comprising one or more of the following: wash reagents, reagents capable of detecting presence of a bound nucleic acid. Preferred kits will include chips that are capable of detecting the expression of 10 or more, 100 or more, or 500 or more, 1000 or more, or all of the genes expressed in Human.

In detail, a compartmentalized kit includes any kit in which reagents are contained in separate containers. Such containers include small glass containers, plastic containers, strips of plastic, glass or paper, or arraying material such as silica. Such containers allows one to efficiently transfer reagents from one compartment to another compartment such that the samples and reagents are not cross-contaminated, and the agents or solutions of each container can be added in a quantitative fashion from one compartment to another. Such containers will include a container which will accept the test sample, a container which contains the nucleic acid probe, containers which contain wash reagents (such as phosphate buffered saline, Tris-buffers, etc.), and containers which contain the reagents used to detect the bound probe. One skilled in the art will readily recognize that the previously unidentified Ras-like protein genes of the present invention can be routinely identified using the sequence information disclosed herein can be readily incorporated into one of the established kit formats which are well known in the art, particularly expression arrays.

Vectors/Host Cells

The invention also provides vectors containing the nucleic acid molecules described herein. The term "vector" refers to a vehicle, preferably a nucleic acid molecule, which can transport the nucleic acid molecules. When the vector is a nucleic acid molecule, the nucleic acid molecules are covalently linked to the vector nucleic acid. With this aspect of the invention, the vector includes a plasmid, single or double stranded phage, a single or double stranded RNA or DNA viral vector, or artificial chromosome, such as a BAC, PAC, YAC, OR MAC.

A vector can be maintained in the host cell as an extra-chromosomal element where it replicates and produces additional copies of the nucleic acid molecules. Alternatively, the vector may integrate into the host cell genome and produce additional copies of the nucleic acid molecules when the host cell replicates.

The invention provides vectors for the maintenance (cloning vectors) or vectors for expression (expression vectors) of the nucleic acid molecules. The vectors can function in procaryotic or eukaryotic cells or in both (shuttle vectors).

Expression vectors contain cis-acting regulatory regions that are operably linked in the vector to the nucleic acid molecules such that transcription of the nucleic acid molecules is allowed in a host cell. The nucleic acid molecules can be introduced into the host cell with a separate nucleic acid molecule capable of affecting transcription. Thus, the second nucleic acid molecule may provide a trans-acting factor interacting with the cis-regulatory control region to allow transcription of the nucleic acid molecules from the vector. Alternatively, a trans-acting factor may be supplied by the host cell. Finally, a trans-acting factor can be produced from the vector itself. It is understood, however, that in some embodiments, transcription and/or translation of the nucleic acid molecules can occur in a cell-free system.

The regulatory sequence to which the nucleic acid molecules described herein can be operably linked include promoters for directing mRNA transcription. These include, but are not limited to, the left promoter from bacteriophage λ, the lac, TRP, and TAC promoters from *E. coli,* the early and late promoters from SV40, the CMV immediate early promoter, the adenovirus early and late promoters, and retrovirus long-terminal repeats.

In addition to control regions that promote transcription, expression vectors may also include regions that modulate transcription, such as repressor binding sites and enhancers. Examples include the SV40 enhancer, the cytomegalovirus immediate early enhancer, polyoma enhancer, adenovirus enhancers, and retrovirus LTR enhancers.

In addition to containing sites for transcription initiation and control, expression vectors can also contain sequences necessary for transcription termination and, in the transcribed region a ribosome binding site for translation. Other regulatory control elements for expression include initiation and termination codons as well as polyadenylation signals. The person of ordinary skill in the art would be aware of the numerous regulatory sequences that are useful in expression vectors. Such regulatory sequences are described, for example, in Sambrook et al., *Molecular Cloning: A Laboratory Manual. 2nd. ed.,* Cold Spring Harbor Laboratory Press, Cold Spring Harbor, N.Y., (1989).

A variety of expression vectors can be used to express a nucleic acid molecule. Such vectors include chromosomal, episomal, and virus-derived vectors, for example vectors derived from bacterial plasmids, from bacteriophage, from yeast episomes, from yeast chromosomal elements, including yeast artificial chromosomes, from viruses such as baculoviruses, papovaviruses such as SV40, Vaccinia viruses, adenoviruses, pox viruses, pseudorabies viruses, and retroviruses. Vectors may also be derived from combinations of these sources such as those derived from plasmid and bacteriophage genetic elements, e.g. cosmids and phagemids. Appropriate cloning and expression vectors for prokaryotic and eukaryotic hosts are described in Sambrook et al., *Molecular Cloning: A Laboratory Manual. 2nd. ed.,* Cold Spring Harbor Laboratory Press, Cold Spring Harbor, N.Y., (1989).

The regulatory sequence may provide constitutive expression in one or more host cells (i.e. tissue specific) or may provide for inducible expression in one or more cell types such as by temperature, nutrient additive, or exogenous factor such as a hormone or other ligand. A variety of vectors providing for constitutive and inducible expression in prokaryotic and eukaryotic hosts are well known to those of ordinary skill in the art.

The nucleic acid molecules can be inserted into the vector nucleic acid by well-known methodology. Generally, the DNA sequence that will ultimately be expressed is joined to an expression vector by cleaving the DNA sequence and the expression vector with one or more restriction enzymes and then ligating the fragments together. Procedures for restriction enzyme digestion and ligation are well known to those of ordinary skill in the art.

The vector containing the appropriate nucleic acid molecule can be introduced into an appropriate host cell for propagation or expression using well-known techniques. Bacterial cells include, but are not limited to, *E. coli, Streptomyces,* and *Salmonella typhimurium.* Eukaryotic cells include, but are not limited to, yeast, insect cells such as *Drosophila,* animal cells such as COS and CHO cells, and plant cells.

As described herein, it may be desirable to express the peptide as a fusion protein. Accordingly, the invention provides fusion vectors that allow for the production of the peptides. Fusion vectors can increase the expression of a recombinant protein, increase the solubility of the recombinant protein, and aid in the purification of the protein by acting for example as a ligand for affinity purification. A proteolytic cleavage site may be introduced at the junction of the fusion moiety so that the desired peptide can ultimately be separated from the fusion moiety. Proteolytic enzymes include, but are not limited to, factor Xa, thrombin, and enteroRas-like protein. Typical fusion expression vectors include pGEX (Smith et al., *Gene* 67:31–40 (1988)), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Examples of suitable inducible non-fusion *E. coli* expression vectors include pTrc (Amann et al., *Gene* 69:301–315 (1988)) and pET 11d (Studier et al., *Gene Expression Technology: Methods in Enzymology* 185:60–89 (1990)).

Recombinant protein expression can be maximized in a host bacteria by providing a genetic background wherein the host cell has an impaired capacity to proteolytically cleave the recombinant protein. (Gottesman, S., *Gene Expression Technology: Methods in Enzymology* 185, Academic Press, San Diego, Calif., (1990) 119–128). Alternatively, the sequence of the nucleic acid molecule of interest can be altered to provide preferential codon usage for a specific host cell, for example *E. coli.* (Wada et al., *Nucleic Acids Res.* 20:2111–2118 (1992)).

The nucleic acid molecules can also be expressed by expression vectors that are operative in yeast. Examples of vectors for expression in yeast e.g., *S. cerevisiae* include pYepSec1 (Baldari, et al., *EMBO J.* 6:229–234 (1987)), pMFa (Kurjan et al., *Cell* 30:933–943(1982)), pJRY88 (Schultz et al., *Gene* 54:113–123 (1987)), and pYES2 (Invitrogen Corporation, San Diego, Calif.).

The nucleic acid molecules can also be expressed in insect cells using, for example, baculovirus expression vectors. Baculovirus vectors available for expression of proteins in cultured insect cells (e.g., Sf9 cells) include the pAc series (Smith et al., *Mol. Cell Biol.* 3:2156–2165 (1983)) and the pVL series (Lucklow et al., *Virology* 170:31–39 (1989)).

In certain embodiments of the invention, the nucleic acid molecules described herein are expressed in mammalian cells using mammalian expression vectors. Examples of mammalian expression vectors include pCDM8 (Seed, B. *Nature* 329:840(1987)) and pMT2PC (Kaufman et al., *EMBO J.* 6:187–195 (1987)).

The expression vectors listed herein are provided by way of example only of the well-known vectors available to those of ordinary skill in the art that would be useful to express the nucleic acid molecules. The person of ordinary skill in the art would be aware of other vectors suitable for maintenance, propagation, or expression of the nucleic acid molecules described herein. These are found for example in Sambrook, J., Fritsh, E. F., and Maniatis, T. *Molecular Cloning: A Laboratory Manual. 2nd, ed., Cold Spring Harbor Laboratory,* Cold Spring Harbor Laboratory Press, Cold Spring Harbor, N.Y., 1989.

The invention also encompasses vectors in which the nucleic acid sequences described herein are cloned into the vector in reverse orientation, but operably linked to a regulatory sequence that permits transcription of antisense RNA. Thus, an antisense transcript can be produced to all, or to a portion, of the nucleic acid molecule sequences described herein, including both coding and non-coding regions. Expression of this antisense RNA is subject to each of the parameters described above in relation to expression of the sense RNA (regulatory sequences, constitutive or inducible expression, tissue-specific expression).

The invention also relates to recombinant host cells containing the vectors described herein. Host cells therefore include prokaryotic cells, lower eukaryotic cells such as yeast, other eukaryotic cells such as insect cells, and higher eukaryotic cells such as mammalian cells.

The recombinant host cells are prepared by introducing the vector constructs described herein into the cells by techniques readily available to the person of ordinary skill in the art. These include, but are not limited to, calcium phosphate transfection, DEAE-dextran-mediated transfection, cationic lipid-mediated transfection, electroporation, transduction, infection, lipofection, and other techniques such as those found in Sambrook, et al. (*Molecular Cloning: A Laboratory Manual. 2nd, ed, Cold Spring Harbor Laboratory,* Cold Spring Harbor Laboratory Press, Cold Spring Harbor, N.Y., 1989).

Host cells can contain more than one vector. Thus, different nucleotide sequences can be introduced on different vectors of the same cell. Similarly, the nucleic acid molecules can be introduced either alone or with other nucleic acid molecules that are not related to the nucleic acid molecules such as those providing trans-acting factors for expression vectors. When more than one vector is introduced into a cell, the vectors can be introduced independently, co-introduced, or joined to the nucleic acid molecule vector.

In the case of bacteriophage and viral vectors, these can be introduced into cells as packaged or encapsulated virus by standard procedures for infection and transduction. Viral vectors can be replication-competent or replication-defective. In the case in which viral replication is defective, replication will occur in host cells providing functions that complement the defects.

Vectors generally include selectable markers that enable the selection of the subpopulation of cells that contain the recombinant vector constructs. The marker can be contained in the same vector that contains the nucleic acid molecules described herein or may be on a separate vector. Markers include tetracycline or ampicillin-resistance genes for prokaryotic host cells and dihydrofolate reductase or neomycin resistance for eukaryotic host cells. However, any marker that provides selection for a phenotypic trait will be effective.

While the mature proteins can be produced in bacteria, yeast, mammalian cells, and other cells under the control of the appropriate regulatory sequences, cell-free transcription and translation systems can also be used to produce these proteins using RNA derived from the DNA constructs described herein.

Where secretion of the peptide is desired, which is difficult to achieve with multi-transmembrane domain containing proteins such as kinases, appropriate secretion signals are incorporated into the vector. The signal sequence can be endogenous to the peptides or heterologous to these peptides.

Where the peptide is not secreted into the medium, which is typically the case with kinases, the protein can be isolated from the host cell by standard disruption procedures, including freeze thaw, sonication, mechanical disruption, use of lysing agents and the like. The peptide can then be recovered and purified by well-known purification methods including ammonium sulfate precipitation, acid extraction, anion or cationic exchange chromatography, phosphocellulose chromatography, hydrophobic-interaction chromatography, affinity chromatography, hydroxylapatite chromatography, lectin chromatography, or high performance liquid chromatography.

It is also understood that depending upon the host cell in recombinant production of the peptides described herein, the peptides can have various glycosylation patterns, depending upon the cell, or maybe non-glycosylated as when produced in bacteria. In addition, the peptides may include an initial modified methionine in some cases as a result of a host-mediated process.

Uses of Vectors and Host Cells

The recombinant host cells expressing the peptides described herein have a variety of uses. First, the cells are useful for producing a Ras-like protein polypeptide that can be further purified to produce desired amounts of Ras-like protein or fragments. Thus, host cells containing expression vectors are useful for peptide production.

Host cells are also useful for conducting cell-based assays involving the Ras-like protein or Ras-like protein fragments. Thus, a recombinant host cell expressing a native Ras-like protein is useful for assaying compounds that stimulate or inhibit Ras-like protein function.

Host cells are also useful for identifying Ras-like protein mutants in which these functions are affected. If the mutants naturally occur and give rise to a pathology, host cells containing the mutations are useful to assay compounds that have a desired effect on the mutant Ras-like protein (for example, stimulating or inhibiting function) which may not be indicated by their effect on the native Ras-like protein.

Genetically engineered host cells can be further used to produce non-human transgenic animals. A transgenic animal is preferably a mammal, for example a rodent, such as a rat or mouse, in which one or more of the cells of the animal include a transgene. A transgene is exogenous DNA which is integrated into the genome of a cell from which a transgenic animal develops and which remains in the genome of the mature animal in one or more cell types or tissues of the transgenic animal. These animals are useful for studying the function of a Ras-like protein and identifying and evaluating modulators of Ras-like protein activity. Other examples of transgenic animals include non-human primates, sheep, dogs, cows, goats, chickens, and amphibians.

A transgenic animal can be produced by introducing nucleic acid into the male pronuclei of a fertilized oocyte, e.g., by microinjection, retroviral infection, and allowing the oocyte to develop in a pseudopregnant female foster animal. Any of the Ras-like protein nucleotide sequences can be introduced as a transgene into the genome of a non-human animal, such as a mouse.

Any of the regulatory or other sequences useful in expression vectors can form part of the transgenic sequence. This includes intronic sequences and polyadenylation signals, if not already included. A tissue-specific regulatory sequence (s) can be operably linked to the transgene to direct expression of the Ras-like protein to particular cells.

Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo,* (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of transgenic mRNA in tissues or cells of the animals. A transgenic founder animal can then be used to breed additional animals carrying the transgene. Moreover, transgenic animals carrying a transgene can further be bred to other transgenic animals carrying other transgenes. A transgenic animal also includes animals in which the entire animal or tissues in the animal have been produced using the homologously recombinant host cells described herein.

In another embodiment, transgenic non-human animals can be produced which contain selected systems which allow for regulated expression of the transgene. One example of such a system is the cre/loxP recombinase system of bacteriophage P1. For a description of the cre/loxP recombinase system, see, e.g., Lakso et al. *PNAS* 89:6232–6236 (1992). Another example of a recombinase system is the FLP recombinase system of *S. cerevisiae* (O'Gorman et al. *Science* 251:1351–1355 (1991). If a cre/loxP recombinase system is used to regulate expression of the transgene, animals containing transgenes encoding both the Cre recombinase and a selected protein is required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. *Nature* 385:810–813 (1997) and PCT International Publication Nos. WO 97/07668 and WO 97/07669. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to pseudopregnant female foster animal. The offspring born of this female foster animal will be a clone of the animal from which the cell, e.g., the somatic cell, is isolated.

Transgenic animals containing recombinant cells that express the peptides described herein are useful to conduct the assays described herein in an in vivo context. Accordingly, the various physiological factors that are present in vivo and that could effect ligand binding, Ras-like protein activation, and signal transduction, may not be evident from in vitro cell-free or cell-based assays. Accordingly, it is useful to provide non-human transgenic animals to assay in vivo Ras-like protein function, including ligand interaction, the effect of specific mutant Ras-like proteins on Ras-like protein function and ligand interaction, and the effect of chimeric Ras-like proteins. It is also possible to assess the effect of null mutations, which is mutations that substantially or completely eliminate one or more Ras-like protein functions.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the above-described modes for carrying out the invention, which are obvious to those skilled in the field of molecular biology or related fields, are intended to be within the scope of the following claims.

That which is claimed is:

1. An isolated nucleic acid molecule consisting of a nucleotide sequence selected from the group consisting of:
   (a) a nucleotide sequence that encodes a polypeptide comprising the amino acid sequence of SEQ ID NO:2;
   (b) a nucleotide sequence consisting of SEQ ED NO:1;
   (c) a nucleotide sequence consisting of SEQ ED NO:3; and
   (d) a nucleotide sequence that is completely complementary over the entire length of a nucleotide sequence of (a)–(c).

2. A vector comprising the nucleic acid molecule of claim 1.

3. The vector of claim 2, wherein said vector is selected from the group consisting of a plasmid, a virus, and a bacteriophage.

4. The vector of claim 2, wherein said isolated nucleic acid molecule is inserted into said vector in proper orientation and correct reading frame such that a polypeptide comprising SEQ ID NO:2 may be expressed by a cell transformed with said vector.

5. The vector of claim 4, wherein said isolated nucleic acid molecule is operatively linked to a promoter sequence.

6. A host cell containing the vector of claim 2.

7. A process for producing a polypeptide comprising the amino acid sequence of SEQ ID NO:2, the process comprising culturing the host cell of claim 6 under conditions sufficient for the production of said polypeptide, and recovering said polypeptide, thereby producing said polypeptide.

8. An isolated polynucleotide consisting of the nucleotide sequence of SEQ ID NO:1.

9. An isolated polynucleotide consisting of the nucleotide sequence of SEQ ID NO:3.

* * * * *